(12) United States Patent
Balkovec et al.

(10) Patent No.: US 8,222,255 B2
(45) Date of Patent: Jul. 17, 2012

(54) ANTIFUNGAL AGENTS

(75) Inventors: James M. Balkovec, Martinsville, NJ (US); Phieng Siliphaivanh, Newtown, MA (US); Frances A. Bouffard, Scotch Plains, NJ (US); Roland A. Bouffard, legal representative, Scotch Plains, NJ (US); Michael R. Peel, Chapel Hill, NC (US); Weiming Fan, Chapel Hill, NC (US); Ahmed Mamai, Raleigh, NC (US); Sarah Dimick Gray, Eagan, MN (US)

(73) Assignees: Merck Sharp & Dohme Corp., Rahway, NJ (US); Scynexis, Inc., Research Triangle Park, NC (US)

( * ) Notice: Subject to any disclaimer, the term of this patent is extended or adjusted under 35 U.S.C. 154(b) by 0 days.

(21) Appl. No.: 12/680,472

(22) PCT Filed: Sep. 25, 2008

(86) PCT No.: PCT/US2008/011100
§ 371 (c)(1),
(2), (4) Date: Feb. 18, 2011

(87) PCT Pub. No.: WO2009/045311
PCT Pub. Date: Apr. 9, 2009

(65) Prior Publication Data
US 2011/0172225 A1  Jul. 14, 2011

Related U.S. Application Data

(60) Provisional application No. 60/995,719, filed on Sep. 28, 2007.

(51) Int. Cl.
*C07D 311/78* (2006.01)
*C07D 405/02* (2006.01)
*A61K 31/352* (2006.01)
*A61K 31/4025* (2006.01)
*A61K 31/4433* (2006.01)
*A61K 31/453* (2006.01)
*A61K 31/496* (2006.01)
*A61K 31/506* (2006.01)
*A61K 31/5355* (2006.01)

(52) U.S. Cl. .......... 514/254.11; 514/422; 514/378; 514/297; 514/453; 514/316; 514/320; 549/382; 548/525; 548/243; 548/311.4; 546/196; 546/187; 544/150; 544/375

(58) Field of Classification Search .......... None
See application file for complete search history.

(56) References Cited

U.S. PATENT DOCUMENTS
5,756,472 A * 5/1998 Liesch et al. .......... 514/27

OTHER PUBLICATIONS

Byrn, et al., Solid-State Chemistry of Drugs, 2d, Chapter 11:Hydrates and Solvates, 233 247 (1999).*
Rouhi, Chem. & Eng. News, Feb. 24, 2003, 81(8), 32-35.*
Morissette, et al. Advanced Drug Delivery Reviews 56:275 (2004).*
Gennaro, A. (ed.), *Remington: The Science and Practice of Pharmacy*, 19th edition (1995).
Onishi, J., et al., "Discovery of Novel Antifungal (1,3)-β-D-Glucan Synthase Inhibitors," *Antimicrobial Agents and Chemotherapy*, vol. 44, No. 2, pp. 368-377 (2000).
Pelaez, F., et al., "The Discovery of Enfumafungin, a Novel Antifungal Compound Produced by an Endophytic *Hormonema* Species—Biological Activity and Taxonomy of the Producing Organisms," *Systematic and Applied Microbiology*, vol. 23, No. 3, pp. 333-343 (2000).
Schwartz, R. et al., "Isolation and Structural Determination of Enfumafungin, a Triterpene Glycoside Antifungal Agent That Is a Specific Inhibitor of Glucan Synthesis," *Journal of the American Chemical Society*, vol. 122, No. 16-20, pp. 4882-4886 (2000).
Schwartz, R., "Cell wall active antifungal agents," *Expert Opinion on Therapeutic Patents*, vol. 11(11), pp. 1761-1772 (2001).

* cited by examiner

Primary Examiner — Yong Chu
Assistant Examiner — Michael Barker
(74) Attorney, Agent, or Firm — Covington & Burling LLP; Paul J. Berman; Melody Wu

(57) ABSTRACT

Novel derivatives of enfumafungin are disclosed herein, along with their, pharmaceutically acceptable salts, hydrates and prodrugs. Also disclosed are compositions comprising such compounds, methods of preparing such compounds and methods of using such compounds as antifungal agents and/or inhibitors of (1,3)-β-D-glucan synthase. The disclosed compounds, their pharmaceutically acceptable salts, hydrates and prodrugs, as well as compositions comprising such compounds, salts, hydrates and prodrugs, are useful for treating and/or preventing fungal infections and associated diseases and conditions.

17 Claims, No Drawings

ANTIFUNGAL AGENTS

JOINT RESEARCH AGREEMENT

The claimed subject matter was made as a result of activities undertaken within the scope of a joint research agreement between Merck & Co., Inc. and Scynexis, Inc.

FIELD OF THE INVENTION

The claimed subject matter relates to novel compounds and pharmaceutically acceptable salts, hydrates and prodrugs thereof, compositions containing such compounds, synthesis of such compounds, and use of such compounds as antifungal agents and/or inhibitors of (1,3)-β-D-glucan synthesis. The compounds described herein are derivatives of enfumafungin. The novel compounds of this disclosure, their pharmaceutically acceptable salts, hydrates and prodrugs, and compositions comprising such compounds, salts, hydrates and/or prodrugs, are useful for treating and/or preventing fungal infections and associated diseases and conditions.

BACKGROUND OF THE INVENTION

Fungal infection is a major healthcare problem, and the incidence of hospital-acquired fungal diseases continues to rise. Severe systemic fungal infection in hospitals (such as candidiasis, aspergillosis, histoplasmosis, blastomycosis and coccidioidomycosis) is commonly seen in neutropaenic patients following chemotherapy and in other oncology patients with immune suppression, in patients who are immune-compromised due to Acquired Immune Deficiency Syndrome (AIDS) caused by HIV infection, and in patients in intensive care. Systemic fungal infections cause ~25% of infection-related deaths in leukaemics. Infections due to Candida species are the fourth most important cause of nosocomial bloodstream infection. Serious fungal infections may cause 5-10% of deaths in patients undergoing lung, pancreas or liver transplantation. Treatment failures are still very common with all systemic mycoses. Secondary resistance also arises. Thus, there remains an increasing need for effective new therapy against mycotic infections.

Enfumafungin is a hemiacetal triterpene glycoside that is produced in fermentations of a *Hormonema* spp. associated with living leaves of *Juniperus communis* (U.S. Pat. No. 5,756,472; Pelaez et al., *Systematic and Applied Microbiology*, 23:333-343, 2000; Schwartz et al., *JACS*,122:4882-4886, 2000; Schwartz, R. E., *Expert Opinion on Therapeutic Patents*, 11(11):1761-1772, 2001). Enfumafungin is one of the several triterpene glycosides that have in vitro antifungal activities. The mode of the antifungal action of enfumafungin and other antifungal triterpenoid glycosides was determined to be the inhibition of fungal cell wall glucan synthesis by their specific action on (1,3)-β-D-glucan synthase (Onishi et al., *Antimicrobial Agents and Chemotherapy*, 44:368-377, 2000; Pelaez et al., *Systematic and Applied Microbiology*, 23:333-343, 2000). 1,3-β-D-Glucan synthase remains an attractive target for antifungal drug action because it is present in many pathogenic fungi which affords broad antifungal spectrum and there is no mammalian counterpart and as such, these compounds have little or no mechanism-based toxicity.

SUMMARY OF THE INVENTION

The present disclosure relates to novel enfumafungin derivatives. These compounds or pharmaceutically acceptable salts are useful in the inhibition of (1,3)-β-D-glucan synthase inhibitors, and thus in the prevention or treatment of mycotic infections caused by various pathogens including, but are not limited to, *Aspergillus, Cryptococcus, Candida, Mucor, Actinomyces, Histoplasma, Dermatophyte, Malassezia, Fusarium, Pneumocystis carinii*. In particular, the present invention includes a compound of Formula (I):

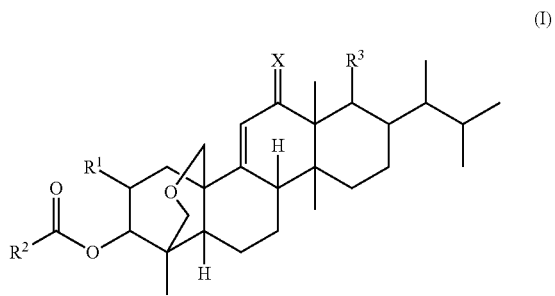

or a pharmaceutically acceptable salt, hydrate or prodrug thereof, wherein:

X is selected from the group consisting of O and H,H;

$R^1$ is selected from the group consisting of:

a) OH, b) O—$(C_1$-$C_{12})$alkyl, c) O—$(C_3$-$C_8)$cycloalkyl, d) O-heterocyclyl e) OC(O)H, f) OC(O)—$(C_1$-$C_{12})$alkyl, g) OC(O)—$(C_3$-$C_8)$cycloalkyl, and h) OC(O)-(heterocyclyl), where the heterocyclyl groups are chosen from 5- to 8-membered rings containing from 1 to 4 heteroatoms independently selected from N, O and S;

$R^2$ is selected from the group consisting of:

a) $(C_1$-$C_{12})$alkyl, and b) heterocyclyl, where the heterocyclyl groups are chosen from 5- to 8-membered rings containing from 1 to 4 heteroatoms independently selected from N, O and S, and $R^2$ is substituted by 0 to $4R^4$ groups;

$R^3$ is selected from the group consisting of:

a) $CH_2OH$, b) $CH_2OC(O)(C_1$-$C_{12}$alkyl), c) COOH, d) COO$(C_1$-$C_{12})$alkyl, and e) COO$(CH_2)_{0-6}$phenyl;

each $R^4$ is independently selected from the group consisting of:

a) $(C_1$-$C_{12})$alkyl, b) $(C_3$-$C_8)$cycloalkyl, c) OH, d) $NR^5_2$, e) $ONR^5_2$, f) O$(C_1$-$C_{12})$alkyl, g) C(O)R⁶,
h) S(O)₂R⁶, and
i)

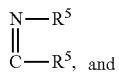

each R⁴ is substituted by 0 to 4R⁷ groups;
each R⁵ is independently selected from the group consisting of:
  a) H,
  b) (CH₂)₀₋₁₂R⁶,
  c) C(O)R⁶,
  d) S(O)₂R⁶, and
  e)

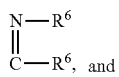

each R⁵ is substituted by 0 to 13R⁷ groups;
each R⁶ is independently selected from the group consisting of:
  a) H,
  b) OH,
  c) (C₁-C₁₂)alkyl,
  d) O—(C₁-C₁₂)alkyl,
  e) (C₃-C₁₂)cycloalkyl,
  f) (CH₂)₀₋₆-phenyl,
  g) heterocyclyl, where the heterocyclyl groups are chosen from 5- to 8-membered rings containing from 1 to 4 heteroatoms independently selected from N, O and S,
  h) C(O)R⁸,
  i) NR⁸₂,
  j) halogen, and
  each R⁶ is substituted by 0 to 13R⁷ groups;
each R⁷ is independently selected from the group consisting of:
  a) OH,
  b) (C₁-C₁₂)alkyl,
  c) O—(C₁-C₁₂)alkyl,
  d) S—(C₁-C₁₂)alkyl,
  e) (CH₂)₀₋₆-phenyl,
  f) heterocyclyl, where the heterocyclyl groups are chosen from 5- to 8-membered rings containing from 1 to 4 heteroatoms independently selected from N, O and S,
  g) C(O)R⁸,
  h) OC(O)R⁸,
  i) NR⁸₂,
  j) halogen, and
  each R⁷ is substituted by 0 to 13R⁹ groups;
each R⁸ is independently selected from the group consisting of:
  a) H,
  b) (C₁-C₁₂)alkyl,
  c) O—(C₁-C₁₂)alkyl,
  d) (C₃-C₁₂)cycloalkyl,
  e) (CH₂)₀₋₆-phenyl,
  f) heterocyclyl, where the heterocyclyl groups are chosen from 5- to 8-membered rings containing from 1 to 4 heteroatoms independently selected from N, O and S,
  g) C(O)R¹¹, and
  each R⁸ is substituted by 0 to 13R⁹ groups;
each R⁹ is independently selected from the group consisting of:
  a) OH,
  b) (C₁-C₁₂)alkyl,
  c) O—(C₁-C₁₂)alkyl,
  d) (C₃-C₁₂)cycloalkyl,
  e) heterocyclyl, where the heterocyclyl groups are chosen from 5- to 8-membered rings containing from 1 to 4 heteroatoms independently selected from N, O and S,
  f) C(O)R¹¹,
  g) NR¹¹₂,
  h) halogen, and
  each R⁹ is substituted by 0 to 13R¹⁰ groups;
each R¹⁰ is independently selected from the group consisting of:
  a) halogen,
  b) =O, and
  c) C(O)R¹¹; and
R¹¹ is selected from the group consisting of:
  a) H, and
  b) (C₁-C₁₂)alkyl.

These compounds are potent antifungal agents with broad spectra of activity and can be used against pathogens associated with human and agricultural fungal infections.

Additional aspects of the invention relate to compositions comprising the compounds of the invention, optionally in the presence of a second therapeutic agent. In addition, aspects of the invention relate to methods of preparing a compound of the invention, to methods of preparing compositions of the invention, to methods of treating or preventing fungal infection in patients using a compound of the invention, and to methods of controlling fungal infection in patients using a compound of the invention.

Other embodiments, aspects and features of the present invention are either further described in or will be apparent from the ensuing description, examples and appended claims.

DETAILED DESCRIPTION OF THE INVENTION

The present invention relates to compounds of Formula (I), as described above, and pharmaceutically acceptable salts thereof These compounds are useful as (1,3)-β-D-glycan synthase inhibitors. These compounds include, but are not limited to, compounds of that have structural Formula (Ia), in which all variables are as defined for Formula (I).

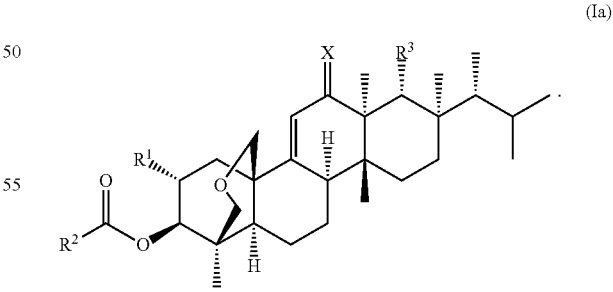

(Ia)

An additional embodiment comprises compounds of Formula (I) or (Ia), or pharmaceutically acceptable salts thereof, in which X is O.

Another embodiment comprises compounds of Formula (I) or (Ia), or pharmaceutically acceptable salts thereof, in which R¹ is selected from the group consisting of OC(O)H and OC(O)—(C₁-C₁₂)alkyl.

Yet another embodiment comprises compounds of Formula (I) or (Ia), or pharmaceutically acceptable salts thereof, in which $R^2$ is selected from the group consisting of $(C_1-C_{12})$ alkyl that are substituted by 1 to $4R^4$ groups; and said $R^4$ groups are independently selected from the group consisting of OH, $NR^5_2$, $O(C_1-C_{12})$alkyl, $C(O)R^6$ and $S(O)_2R^6$. In first aspect of this embodiment, the $R^4$ groups are independently selected from the group consisting of $NR^5_2$, $C(O)R^6$ and $S(O)_2R^6$; each $R^5$ is independently selected from the group consisting of H and $(CH_2)_{0-12}R^6$; $R^6$ is selected from the group consisting of H, OH and $(C_1-C_{12})$alkyl; and said $R^6$ is substituted by 0 to 2 $NH_2$ groups. In a second aspect of this embodiment, the $R^2$ is substituted by $NH_2$ and $NHR^5$; $R^5$ is selected from the group consisting of H and $(CH_2)_{0-12}R^6$; and $R^6$ is selected from the group consisting of $(C_1-C_{12})$alkyl, $(C_3-C_{12})$cycloalkyl, $(CH_2)_{0-6}$phenyl, and heterocyclyl. In a particular case of this second aspect, $R^6$ is substituted by 0 to $4R^7$; and each $R^7$ is independently selected from halogen and $O(C_1-C_{12})$alkyl groups.

An additional embodiment comprises compounds of Formula (I) or (Ia), or pharmaceutically acceptable salts thereof, in which $R^2$ is selected from the group consisting of heterocyclyl, where said heterocyclyl group is a 5- to 6-membered ring containing from 1 to 4 heteroatoms independently selected from N, O and S. In a first aspect of this embodiment, $R^2$ is substituted by 1 to $4R^4$ groups; and said $R^4$ groups are independently selected from the group consisting of OH, $NR^5_2$, $O(C_1-C_{12})$alkyl, $C(O)R^6$ and $S(O)_2R^6$. In a particular instance of this aspect, the $R^4$ groups are independently selected from the group consisting of $NR^5_2$, $C(O)R^6$ and $S(O)_2R^6$; each $R^5$ is independently selected from the group consisting of H and $(CH_2)_{0-12}R^6$; $R^6$ is selected from the group consisting of H, OH and $(C_1-C_{12})$alkyl; and $R^6$ is substituted by 0 to 2 $NH_2$ groups.

A further embodiment comprises compounds of Formula (I) or (Ia), or pharmaceutically acceptable salts thereof, in which $R^3$ is C(O)OH.

Still further, embodiments include compounds of Formula (I) or (Ia) in which various selections are made of formula variables. One such embodiment, for example, is a compound of Formula (I) or (Ia) in which $R^1$ is selected from the group consisting of O—$(C_1-C_{12})$alkyl, OC(O)H and OC(O)—$(C_1-C_{12})$alkyl; $R^2$ is selected from the group consisting of $(C_1-C_{12})$alkyl and heterocyclyl, which are chosen from 5- to 8-membered rings containing from 1 to 4 heteroatoms independently selected from N, O and S, and said $R^2$ is substituted by 0 to $4R^4$ groups; $R^3$ is COOH; each $R^4$ is independently selected from the group consisting of OH, $NR^5_2$, $O(C_1-C_{12})$alkyl, $C(O)R^6$ and $S(O)_2R^6$, and each $R^4$ is substituted by 0 to $4R^7$ groups; each $R^5$ is independently selected from the group consisting of H and $(CH_2)_{0-12}R^6$, and each $R^5$ is substituted by 0 to $13R^7$ groups; each $R^6$ is independently selected from the group consisting of H, $(C_1-C_{12})$alkyl, $(C_3-C_{12})$cycloalkyl, $(CH_2)_{0-6}$-phenyl, heterocyclyl and halogen, and said $R^6$ is substituted by 0 to $13R^7$ groups; and each $R^7$ is independently selected from the group consisting of O—$(C_1-C_{12})$alkyl, and halogen, and each $R^7$ is unsubstituted.

Yet another embodiment comprises compounds of Formula (I) or (Ia), or pharmaceutically acceptable salts thereof, in which the compound is selected from the group consisting of (1S,2R,3R,4aR,6aS,7R,8R,10aR,10bR,12aR)-3-(acetyloxy)-2-(2-amino-3-methyl-butyryloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-4-carbamoyl-butyryloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-pentanoyloxy)-8-[(1R)-1,2-dimethylpropyl]1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2,6-diamino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-4-hydroxy-butyryloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2,5-diamino-pentanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-butyryloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-3-carboxypropionyoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-piperidinylcarboxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-pyrrolidinylcarboxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(3-amino-propionyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(3-amino-butyryloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(3-amino-propionyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-5-formylamino-pentanoyloxy)-8-

[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(4-amino-pyrrolidine-2-carboxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-guanidino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(2-amino-acetylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(2-methylamino-acetylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(4-hydroxy-pyrrolidine-2-carboxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-3-(2-amino-ethoxy)-propionyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-3-(2-amino-ethanesulfonyl)-propionyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-3-(2-amino-ethylamino)-propionyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(2-amino-ethylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(4-amino-5-hydroxy-pentanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(N-hydroxycarbamimidoyl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(N-(2,6-diaminohexanoyloxy)carbamimidoyl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(3,5-bis-trifluoromethyl-benzoylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(3-bromo-benzoylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(2,2,3,3,4,4,4-heptafluoro-butyrylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(2-bromo-propionylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(2-methoxy-acetylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-[(tetrahydro-furan-2-carbonyl)-amino]-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(3-methoxy-benzoylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(3-fluoro-benzoylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-phenylacetylamino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(cyclobutanecarbonyl-amino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(3,5-dimethoxy-benzoylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(2-oxo-propionylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(3-chloro-benzoylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-propionylamino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(4-chloro-benzoylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(6-(2-acetoxy-2-methyl-propionylamino)-2-amino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(6-acetylamino-2-amino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(2,2,2-trifluoro-acetylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-[3-(4-fluoro-phenyl)-ureido]-hexanoyloxy hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-[3-(4-trifluoromethylphenyl)-ureido]-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(3-isopropyl-ureido)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-[3-(4-methoxyphenyl)-ureido]-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(3-cyclopentyl-ureido)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-[3-(1-methoxycarbonyl-ethyl)-ureido]-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-[3-(2-bromo-ethyl)-ureido]-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-[3-(2-chloro-ethyl)-ureido]-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(3-hexylureido)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(3-phenyl-ureido)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-[3-(4-methoxycarbonylphenyl)-ureido]-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(3-ethoxycarbonylmethy-ureido)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(4-tert-butylbenzenesulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(4-trifluoromethylbenzenesulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(4-fluorobenzenesulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(4-bromobenzenesulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(4-methoxybenzenesulfonylamino)-hexanoyloxy)-8-[(1R)-1,2-dimethylpropyl]-1,6a,8,10a- tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(3,5-dimethylisoxazole-4-sulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-methanesulfonylamino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-ethanesulfonylamino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-propanesulfonylamino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(3-chloropropane-1-sulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(3,5-bis-trifluoromethylbenzenesulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(3-trifluoromethylbenzenesulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(6-(4-acetylamino-benzenesulfonylamino)-2-amino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(3-chloro-4-fluorobenzenesulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(toluene-2-sulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-6-(3,4-dimethoxy-benzenesulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(2,2-dimethyl-propylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-[(tetrahydro-furan-2-ylmethyl)-amino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-[2-(4-fluoro-phenyl)-1-methyl-ethylamino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(tetrahydro-pyran-4-ylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-isopropylaminoacetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(2-methyl-tetrahydro-furan-3-ylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(1-methyl-3-methylsulfanyl-propylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(4-diethylamino-1-methyl-butylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-[(1-Methyl-pyrrolidin-2-ylmethyl)-amino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(1-methyl-piperidin-4-ylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(2-methoxy-1-methyl-ethylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(2-methyl-cyclopentylamino)-acetoxy)-8-[(1R)-1,2-dimethylpropyl]-1,6a,8,10a-tetramethyl-1,3,4, 6,6a,7,8,9,10,10a,10b,11,12,12a-tetradecahydro-2H-1,
4a-(methanooxymethano)chrysene-7-carboxylic acid;
(1S,2R,3R,4aR,6aS,7R,8R,10aR,10bR,12aR)-3-(acety-
loxy)-2-(2-guanidino-acetoxy)-8-[(1R)-1,2-dimethylpro-
pyl]-1,6a,8,10a-tetramethyl-1,3,4,6,6a,7,8,9,10,10a,10b,
11,12,12a-tetradecahydro-2H-1,4a-
(methanooxymethano)chrysene-7-carboxylic acid;
(1S,2R,3R,4aR,6aS,7R,8R,10aR,10bR,12aR)-3-(acety-
loxy)-2-(2-(cyclopropylmethyl-propyl-amino)-acetoxy)-
8-[(1R)-1,2-dimethylpropyl]-1,6a,8,10a-tetramethyl-1,3,
4,6,6a,7,8,9,10,10a,10b,11,12,12a-tetradecahydro-2H-1,
4a-(methanooxymethano)chrysene-7-carboxylic acid;
(1S,2R,3R,4aR,6aS,7R,8R,10aR,10bR,12aR)-3-(acety-
loxy)-2-(2-[bis-(2-hydroxy-ethyl)-amino]-acetoxy)-8-
[(1R)-1,2-dimethylpropyl]-1,6a,8,10a-tetramethyl-1,3,4,
6,6a,7,8,9,10,10a,10b,11,12,12a-tetradecahydro-2H-1,
4a-(methanooxymethano)chrysene-7-carboxylic acid;
(1S,2R,3R,4aR,6aS,7R,8R,10aR,10bR,12aR)-3-(acety-
loxy)-2-(2-[4-(4-fluoro-2-methoxyphenyl)-piperidin-1-
yl]-acetoxy)-8-[(1R)-1,2-dimethylpropyl]-1,6a,8,10a-tet-
ramethyl-1,3,4,6,6a,7,8,9,10,10a,10b,11,12,12a-
tetradecahydro-2H-1,4a-(methanooxymethano)chrysene-
7-carboxylic acid;
(1S,2R,3R,4aR,6aS,7R,8R,10aR,10bR,12aR)-3-(acety-
loxy)-2-(2-(2-piperidin-1-ylethylamino)-acetoxy)-8-
[(1R)-1,2-dimethylpropyl]-1,6a,8,10a-tetramethyl-1,3,4,
6,6a,7,8,9,10,10a,10b,11,12,12a-tetradecahydro-2H-1,
4a-(methanooxymethano)chrysene-7-carboxylic acid;
(1S,2R,3R,4aR,6aS,7R,8R,10aR,10bR,12aR)-3-(acety-
loxy)-2-(2-(3-imidazol-1-ylpropylamino)-acetoxy)-8-
[(1R)-1,2-dimethylpropyl]-1,6a,8,10a-tetramethyl-1,3,4,
6,6a,7,8,9,10,10a,10b,11,12,12a-tetradecahydro-2H-1,
4a-(methanooxymethano)chrysene-7-carboxylic acid;
(1S,2R,3R,4aR,6aS,7R,8R,10aR,10bR,12aR)-3-(acety-
loxy)-2-(2-(cyclohexyl-methylamino)-acetoxy)-8-[(1R)-
1,2-dimethylpropyl]-1,6a,8,10a-tetramethyl-1,3,4,6,6a,7,
8,9,10,10a,10b,11,12,12a-tetradecahydro-2H-1,4a-
(methanooxymethano)chrysene-7-carboxylic acid;
(1S,2R,3R,4aR,6aS,7R,8R,10aR,10bR,12aR)-3-(acety-
loxy)-2-(2-pyrrolidin-1-yl-acetoxy)-8-[(1R)-1,2-dimeth-
ylpropyl]-1,6a,8,10a tetramethyl1,3,4,6,6a,7,8,9,10,10a,
10b,11,12,12a-tetradecahydro-2H-1,4a-
(methanooxymethano)chrysene-7-carboxylic acid;
(1S,2R,3R,4aR,6aS,7R,8R,10aR,10bR,12aR)-3-(acety-
loxy)-2-(2-(3-hydroxy-pyrrolidin-1-yl)-acetoxy)-8-[(1R)-
1,2-dimethylpropyl]-1,6a,8,10a-tetramethyl-1,3,4,6,6a,7,
8,9,10,10a,10b,11,12,12a-tetradecahydro-2H-1,4a-
(methanooxymethano)chrysene-7-carboxylic acid;
(1S,2R,3R,4aR,6aS,7R,8R,10aR,10bR,12aR)-3-(acety-
loxy)-2-(2-[4-(4-fluoro-phenyl)-piperazin-1-yl]-ac-
etoxy)-8-[(1R)-1,2-dimethylpropyl]-1,6a,8,10a-tetram-
ethyl-1,3,4,6,6a,7,8,9,10,10a,10b,11,12,12a-
tetradecahydro-2H-1,4a-(methanooxymethano)chrysene-
7-carboxylic acid;
(1S,2R,3R,4aR,6aS,7R,8R,10aR,10bR,12aR)-3-(acety-
loxy)-2-(2-(4-methyl-piperazin-1-yl)-acetoxy)-8-[(1R)-1,
2-dimethylpropyl]-1,6a,8,10a-tetramethyl-1,3,4,6,6a,7,8,
9,10,10a,10b,11,12,12a-tetradecahydro-2H-1,4a-
(methanooxymethano)chrysene-7-carboxylic acid;
(1S,2R,3R,4aR,6aS,7R,8R,10aR,10bR,12aR)-3-(acety-
loxy)-2-(2-morpholin-4-yl-acetoxy)-8-[(1R)-1,2-dimeth-
ylpropyl]-1,6a,8,10a-tetramethyl-1,3,4,6,6a,7,8,9,10,10a,
10b,11,12,12a-tetradecahydro-2H-1,4a-
(methanooxymethano)chrysene-7-carboxylic acid;
(1S,2R,3R,4aR,6aS,7R,8R,10aR,10bR,12aR)-3-(acety-
loxy)-2-(2-dimethylamino-acetoxy)-8-[(1R)-1,2-dimeth-
ylpropyl]-1,6a,8,10a-tetramethyl-1,3,4,6,6a,7,8,9,10,10a,
10b,11,12,12a-tetradecahydro-2H-1,4a-
(methanooxymethano)chrysene-7-carboxylic acid;
(1S,2R,3R,4aR,6aS,7R,8R,10aR,10bR,12aR)-3-(acety-
loxy)-2-(2-[(2,2-dimethoxyethyl)-methyl-amino]-ac-
etoxy)-8-[(1R)-1,2-dimethylpropyl]-1,6a,8,10a-tetram-
ethyl-1,3,4,6,6a,7,8,9,10,10a,10b,11,12,12a-
tetradecahydro-2H-1,4a-(methanooxymethano)chrysene-
7-carboxylic acid;
(1S,2R,3R,4aR,6aS,7R,8R,10aR,10bR,12aR)-3-(acety-
loxy)-2-(2-(ethyl-methyl-amino)-acetoxy)-8-[(1R)-1,2-
dimethylpropyl]-1,6a,8,10a-tetramethyl-1,3,4,6,6a,7,8,9,
10,10a,10b,11,12,12a-tetradecahydro-2H-1,4a-
(methanooxymethano)chrysene-7-carboxylic acid;
(1S,2R,3R,4aR,6aS,7R,8R,10aR,10bR,12aR)-3-(acety-
loxy)-2-(2-[(2-diethylamino-ethyl)-methylamino]-ac-
etoxy)-8-[(1R)-1,2-dimethylpropyl]-1,6a,8,10a-tetram-
ethyl-1,3,4,6,6a,7,8,9,10,10a,10b,11,12,12a-
tetradecahydro-2H-1,4a-(methanooxymethano)chrysene-
7-carboxylic acid;
(1S,2R,3R,4aR,6aS,7R,8R,10aR,10bR,12aR)-3-(acety-
loxy)-2-(2-(4-ethyl-piperazin-1-yl)-acetoxy)-8-[(1R)-1,2-
dimethylpropyl]-1,6a,8,10a-tetramethyl-1,3,4,6,6a,7,8,9,
10,10a,10b,11,12,12a-tetradecahydro-2H-1,4a-
(methanooxymethano)chrysene-7-carboxylic acid;
(1S,2R,3R,4aR,6aS,7R,8R,10aR,10bR,12aR)-3-(acety-
loxy)-2-(2-(2-pyrrolidin-1-yl-ethylamino)-acetoxy)-8-
[(1R)-1,2-dimethylpropyl]-1,6a,8,10a-tetramethyl-1,3,4,
6,6a,7,8,9,10,10a,10b,11,12,12a-tetradecahydro-2H-1,
4a-(methanooxymethano)chrysene-7-carboxylic acid;
(1S,2R,3R,4aR,6aS,7R,8R,10aR,10bR,12aR)-3-(acety-
loxy)-2-(2-[3-(2-oxo-pyrrolidin-1-yl)-propylamino]-ac-
etoxy)-8-[(1R)-1,2-dimethylpropyl]-1,6a,8,10a-tetram-
ethyl-1,3,4,6,6a,7,8,9,10,10a,10b,11,12,12a-
tetradecahydro-2H-1,4a-(methanooxymethano)chrysene-
7-carboxylic acid;
(1S,2R,3R,4aR,6aS,7R,8R,10aR,10bR,12aR)-3-(acety-
loxy)-2-(2-(2-morpholin-4-yl-ethylamino)-acetoxy)-8-
[(1R)-1,2-dimethylpropyl]-1,6a,8,10a-tetramethyl-1,3,4,
6,6a,7,8,9,10,10a,10b,11,12,12a-tetradecahydro-2H-1,
4a-(methanooxymethano)chrysene-7-carboxylic acid;
(1S,2R,3R,4aR,6aS,7R,8R,10aR,10bR,12aR)-3-(acety-
loxy)-2-(2-(1-ethoxycarbonylpiperidin-4-yl)-amino-ac-
etoxy)-8-[(1R)-1,2-dimethylpropyl]-1,6a,8,10a-tetram-
ethyl-1,3,4,6,6a,7,8,9,10,10a,10b,11,12,12a-
tetradecahydro-2H-1,4a-(methanooxymethano)chrysene-
7-carboxylic acid;
(1S,2R,3R,4aR,6aS,7R,8R,10aR,10bR,12aR)-3-(acety-
loxy)-2-(2-(2-methoxy-1-methyl-ethylamino)-acetoxy)-
8-[(1R)-1,2-dimethylpropyl]-1,6a,8,10a-tetramethyl-1,3,
4,6,6a,7,8,9,10,10a,10b,11,12,12a-tetradecahydro-2H-1,
4a-(methanooxymethano)chrysene-7-carboxylic acid;
(1S,2R,3R,4aR,6aS,7R,8R,10aR,10bR,12aR)-3-(acety-
loxy)-2-(2-methylamino-acetoxy)-8-[(1R)-1,2-dimethyl-
propyl]-1,6a,8,10a-tetramethyl-1,3,4,6,6a,7,8,9,10,10a,
10b,11,12,12a-tetradecahydro-2H-1,4a-
(methanooxymethano)chrysene-7-carboxylic acid;
(1S,2R,3R,4aR,6aS,7R,8R,10aR,10bR,12aR)-3-(acety-
loxy)-2-(2-(2-dimethylamino-ethylamino)-acetoxy)-8-
[(1R)-1,2-dimethylpropyl]-1,6a,8,10a-tetramethyl-1,3,4,
6,6a,7,8,9,10,10a,10b,11,12,12a-tetradecahydro-2H-1,
4a-(methanooxymethano)chrysene-7-carboxylic acid;
(1S,2R,3R,4aR,6aS,7R,8R,10aR,10bR,12aR)-3-(acety-
loxy)-2-(2-(3-isopropoxy-propylamino)-acetoxy)-8-
[(1R)-1,2-dimethylpropyl]-1,6a,8,10a-tetramethyl-1,3,4,
6,6a,7,8,9,10,10a,10b,11,12,12a-tetradecahydro-2H-1,
4a-(methanooxymethano)chrysene-7-carboxylic acid;

(1S,2R,3R,4aR,6aS,7R,8R,10aR,10bR,12aR)-3-(acetyloxy)-2-(2-(1,2,2,6,6-pentamethyl-piperidin-4-ylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-[(piperidin-4-ylmethyl)-amino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-[3-(2-methyl-piperidin-1-yl)-propylamino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(3-methylamino-propylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(3-dimethylamino-propylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(3-pyrrolidin-1-yl-propylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-[(3-dimethylaminopropyl)-methyl-amino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (1S,2R,3R,4aR,6aS,7R,8R,10aR,10bR,12aR)-3-(acetyloxy)-2-(2-[bis-(3-dimethylaminopropyl)-amino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(4-pyrrolidin-1-yl-piperidin-1-yl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(3-acetylamino-pyrrolidin-1-yl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(1-methyl-pyrrolidin-3-ylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(3-dimethylamino-pyrrolidin-1-yl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(4-isopropyl-piperazin-1-yl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(3-diethylamino-pyrrolidin-1-yl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-[methyl-(1-methylpiperidin-4-yl)-amino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-[1,4']Bipiperidinyl-1'-yl-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-aminoacetoxy)-8-[(1R)-1,2-dimethylpropyl]-1,6a,,10a-tetramethyl-6-oxo-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(pyrrolidine-2-carbonyloxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2,5-diamino-pentanoyloxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(2-amino-acetylamino)-acetoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(2-methylamino-acetylamino)-acetoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2,6-diamino-hexanoyloxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-((4-aminopyrrolidine)-2-carbonyloxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-5-guanidino-pentanoyloxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-2-(2,6-diamino-hexanoyloxy)-3-(methoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-2-(2,6-diamino-hexanoyloxy)-3-(ethoxy)-8-[(1R)-1,2-dimethylpropyl]-1,6a,8,10a-tetramethyl-1,3,4,6,6a,7,8,9,10,10a, 10b,11,12,12a-tetradecahydro-2H-1,4a-(methanooxymethano)chrysene-7-carboxylic acid; and (1S,2R,3R,4aR,6aS,7R,8R,10aR,10bR,12aR)-2-(2,6-diamino-hexanoyloxy)-3-((2-methyl)ethoxy)-8-[(1R)-1,2-dimethylpropyl]-1,6a,8,10a-tetramethyl-1,3,4,6,6a,7,8,9, 10,10a,10b,11,12,12a-tetradecahydro-2H-1,4a-(methanooxymethano)chrysene-7-carboxylic acid.

Other embodiments of the present invention include the following:

(a) A composition comprising a compound of Formula (I) or (Ia) and a carrier, adjuvant, or vehicle;

(b) A pharmaceutical composition comprising a compound of Formula (I) or (Ia) and a pharmaceutically acceptable carrier, adjuvant, or vehicle;

(c) The pharmaceutical composition of (b), further comprising a second therapeutic agent;

(d) The pharmaceutical composition of (c), wherein the second therapeutic agent is an azole, a polyene, a purine or pyrimidine nucleotide inhibitor, a pneumocandin or echinocandin derivative, a protein elongation factor inhibitor, a chitin inhibitor, a mannan inhibitor, a bactericidal/permeability-inducing (BPI) protein product, or an immunomodulating agent;

(e) The pharmaceutical composition of (d), wherein the second therapeutic agent is itraconazole, ketoconazole, miconazole, fluconazole, voriconazole, posaconazole, amphotericin B, flucytosine, anidulafungin, micafungin, or caspofungin;

(f) A pharmaceutical combination which is (1) a compound of Formula (I) or (Ia) and (2) a second therapeutic agent, wherein the compound of Formula (I) and the second therapeutic agent are each employed in an amount that renders the combination effective for treating or preventing fungal/bacterial infections;

(g) The combination of (f), wherein the second therapeutic agent is an azole, a polyene, a purine or pyrimidine nucleotide inhibitor, a pneumocandin or echinocandin derivative, a protein elongation factor inhibitor, a chitin inhibitor, a mannan inhibitor, a bactericidal/permeability-inducing (BPI) protein product, or an immunomodulating agent;

(h) The combination of (g), wherein the second therapeutic agent is itraconazole, ketoconazole, miconazole, fluconazole, voriconazole, posaconazole, amphotericin B, flucytosine, anidulafungin, micafungin, or caspofungin;

(i) A method of inhibiting (1,3)-β-D-glucan synthase in a subject in need thereof comprising administering to the subject an effective amount of a compound of Formula (I) or (Ia);

(j) A method of treating or preventing mycotic infections in a subject in need thereof comprising administering to the subject an effective amount of a compound of Formula (I) or (Ia);

(k) The method of (j), wherein the compound of Formula (I) or (Ia), is administered in combination, either sequentially or concurrently, with a second therapeutic agent effective against fungal/bacterial infections;

(l) The method of (k), wherein the second therapeutic agent is an azole, a polyene, a purine or pyrimidine nucleotide inhibitor, a pneumocandin or echinocandin derivative, a protein elongation factor inhibitor, a chitin inhibitor, a mannan inhibitor, a bactericidal/permeability-inducing (BPI) protein product, or an immunomodulating agent;

(m) The method of (l), wherein the second therapeutic agent is itraconazole, ketoconazole, miconazole, fluconazole, voriconazole, posaconazole, amphotericin B, flucytosine, anidulafungin, micafungin, or caspofungin;

(n) A method of inhibiting (1,3)-β-D-glucan synthase in a subject in need thereof comprising administering to the subject a pharmaceutical composition of (b), (c), (d), or (e) or the combination of (f), (g) or (h); and (o) A method of treating or preventing mycotic infections in a subject in need thereof comprising administering to the subject a pharmaceutical composition of (b), (c), (d), or (e) or the combination of (f), (g) or (h).

The present invention also includes a compound of the present invention (i) for use in, (ii) for use as a medicament for, or (iii) for use in the preparation of a medicament for: (a) inhibiting (1,3)-β-D-glucan synthase in a subject in need thereof, or (b) treating or preventing mycotic infections. In these uses, the compounds of the present invention can optionally be employed in combination, either sequentially or concurrently, with one or more therapeutic agents effective against fungal/bacterial infections.

In the embodiments of the compound as provided above, it is to be understood that each embodiment may be combined with one or more other embodiments, to the extent that such a combination provides a stable compound and is consistent with the description of the embodiments. It is further to be understood that the embodiments of compositions and methods provided as (a) through (o) above are understood to include all embodiments of the compounds, including such embodiments as result from combinations of embodiments of the compound.

In addition, it is understood that, in the description of embodiments of the compounds as set forth above, indicated substitutions are included only to the extent that the substitutents provide stable compounds consistent with the definition. For example, in embodiments in which $R^6$ is OH, $R^6$ will not be substituted by any $R^7$ groups, but in embodiments in which $R^6$ is $(C_1-C_{12})$alkyl, $R^6$ may be substituted by 0, 1, or from 2 to 13 independently selected $R^7$ groups.

Additional embodiments of the invention include the pharmaceutical compositions, combinations and methods set forth in (a)-(o) above and the uses set forth in the preceding paragraph, wherein the compound of the present invention employed therein is a compound of one of the embodiments or aspects of the compounds described above. In all of these embodiments as well as those described hereinbelow, the compound may optionally be used in the form of a pharmaceutically acceptable salt or hydrate when appropriate. The present compounds (including pharmaceutical acceptable salt and/or hydrate forms) have or are expected to have antimicrobial (e.g., antifungal) activities against yeasts and fungi, including *Acremonium, Absidia* (e.g., *Absidia corymbifera*), *Alternaria, Aspergillus* (e.g., *Aspergillus clavatus, Aspergillus flavus, Aspergillus fumigatus, Aspergillus nidulans, Aspergillus niger, Aspergillus terreus*, and *Aspergillus versicolor*), *Bipolaris, Blastomyces* (e.g., *Blastomyces dermatitidis*), *Blastoschizomyces* (e.g., *Blastoschizomyces capitatus*), *Candida* (e.g., *Candida albicans, Candida glabrata* (*Torulopsis glabrata*), *Candida guilliermondii, Candida kefyr, Candida krusei, Candida lusitaniae, Candida parapsilosis, Candida pseudotropicalis, Candida stellatoidea, Candida tropicalis, Candida utilis, Candida lipolytica, Candida famata* and *Candida rugosa*), *Cladosporium* (e.g., *Cladosporium carrionii* and *Cladosporium trichloides*), *Coccidioides* (e.g., *Coccidioides immitis*), *Cryptococcus* (e.g., *Cryptococcus neoformans*), *Curvularia, Cunninghamella* (e.g., *Cunninghamella elegans*), *Dermatophyte, Exophiala* (e.g., *Exophiala dermatitidis* and *Exophiala spinifera*), *Epidermophyton* (e.g., *Epidermophyton floccosum*), *Fonsecaea* (e.g., *Fonsecaea pedrosoi*), *Fusarium* (e.g., *Fusarium solani*), *Geotrichum* (e.g., *Geotrichum candiddum* and *Geotrichum clavatum*), *Histoplasma* (e.g., *Histoplasma capsulatum* var. *capsulatum*), *Malassezia* (e.g., *Malassezia furfur*),

*Microsporum* (e.g., *Microsporum canis* and *Microsporum gypseum*), *Mucor, Paracoccidioides* (e.g., *Paracoccidioides brasiliensis*), *Penicillium* (e.g., *Penicillium marneffei*), *Phialophora, Pityrosporum ovale, Pneumocystis* (e.g., *Pneumocystis carinii*), *Pseudallescheria* (e.g., *Pseudallescheria boydii*), *Rhizopus* (e.g., *Rhizopus microsporus* var. *rhizopodiformis* and *Rhizopus oryzae*), *Saccharomyces* (e.g., *Saccharomyces cerevisiae*), *Scedosporium* (e.g., *Scedosporium apiosperum*), *Scopulariopsis, Sporothrix* (e.g., *Sporothrix schenckii*), *Trichoderma, Trichophyton* (e.g., *Trichophyton mentagrophytes* and *Trichophyton rubrum*), and *Trichosporon* (e.g., *Trichosporon asahii, Trichosporon beigelii* and *Trichosporon cutaneum*). The present compounds may also be used to treat infections caused by protozoa such as *Toxoplasma, Cryptosporidium, Leishmania, Tripanosoma, Giardia* and *Trichomonas*. The present compounds are not only useful against organisms causing systemic human pathogenic mycotic infections, but also useful against organisms causing superficial fungal infections such as *Trichoderma* sp. and other *Candida* spp. The compounds of the present invention are particularly effective against *Aspergillus flavus, Aspergillus fumigatus, Candida albicans, Candida parapsilosis, Cryptococcus neoformans, Saccharomyces cerevisiae*, and *Trichophyton mentagrophytes*.

In view of their antifungal activity, compounds of Formula (I) are useful for the treatment and/or prevention of a variety of superficial, cutaneous, subcutaneous and systemic mycotic infections in skin, eye, hair, nail, oral mucosa, gastrointestinal tract, bronchus, lung, endocardium, brain, meninges, urinary organ, vaginal portion, oral cavity, ophthalmus, systemic, kidney, bronchus, heart, external auditory canal, bone, nasal cavity, paranasal cavity, spleen, liver, hypodermal tissue, lymph duct, gastrointestine, articulation, muscle, tendon, interstitial plasma cell in lung, blood, and so on.

Therefore, compounds of the present invention are useful for preventing and treating various infectious diseases, such as dermatophytosis (e.g., trichophytosis, ringworm or tinea infections), athletes foot, paronychia, pityriasis versicolor, erythrasma, intertrigo, fungal diaper rash, candida vulvitis, candida balanitis, otitis externa, candidiasis (cutaneous and mucocutaneous), chronic mucocandidiasis (e.g. thrush and vaginal candidiasis), cryptococcosis, geotrichosis, trichosporosis, aspergillosis, penicilliosis, fusariosis, zygomycosis, sporotrichosis, chromomycosis, coccidioidomycosis, histoplasmosis, blastomycosis, paracoccidioidomycosis, pseudallescheriosis, mycetoma, mycotic keratitis, otomycosis, pneumocystosis, and fungemia. The present compounds may also be used as prophylactic agents to prevent systemic and topical fungal infections. Use as prophylactic agents may, for example, be appropriate as part of a selective gut decontamination regimen in the prevention of infection in immunocompromised patients (e.g. AIDS patients, patients receiving cancer therapy or transplant patients). Prevention of fungal overgrowth during antibiotic treatment may also be desirable in some disease syndromes or iatrogenic states.

Examples of azoles that may be used in combination with the present compounds include, but are not limited to, fluconazole, voriconazole, itraconazole, ketoconazole, miconazole, ravuconazole, detoconazole, clotrimazole, and posaconazole. Examples of polyenes that may be used in combination with the present compounds include, but are not limited to, amphotericin B, nystatin, liposamal and lipid forms thereof such as ABELCET, AMBISOME, and AMPHOCIL. Examples of purine or pyrimidine nucleotide inhibitors that may be used in combination with the present compounds include, but are not limited to, flucytosine or polyxins such as nikkomycines, in particular nikkomycine Z or nikkomycine X. Another class of therapeutic agents that may be used in combination with the present compounds includes chitin inhibitors. Examples of elongation factor inhibitors that may be used in combination with the present compounds include, but are not limited to, sordarin and analogs thereof. Examples of pneumocandin or echinocandin derivatives that may be used in combination with the present compounds include, but are not limited to, cilofungin, anidulafungin, micafungin, and caspofungin. Examples of mannan inhibitors that may be used in combination with the present compounds include but are not limited to predamycin. Examples of bactericidal/permeability-inducing (BPI) protein products that may be used in combination with the present compounds include but are not limited to XMP.97 and XMP.127. Examples of immunomodulators that may be used in combination with the present compounds include, but are not limited to, an interferon, (e.g., IL-1, IL-2, IL-3 and IL-8), defensines, tacrolimus and G-CSF (Granulocyte-colony stimulating factor).

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to all of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl.

The term "alkoxy" refers to an —O-alkyl group wherein alkyl is as defined above.

The term "cycloalkyl" refers to any cyclic ring of an alkane having a number of carbon atoms in the specified range. Thus, for example, "$C_{3-6}$ cycloalkyl" (or "$C_3$-$C_6$ cycloalkyl") refers to cyclopropyl, cyclobutyl, cyclopentyl, and cyclohexyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms have been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. Suitable haloalkyls include the series $(CH_2)_{0-5}CF_3$ (i.e., trifluoromethyl, 2,2,2-trifluoroethyl, 3,3,3-trifluoro-n-propyl, etc.).

The term "silylalkyl" refers to an alkyl group as defined above in which one or more of the carbon atoms have been replaced with a silicon atom.

As used herein, the term "or," as used herein, denotes alternatives that may, where appropriate, be combined; that is, the term "or" includes each listed alternative separately as well as their combination.

Unless expressly stated to the contrary, all ranges cited herein are inclusive. For example, a heterocyclic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, and so forth.

Any of the various cycloalkyl and heterocyclic/heteroaryl rings and ring systems defined herein may be attached to the rest of the compound at any ring atom (i.e., any carbon atom or any heteroatom) provided that a stable compound results. Suitable 5- or 6-membered heteroaromatic rings include, but are not limited to, pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl. Suitable 3- to 6-membered heterocyclyls include, but are not limited to, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, thiadiazepanyl, dithiazepanyl, azepanyl, diazepanyl, thiadiazinanyl, tetrahydropyranyl, tetrahydrothiopyranyl, and dioxanyl.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

As a result of the selection of substituents and substituent patterns, certain of the compounds of the present invention can have asymmetric centers and can occur as mixtures of stereoisomers, or as individual diastereomers, or enantiomers. Unless otherwise indicated, all isomeric forms of these compounds, whether isolated or in mixtures, are within the scope of the present invention. Also included within the scope of the present invention are tautomeric forms of the present compounds as depicted.

When any variable occurs more than one time in any constituent or in Formula (I) or in any other formula depicting and describing compounds of the invention, its definition on each occurrence is independent of its definition at every other occurrence. Also, combinations of substituents and/or variables are permissible only if such combinations result in stable compounds.

The term "substituted" includes mono- and poly-substitution by a named substituent to the extent such single and multiple substitution (including multiple substitution at the same site) is chemically allowed. Unless expressly stated to the contrary, substitution by a named substituent is permitted on any atom in a ring (e.g., an aryl, a cycloalkyl, a heteroaryl, or a heterocyclyl) provided such ring substitution is chemically allowed and results in a stable compound.

The compounds of this invention are also useful in the preparation and execution of screening assays for antifungal compounds. For example, the compounds of this invention are useful for isolating mutants, which are excellent screening tools for more powerful antifungal compounds.

All compounds of the present invention may be administered in the form of pharmaceutically acceptable salts or hydrates as appropriate. The term "pharmaceutically acceptable salt" refers to a salt which possesses the approximate effectiveness of the parent compound and which is suitable for administration to a patient. Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, and benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administering" a compound) in reference to a compound of the invention mean providing the compound or a prodrug of the compound to the subject in need of treatment. When a compound of the invention or a prodrug thereof is provided in combination with one or more other active agents (e.g., other antifungal/antibacterial agents useful for treating fungal/bacterial infections), "administration" and its variants are each understood to include concurrent and sequential provision of the compound or prodrug and other agents.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented or for reducing the likelihood of occurrence. The term also includes herein the amount of active compound sufficient to inhibit (1,3)-β-D-glucan synthase and thereby elicit the response being sought (i.e., an "inhibition effective amount"). When the active compound (i.e., active ingredient) is administered as the salt, references to the amount of active ingredient are to the free acid or free base form of the compound.

For the purpose of inhibiting (1,3)-β-D-glucan synthase or preventing or treating fungal infection, the compounds of the present invention, optionally in the form of a salt or a hydrate, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation (e.g., nasal or buccal inhalation spray, aerosols from metered dose inhalator, and dry powder inhalator), by nebulizer, ocularly, topically, transdermally, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences,* 19$^{th}$ edition, edited by A. R. Gennaro, Mack Publishing Co., 1995.

The compounds of this invention can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention also includes processes for making compounds of Formula (I). The compounds of the present invention may be prepared according to the following reaction schemes and examples, or modifications thereof, from starting material enfumafungin. Enfumafungin is a natural product produced from a fungus strain of *Hormonema* sp. (deposited under the Budapest Treaty in the culture collection of the American Type Culture Collection and assigned accession number ATCC 74360) that was isolated from living leaves of an unidentified shrub collected in Navalquejigo, province of Madrid, Spain, as described in U.S. Pat. No. 5,756,472, content of which is incorporated by reference in its entirety.

General Schemes

Three key intermediates were utilized in the preparation of compounds of the present invention. Scheme A illustrates a preparation of I-1, I-2 and I-3.

Intermediate I-1 was prepared by first reduction of the C25-hydroxy group of enfumafungin to the methylene group by treatment of enfumafungin with triethylsilane under acidic conditions. Next, the C18 carboxyl group was protected by benzylation and the 3-glucose group was hydrolyzed under acidic conditions to provide I-1.

A more robust protecting group at the 2-position, namely a C2-methoxy, was introduced by first reducing enfumafungin as described above, methanolyzing the C2-acetate and C3-glucosyl moieties using sulfuric acid and methanol and finally protecting the C18-carboxyl by benzylation to give I-2.

Intermediate I-3, which possesses a C-12 keto group, was prepared from I-1 by first protecting the C3-hydroxyl as an acetate, hydrogenolyzing the C18 benzyl ester, oxidizing the C12-methylene with chromium trioxide and dimethylpyrazole, reprotecting the C18 carboxylic acid as a benzyl ester and finally ensuring that an acetoxy group is present at the 2-position by treatment with sulfuric and acetic acids.

Scheme A

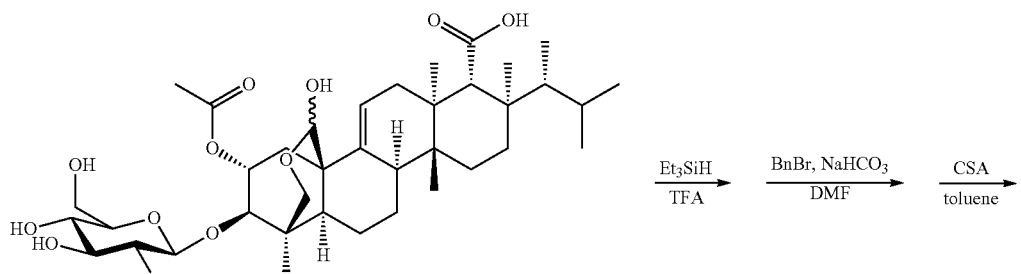

enfumafungin

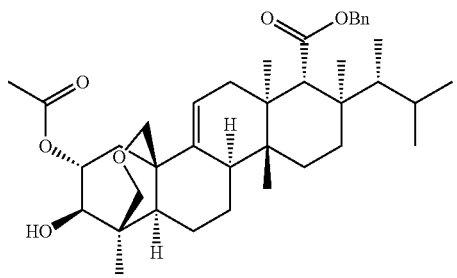

I-1

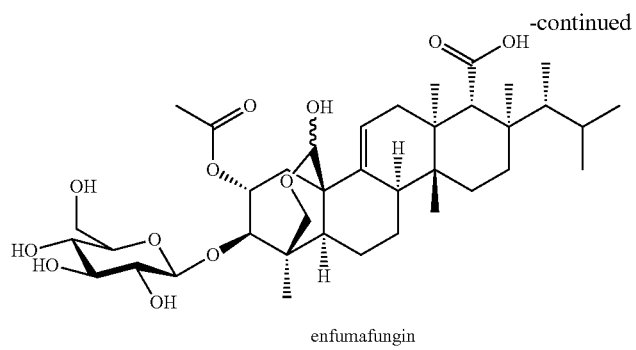

enfumafungin

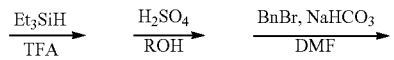

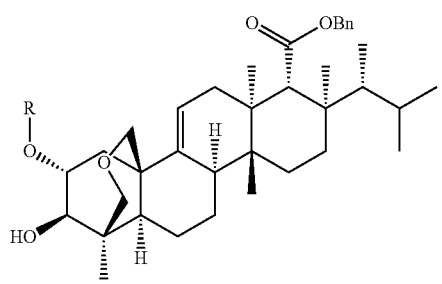

I-2 (R = Me)

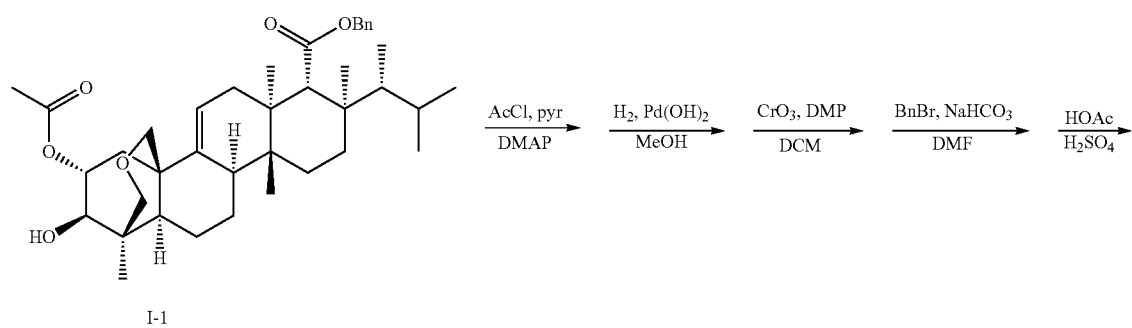

I-1

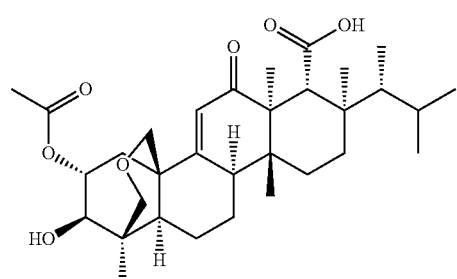

I-3

The 3-hydroxyl group of either I-1, I-2 or I-3 may be acylated as shown below in Schemes B through F. Any suitable acylating agents and conditions can be used and applied as known by those who are skilled in the art. The following examples are meant to be illustrative and not limiting.

Additional manipulations to intermediates not explicitly depicted below may be carried out such as oxidations, selective reductions, alkylations, acylations, deprotections, guanidylations, cyanations, microbial transformations and sulfenylations, for example, to obtain a variety of functionalized ester groups at the 3-position of the enfumafungin core. These manipulations are easily carried out by those skilled in the art.

Scheme B
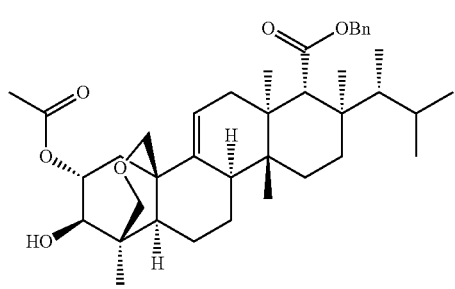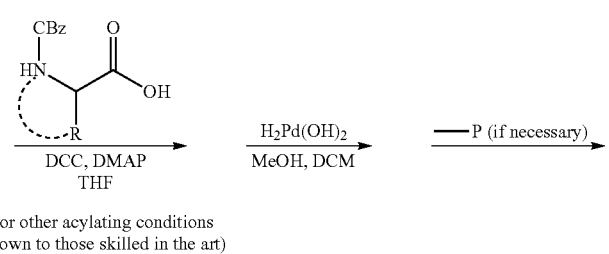
I-1
Examples 1-73
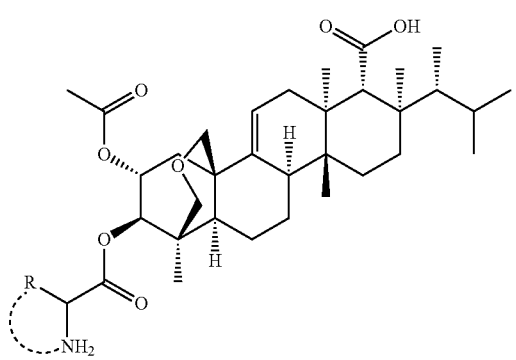
The R group and amine may be tethered in a ring.
Scheme C
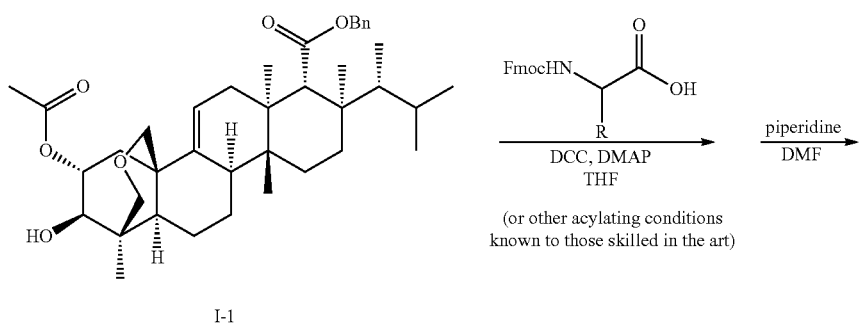
I-1
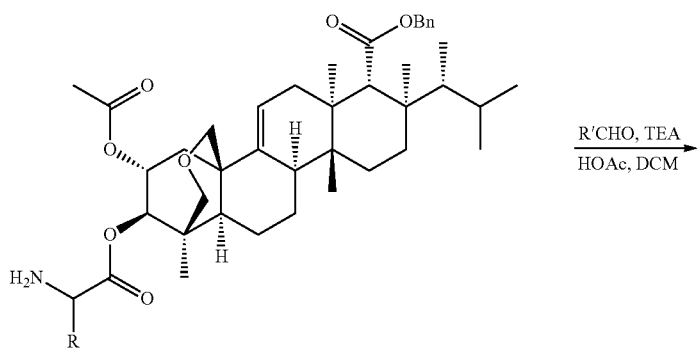
(R = H, Ex 74)

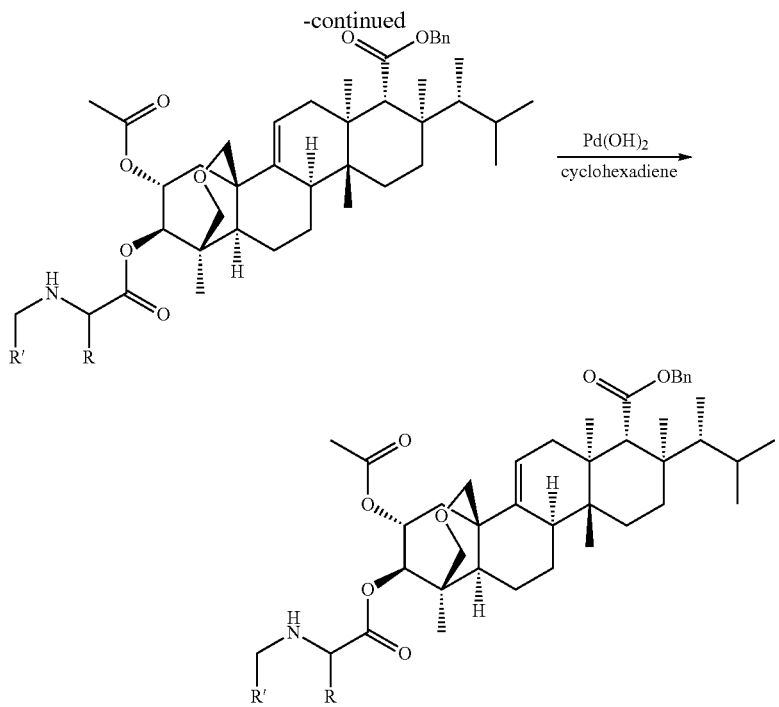
Examples 75-86
The amino group may be alkylated by methods known to those skilled in the art.
Scheme D
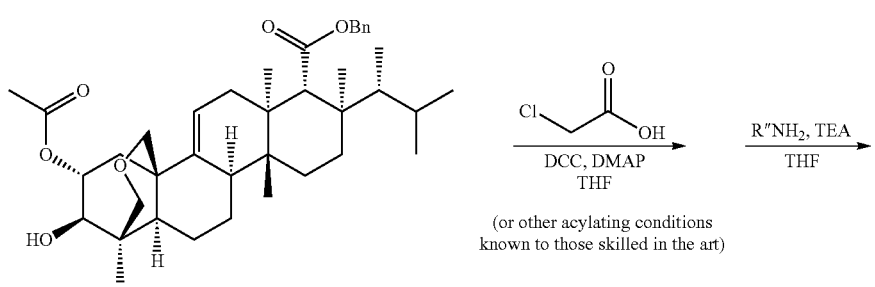
(or other acylating conditions known to those skilled in the art)
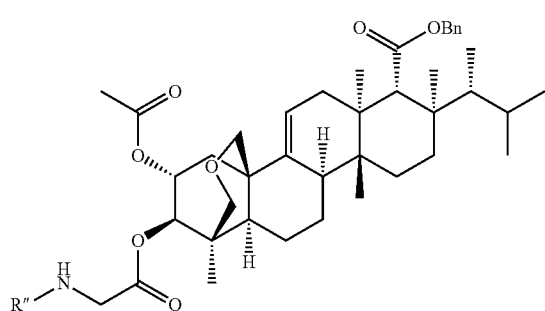
Examples 88-127

Amine groups may be introduced by reacting an amine with a reactive chloroacetyl ester intermediate.
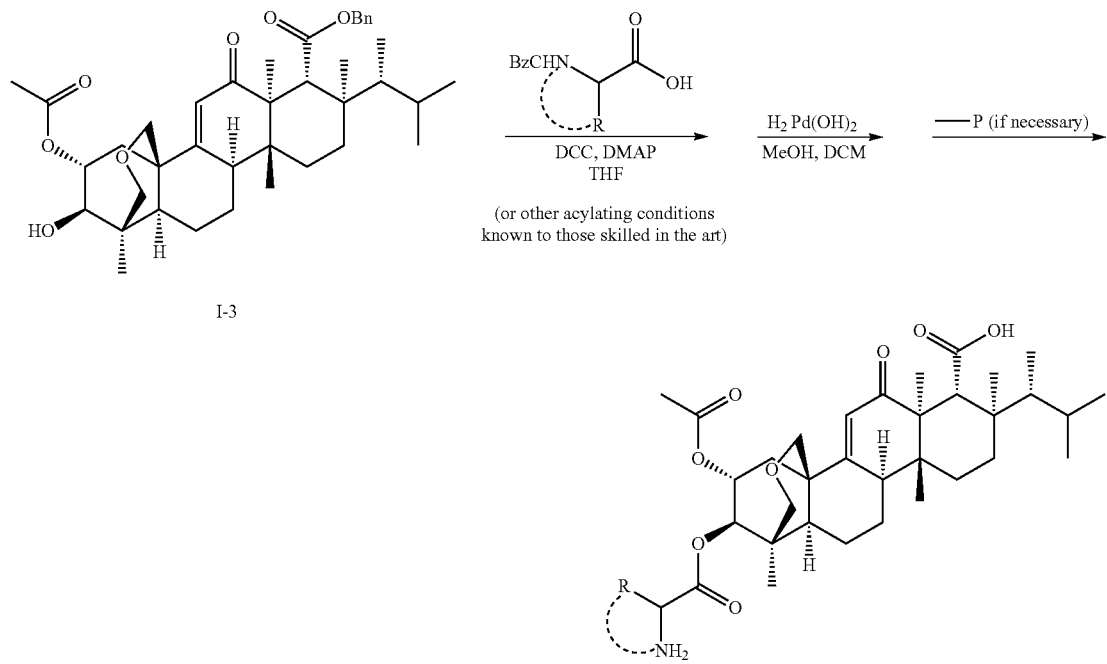
Examples 128-135
The R group and amine may be tethered in a ring.
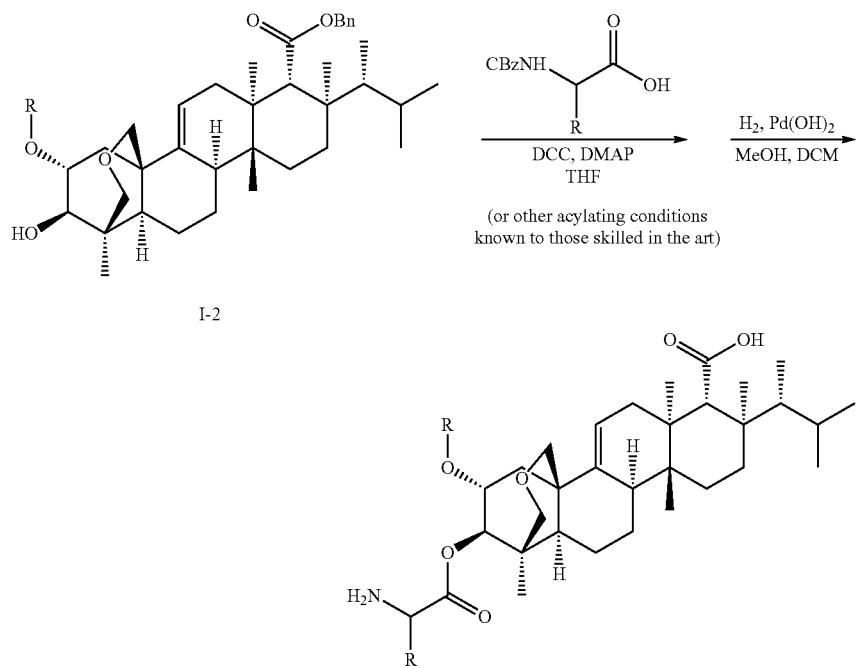
R = Me Example 136
R = Et Example 137
R = 2-Pr Example 138

Utilizing alcohols other than methanol in the preparation of I-2 allows the introduction of other alkyl groups at the 2-position of the enfumafungin core. For example, R=ethyl is obtained using ethanol and R=2-propyl is obtained using isopropanol.

The antifungal activity of the present compounds can be demonstrated by various assays known in the art, for example, by their glucan synthesis inhibitory acticity ($IC_{50}$), minimum inhibitory concentration (MIC-100) or minimum prominent inhibition (MIC-80) against yeasts and minimum effective concentration (MEC) against filamentous moulds and dermatophytes in a broth microdilution assay, or in vivo anti-*Candida* activity in a mouse (TOKA). Compounds of the present invention were found to inhibit the growth of *Candida* spp. in the range of <0.03-32 µg/mL or to give an MEC against *Aspergillus fumigatus* in the range of <0.03-32 µg/mL.

Glucan Synthase Inhibition

The in vitro evaluation of glucan synthase inhibitory activity of compounds was measured in a polymerization assay in 96-well format. Each well contained 100 µL of $^3$H-UDPG at 0.5 mM (6000 to 8000 dpm/nmol), 50 mM HEPES pH 7.5 (Sigma), 10% w/v glycerol (Sigma), 1.5 mg/mL bovine serum albumin (Sigma A 9647. Lot 44H0190), 25 mM KF (Fisher), 1 mM EDTA (Gibco ULTRAPURE), 25 µM GTP-γ-S, enzyme sufficient to give 3 to 6 nmoles incorporation during the 60 min incubation at 22° C., and test compound added from wells in 3-fold serial dilutions in 100% DMSO (1 µL/well). The reaction was stopped by the addition of 100 µL of 20% trichloroacetic acid. Plates were chilled for a minimum of 10 min, and precipitated glucan collected by filtration on GF/C plates (Packard UNIFILTER®-96), washed with 5 cycles of water (about 1 mL/well each cycle) using a Packard FILTERMATE HARVESTER. 40 µL/well scintillation fluid (Packard ULTIMA GOLD TM-XR) was added and the sealed plates counted in a WALLAC BETA counter in top-counting mode at an efficiency of approximately 40%.

Stock solutions were stored at 10 mg/mL in DMSO at −20° C. For each new enzyme preparation, the initial titration performed started at 1 mg/mL, which was prepared by making a 10-fold dilution in DMSO (5 µL to 50 µL). 40 µL of this stock was placed in column 12 of a round-bottomed 96-well microtiter plate. 40 µL DMSO was added to columns 1 to 11 in the same row and ten 3-fold serial dilutions performed, by transferring 20 µL from column 12 to column 11 etc., with 4 mixings before each transfer. No test compound was transferred to from column 2 to column 1. Duplicate aliquots of 1 µL of all 12 dilutions were then transferred to the side walls of a 96-well Bioblock 1.1 mL plate (Fisherbrand) to create two rows.

The results were tabulated and a standard plate background was subtracted and the net count transpose-pasted into a PRISM file, with final compound concentrations used in ng/mL. Graphs were created in PRISM software, using the average of two determinations, and using PRISM's curve fitting program (sigmoidal dose response non-linear regression).

Routine analysis was performed with glucan synthase (GS) prepared from *Candida albicans* MY1055 by the following procedure: MY1055 was grown in 10 liters YPD medium (10 g yeast extract, 20 g tryptone, 20 g glucose per liter) with vigorous shaking at 30° C., to early stationary phase. Cells were harvested by centrifugation, the pellet was washed and frozen at −70° C. until breakage. Thawed pellets were shaken with an equal volume of breakage buffer (50 mM HEPES pH 7.4, 10% glycerol, 1 mM EDTA, 1 mM PMSF, 1 mM DTT) and 4 times their weight of 0.5 mm acid washed glass beads for 2 hours at 4° C. Extent of breakage was assessed visually at 40× magnification. For *C. parapsilosis* strains, shaking was extended to 3 hours to maximize breakage. After low speed centrifugation to remove cell debris, the supernatant was centrifuged at 100,000×g for 60 min. to separate membranes plus ribosomes from cytoplasmic components. Membranes were further washed two additional times with breakage buffer using the same centrifugation conditions and finally suspended in breakage buffer at 25 to 30 mg/mL protein (Biorad) for storage at −70° C. Extraction of GS activity from membranes was performed at a protein concentration of 5 mg/mL in extraction buffer (50 mM $NaPO_4$ pH 7.5, 0.1 M KCl, 0.1M Na citrate, 20% glycerol, 5 µM GTP-γ-S, 1 mM DTT, 1 mM PMSF, 3 µg/mL pepstatin) plus 0.25% W1 by gentle mixing at 4° C. for 60 min, followed by centrifugation at 100,000×g for 60 min. After centrifugation, clear supernatant was removed from a pellet consisting of a hard layer usually with small amounts of gelatinous unextracted membranes above it.

Trapping was initiated immediately by 5-fold dilution in trapping buffer (50 mM HEPES pH 7.5, 10 mM KF, 1 mM EDTA, 2 mg/mL BSA) plus 2.5 mM UDPG and 10 µM GTP-γ-S. After incubation at 25° C. for 60 to 90 minutes, glucan was harvested by low speed centrifugation (3,000×g, 10 min). The soft pellet was washed 3 times with wash buffer (50 mM HEPES, 20% glycerol, 1mM EDTA) plus 2.5 mM UDPG and 5 µM GTP-γ-S, once without UDPG, and suspended in about 5 volumes of PE extraction buffer (50 mM HEPES, 30% glycerol, 1 mM EDTA, 20 µM GTP-γ-S, 0.4% CHAPS, 0.08% cholesterol hemisuccinate) using a DOUNCE homogenizer. The suspension was frozen overnight at −70° C., and then sedimented at 100,000×g for 10 min.

Susceptibility Testing

To each well of a 96-well plate 100 µL of appropriate test medium (example: RPMI-1640 containing 0.165 molar MOPS+3 g/L glutamine w/o sodium bicarbonate or RPMI-1640 containing 0.165 molar MOPS+3 g/L glutamine w/o sodium bicarbonate with 3.2% DMSO or 2× RPMI-1640 containing 0.33 molar MOPS+6 g/L glutamine w/o sodium bicarbonate with 6.4% DMSO for the plates with final concentration of 50% serum) was added.

The test compound was dissolved at concentration of 10 mg/mL in DMSO and diluted 1:78 into appropriate test medium with no DMSO or 1.92% DMSO or 5.12% DMSO. Example: added 25 µL of 10 mg/ml compound stock solution to 1925 µL of RPMI-1640 containing 0.165 molar MOPS+3 g/L glutamine w/o sodium bicarbonate with 1.92% DMSO. The test compound concentration achieved was 128 µg/ml and DMSO concentration of 3.2%. To the first well of each row of appropriate test medium plate 100 µL of the compound stock solutions (128 µg/mL) were added. Compounds were serially diluted two-fold across the plate to column 11 (column 12 was the growth control well) and the last 100 µL was discarded yielding compound concentrations of 64 to 0.06 µg/mL. For plates with dermatophytes the last 100 µL were placed in the first row of a second plate and serial diluted two-fold and yielding compound concentrations of 64-0.00004 µg/mL. Amphotericin B and caspofungin, the control compounds, were prepared as a stock solution of 10 mg/mL in DMSO and prepared in micro-titer plate as stated above for test compounds.

Yeasts

In the microbroth dilution assay for yeasts, microorganisms *Candida* spp., *Cryptococcus neoformans* (MY2062) and *Saccharomyces cerevisiae* (MY2255) were selected by streaking a yeast culture on SABOURAUD Dextrose Agar (SDA) incubating for 24-48 hours at 35-37° C., thereafter selecting 1 characteristic colony and transferring to a fresh plate and incubating under same conditions. From the regrowth, 3 to 5 colonies were selected and suspended in 5-mL of sterile normal saline (BBL) and adjusted to match the turbidity of a 0.5 McFarland standard using DADE/BEHRING turbidity meter (preferred OD of 0.06 to 0.12). This resulted in a concentration of approximately 1-5×106 CFU/mL. The inocula were further diluted 1:1000 into RPMI-1640 containing 0.165 molar MOPS+3 g/L glutamine w/o sodium bicarbonate with 3.2% DMSO. Assay plates previously titrated with test compound in RPMI-1640 containing 0.165 molar MOPS+3 g/L glutamine w/o sodium bicarbonate with 3.2% DMSO were then inoculated with 100 μL/well of this dilution of culture. This resulted in a final organism concentration of $5 \times 10^2$ to $2.5 \times 10^3$ CFU/mL and final compound concentrations of 32 to 0.03 μg/mL. In addition *C. albicans* (MY1055) was also tested with heat inactivated (1 hour at 55° C.) mouse serum which was filtered twice using 0.22 micron GP EXPRESS PLUS MILLIPORE filtration system. This standardized suspension was diluted 1:1000 into mouse serum. Assay plates previously titrated with drug in 2× RPMI-1640 containing 0.33 molar MOPS+6 g/l glutamine w/o sodium bicarbonate with 6.4% DMSO were then inoculated with 100 μl/well of this dilution of culture. This resulted in a final organism concentration of $5 \times 10^2$ to $2.5 \times 10^3$ CFU/mL and final compound concentration of 32 to 0.03 μg/ml and 50% mouse serum. Plates were incubated at 35-37° C. and MICs were read at 24 hours for *Candida* and 48 hours for *Cryptococcus neoformans*.

Filamentous Fungi

In the microbroth dilution assay for filamentous fungi *Aspergillus fumigatus* (MF5668) and dermatophyte *Trichophyton mentagrophytes* (MF7004) these microorganisms were grown on Sabouraud Dextrose Agar (SDA) slants at 35-37° C. for *Aspergillus fumigatus* and at 30° C. for *Trichophyton mentagrophytes* for 7 days prior to use. Inocula for filamentous fungi were prepared by adding 5 mL of sterile normal saline to slant followed by gently scraping the surface of stock slants growth with a sterile DACRON swab suspending the spores (conidia) in saline. Each spore suspension was then transferred to another tube and adjusted to match the turbidity of a 0.5 McFarland standard using the DADE/BEHRING turbidity meter (preferred OD of 0.06-0.09) for *A. fumigatus* and (preferred OD of 0.13-0.17) for dermatophyte *T. mentagrophytes*. This resulted in a concentration of approximately 1-5×10⁶ CFU/mL. A spore count was performed on each culture suspension with a hemocytometer to insure the correct inoculum. This standardized suspension for *A. fumigatus* was diluted 1:500 in RPMI-1640 containing 0.165 molar MOPS+3 g/L glutamine w/o sodium bicarbonate with 3.2% DMSO. This standardized suspension for *T. mentagrophytes* was diluted 1:500 in RPMI-1640 containing 0.165 molar MOPS+3 g/L glutamine w/o sodium bicarbonate. Assay plates previously titrated with test compound in either RPMI-1640 containing 0.165 molar MOPS+3 g/L glutamine w/o sodium bicarbonate with 3.2% DMSO or RPMI-1640 containing 0.165 molar MOPS+3 g/L glutamine w/o sodium bicarbonate were then inoculated with 100 μL/well of this dilution. In addition *A. fumigatus* (MF5668) was also tested with heat inactivated human serum which was filtered once using 0.22 micron GP EXPRESS PLUS MILLIPORE filtration system. This standardized suspension was diluted 1:500 in human serum. Assay plates previously titrated with test compound in 2× RPMI-1640 containing 0.33 molar MOPS+6 g/L glutamine w/o sodium bicarbonate were then inoculated with 100 μL/well of this dilution of culture. Plates were incubated at 35° C. and MICs were read at 48 hours for *Aspergillus fumigatus*, and plates incubated at 30° C. and MICs were read at 96 hours for Dermatophyte *T. mentagrophytes*.

In the above testing, viable cell counts were performed on 0.5 McFarland samples to verify the CFU/mL. Serial dilutions (1:10) with the 0.5 McFarland were made in saline. One-hundred micro-liters of each dilution ($10^4$, $10^5$, $10^6$) was spread onto a SABOURAUD Dextrose Agar (SDA) plates which were then incubated for 24 to 48 or 96 (dermatophytes) hours at 35° C. or 30° C. After incubation colonies were counted and recorded. Growth and sterility controls for each organism were also carried out. Column 12 was the growth control and contains no test compound. Row H was not inoculated with organism or test compound and was used as sterility control for each plate.

The minimum inhibitory concentration (MIC-100) for all test compounds is determined to be the lowest concentration of compound at which there was no visible growth as compared to growth control without test compound. The minimum prominent inhibition (MIC-80) in growth is indicated as 80% inhibition in growth compared to growth control without test compound. For *Aspergillus* and dermatophyte *T. mentagrophytes* minimum effective concentration (MEC) was determined as narly morphology of hyphae both macroscopic and microscopic.

In Vivo Anti-Candida Activity

A disseminated Candida infection is induced in DBA/2 mice by the I.V. inoculation of 0.2 mL of a yeast cell suspension containing $3.0 \times 10^4$ CFU of *C. albicans* MY1055 into their lateral tail vein. Therapy is initiated within 15 to 30 minutes after challenge. Mice are treated with test compound either 1) I.P., b.i.d. for a total of 2 days or 2) P.O., b.i.d. for a total of 2 days. For each route of administration and diluent, an appropriate sham-treated control group is included.

Kidneys from euthanized mice (4-5/group) are removed four days after challenge using aseptic techniques, weighed and placed in sterile WHIRL PAK bags containing 5 mL sterile saline. Kidneys are homogenized in the bags, serially diluted in saline and aliquots are plated on SDA. Plates are incubated at 35° C. and enumerated after 30 to 48 hours for *C. albicans* CFUs. Means from CFU/g of paired kidneys of treated groups are compared to the means from sham-treated controls. Percent sterilization is indicated by the number of mice with no detectable yeast, where the limit of detection because of the dilution scheme, is 50 yeast cells per pair of kidneys. For data from individual mice where no detectable yeast are recovered from paired kidneys, 9.8 is entered into the MICROSOFT EXCEL spread sheets formula [Log 10 ((5×raw count)/paired kidney weight)] so that the counts would be one less than the limit of detection (49 cells per pair of kidneys).

Mean log 10 yeast CFU/g of paired kidneys are compared to the sham treated controls using Student's t-test (two tailed, unpaired) on MICROSOFT EXCEL. Comparisons are deemed significant at the p=0.05 level. Mean percent reduction in CFU/g of paired kidneys for treated groups at 4 days following challenge relative to control are computed. A linear trend is typically evident when dose and CFU are both expressed in log 10 scale. Inverse regression (2) is subsequently used to estimate $ED_{90}$ and $ED_{99}$ values, defined as the doses (mg/kg) that reduced the number of CFU per organ by 90 and 99%, respectively.

Compounds of the present invention generally have GS $IC_{50}$s less than 500 ng/mL and MIC-100s against one or more organisms of <0.03-32 μg/mL; however, some compounds may have an $IC_{50}$ in the range of from about 500 to more than 10,000 ng/mL. Compounds of the present invention generally have MIC-80s in the range of <0.03-32 μg/mL and MECs of <0.03-32 μg/mL. As for activity in the disseminated Candida infection, useful compounds will lower the CFU/g in kidneys by greater than 1 log 10 unit compared to sham treated controls and compounds that lower CFU/g by 2 log 10 units are especially useful.

The following examples serve only to illustrate the invention and its practice. The examples are not to be construed as limitations on the scope or spirit of the invention.

| Abbreviations | |
| --- | --- |
| AcCl | Acetyl chloride |
| Boc | t-Butyloxycarbonyl |
| Cbz | Benzyloxycarbonyl (also CBz) |
| CDCl₃ | Deuterio-trichloromethane |
| CH₃CN | Acetonitrile |
| DCC | Dicyclohexylcarbodiimide |
| DCE | Dichloroethane |
| DCM | Dichloromethane |
| DMAP | 4-Dimethylaminopyridine |
| DMF | Dimethylformamide |
| Et | Ethyl |
| EtOAc | Ethyl acetate |
| EtOH | Ethanol |
| Gly | Glycine residue |
| Et₃SiH | Triethylsilane |
| Fmoc | Fluorenylmethyloxycarbonyl |
| H₂ | Hydrogen or hydrogen atomosphere |
| H₂O | Water |
| Hyp | Hydroxyproline residue |
| HOAc | Acetic acid |
| H₂SO₄ | Sulfuric acid |
| HCl | Hydrochloric acid |
| K₂CO₃ | Potassium carbonate |
| Lys | Lysine residue |
| Me | Methyl |
| MeOH | Methanol |
| NaCl | Sodium chloride |
| NaHCO₃ | Sodium bicarbonate |
| NH₄Cl | Ammonium chloride |
| NH₄OH | Ammonium hydroxide |
| Na₂SO₄ | Sodium sulfate |
| PdOH | Palladium hydroxide |
| RT | Room temperature, approximately 25° C. |
| SiO₂ | Silica |
| TEA | Triethylamine |
| TFA | Trifluoroacetic acid |
| THF | Tetrahydofuran |
| TLC | Thin layer chromatography |
| Val | Valine residue |

EXAMPLES

INTERMEDIATES

Intermediate 1: Benzyl(1S,2R,3R,4aR,6aS,7R,8R,10aR,10bR,12aR)-3-(acetyloxy)-8-[(1R)-1,2-dimethylpropyl]-2-hydroxy-1,6a,8,10a-tetramethyl-1,3,4,6,6a,7,8,9,10,10a,10b,11,12,12a-tetradecahydro-2H-1,4a-(methanooxymethano)chrysene-7-carboxylate

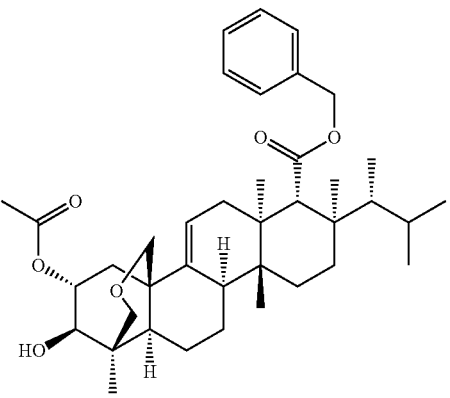

A flask was charged with enfumafungin (16 g, 22.5 mmol) and Et₃SiH (120 mL), and the mixture was stirred until complete dissolution occurred. TFA (180 mL) was added, and the solution was stirred at RT for 10 minutes. Toluene (150 mL) was added, and the solvents were evaporated to leave a solid that was used directly.

A solution of the solid (22.5 mmol) in DMF (200 mL) was treated with benzyl bromide (16 mL) and NaHCO₃ (28 g). The mixture was heated to 70° C. for 48 hours. The reaction mixture was allowed to cool to RT and then filtered through a pad of CELITE. The CELITE was washed with DCM, toluene, and MeOH. The resulting solution was concentrated to an oily residue, which was purified by flash chromatography (silica gel, 100% DCM to 92:8 DCM:MeOH) to afford the benzyl ester as a white powder.

Camphorsulfonic acid (4.2 g) was added to a solution of the white powder (11 mmol) in toluene (500 mL) was added, and the mixture was heated at 70° C. for about 1 hour. The reaction was cooled to RT, and pyridine (20 mL) was added. The reaction mixture was concentrated under reduced pressure, and the residue was purified by flash chromatography (silica gel, 100% DCM followed by 98:2 DCM:MeOH, followed by 95:5 DCM:MeOH) to give the title compound as a white solid (6.2 g). ¹H NMR (400 MHz, CDCl₃, ppm) δ 0.71-0.74 (m, 6H), 0.78 (d, J=6.83 Hz, 3H), 0.80-0.84 (m, 6H), 1.15 (s, 3H), 1.16-1.21 (m, 1H), 1.23 (s, 3H), 1.25-1.29 (m, 1H), 1.33-1.63 (m, 7H), 1.70-1.82 (m, 3H), 1.89 (m, 1H), 1.98-2.06 (m, 1H), 2.08 (s, 3H), 2.09-2.16 (m, 1H), 2.33-2.39 (m, 1H), 2.87 (s, 1H), 3.32 (d, J=4.69 Hz, 1H), 3.34 (br. S, 1H), 3.43 (m, 2H), 3.81 (d, J=11.91 Hz, 1H), 4.96 (d, J=12.25 Hz, 1H), 5.12 (d, J=12.25 Hz, 1H), 5.39 (d, J=5.81 Hz, 1H), 5.66-5.74 (m, 1H), and 7.35 (s, 5H).

Intermediate 2: Benzyl(1S,2R,3R,4aR,6aS,7R,8R, 10aR,10bR,12aR)-8-[(1R)-1,2-dimethylpropyl]-2-(hydroxyl)-3-(methoxy)-1,6a,8,10a-tetramethyl-1,3, 4,6,6a,7,8,9,10,10a,10b,11,12,12a-tetradecahydro-2H-1,4a-(methanooxymethano)chrysene-7-carboxylate

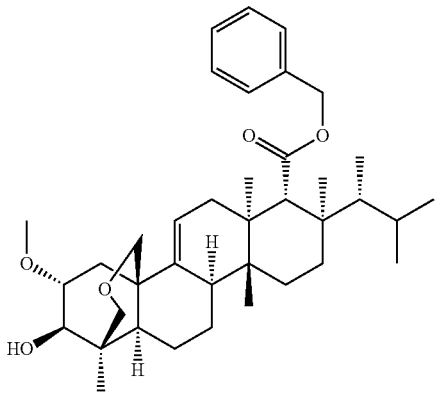

Et$_3$SiH (202.2 ml, 1269.5 mmol) was added, in one portion, to a slurry of enfumafungin (90.0 g, 126.9 mmol) in 846 ml of toluene with mechanical stirring at RT. TFA (202.4 ml, 2627.8 mmol) was then added dropwise at a rapid rate. Once the TFA addition was complete, the resulting amber colored solution was allowed to stir at RT for 2.5 hours. The TFA/toluene solution was then concentrated to dryness. Fresh toluene (300-500 ml) was added, and the mixture was once again concentrated to dryness. The toluene-stripping procedure was repeated twice more. The crude solid was then dried overnight on a high vacuum line to yield 120 g of a purple-brown solid. This material was carried on to the next step without additional purification.

H$_2$SO$_4$ (31.2 ml, 585.3 mmol) was added dropwise at a fast rate to a solution of the purple-brown solid (120 g crude material, ~126.9 mmol) in MeOH (1.27 L) with mechanical stirring. Once the addition was complete, the resulting solution was warmed to 65° C. and was allowed to stir for 4.5 hours. During the course of the reaction, a white solid precipitated. The reaction was cooled to RT, and the white solid was isolated by filtration. The solid was then washed with MeOH (2×200 ml) and CH$_3$CN (2×200 ml). After drying, 47.91 g of a white solid was recovered.

Additional material was isolated from the initial filtrate and subsequent washings 15 as follows. The total liquid volume was reduced to one-third the original volume by evaporation in vacuo. An excess of H$_2$O was added, and a purple-white solid precipitated. The solid was filtered, washed with 3:7 MeOH:H$_2$O (2×100 mL) and CH$_3$CN (2×100 mL) and dried to give an additional 7.30 g of product as a brownish-white solid. The combined yield of product was 55.21 g (86.5%).

This product (55.21 g, 109.8 mmol), NaHCO$_3$ (147.5 g, 1756.8 mmol) and benzyl bromide (65.29 ml, 549.0 mmol) were combined in 550 ml DMF with mechanical stirring. The mixture was warmed to 65° C. and was allowed to stir for 4.5 hours. The DMF was removed in vacuo, and the resulting crude material was dissolved in 1 L of 3:2 H$_2$O:MeOH. The mixture was vigorously stirred for 2-3 hours. During this time, a brownish-white solid formed. The precipitate was filtered and washed with additional 3:2 H$_2$O/MeOH (2×250 mL). The solid was then rinsed with heptane and was allowed to air-aspirate to initial dryness. The white solid recovered was then transferred to a recrystallizing dish and placed in a vacuum oven at 30° C. for 4 hours to give 52.2 g of white solid.

Additional material was isolated from the H$_2$O/MeOH and heptane filtrates as follows. The combined solutions were extracted with EtOAc. The combined EtOAc washings were dried over Na$_2$SO$_4$ and concentrated to dryness. The resulting material was purified by SiO$_2$ chromatography (3:7 EtOAc:DCM) to yield an additional 5.42 g of product as a white solid. The total combined yield of Intermediate 2 was 57.6 g (88.5%).

Intermediate 3: Benzyl(1S,2R,3R,4aR,6aS,7R,8R, 10aR,10bR,12aR)-3-(acetyloxy)-8-[(1R)-1,2-dimethylpropyl]-2-(hydroxyl)-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylate

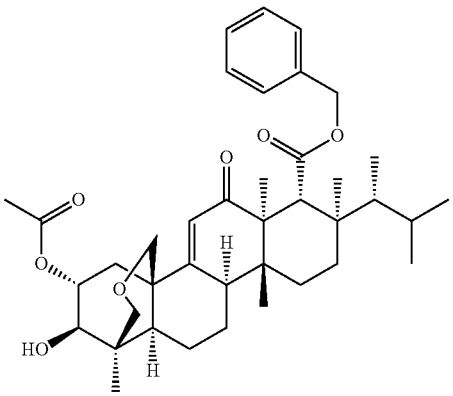

Step 1: Benzyl(1S,2R,3R,4aR,6aS,7R,8R,10aR, 10bR,12aR)-2,3-bis(acetyloxy)-8-[(1R)-1,2-dimethylpropyl]-1,6a,8,10a-tetramethyl-1,3,4,6,6a,7,8,9,10, 10a,10b,11,12,12a-tetradecahydro-2H-1,4a-(methanooxymethano)chrysene-7-carboxylate Pyridine (5 mL), AcCl (2.1 mL), and DMAP (200 mg) were added to a stirred solution of benzyl(1S,2R,3R,4aR,6aS, 7R,8R,10aR,10bR,12aR)-3-(acetyloxy)-8-[(1R)-1,2-dimethylpropyl]-2-hydroxy-1,6a,8,10a-tetramethyl-1,3,4,6,6a, 7,8,9,10,10a,10b,11,12,12a-tetradecahydro-2H-1,4a-(methanooxymethano)chrysene-7-carboxylate (Intermediate 1, 2.2 g, 3.5 mmol) in DCM (150 mL). The reaction mixture was stirred at RT for about 2 hours. DCM (200 mL) was added, and the organic solution was washed with aqueous HCl (1.0 N), saturated NaHCO$_3$ solution, and saturated NaCl solution. The organic phase was dried over anhydrous Na$_2$SO$_4$ and filtered, and the solvents were evaporated under reduced pressure. The residue was purified by flash chromatography (silica gel: 80:20 heptane:EtOAc) to afford benzyl (1S,2R,3R,4aR,6aS,7R,8R,10aR,10bR,12aR)-2,3-bis(acetyloxy)-8-[(1R)-1,2-dimethylpropyl]-1,6a,8,10a-tetramethyl-1,3,4,6,6a,7,8,9,10,10a,10b,11,12,12a-tetradecahydro-2H-1, 4a-(methanooxymethano)chrysene-7-carboxylate (2.0 g).

Step 2: (1S,2R,3R,4aR,6aS,7R,8R,10aR,10bR, 12aR)-2,3-Bis(acetyloxy)-8-[(1R)-1,2-dimethylpropyl]-1,6a,8,10a-tetramethyl-1,3,4,6,6a,7,8,9,10,10a, 10b,11,12,12a-tetradecahydro-2H-1,4a-(methanooxymethano)chrysene-7-carboxylic acid The product of step 1 (2.0 g) was dissolved in MeOH (120 mL), and PdOH (700 mg) was added. A H₂ atmosphere was secured (balloon), and the reaction mixture was stirred at RT for about 1 hour. The palladium catalyst was removed by filtration, and the solvent was evaporated to leave a carboxylic acid (1.7 g).

Step 3: Benzyl(1S,2R,3R,4aR,6aS,7R,8R,10aR, 10bR,12aR)-3-(acetyloxy)-8-[(1R)-1,2-dimethylpropyl]-2-(hydroxyl)-1,6a,8,10a-tetramethyl-6-oxo-1,3, 4,6,6a,7,8,9,10,10a,10b,11,12,12a-tetradecahydro-2H-1,4a-(methanooxymethano)chrysene-7-carboxylate The product of step 2 (1.7 g) was added to a chilled (−20° C.) round-bottom flask containing chromium trioxide (12 g) and dimethyl pyrazole (11.4 g) in DCM (400 mL). The reaction solution was stirred for 16 hours and allowed to warm to RT. The reaction was judged complete by TLC analysis. The reaction contents were diluted by additional DCM (400 mL) and washed with saturated NaHCO₃. The aqueous phase was washed with additional DCM and EtOAc. All organic phases were combined and dried over Na₂SO₄ before being concentrated. The residue was purified by flash chromatography (silica gel, 0:20 heptane:EtOAc). The purified material was dissolved in DCM and washed with aqueous HCl (10% solution) and saturated NaCl before being dried over Na₂SO₄ and concentrated. The purified material (820 mg) was dissolved in DMF (70 mL) with benzyl bromide (1.7 mL) and NaHCO₃ (2.3 g). The reaction mixture was stirred at 50° C. for 16 hours and judged complete by TLC. The reaction mixture was cooled to RT, and EtOAc was added. The organic phase was washed with H₂O and twice with 10% aqueous NH₄Cl solution before being dried over Na₂SO₄ and concentrated. The residue was purified by flash chromatography (silica gel: 88:12 heptane:EtOAc) to yield purified material (560 mg). The purified material was dissolved in MeOH (50 mL) and K₂CO₃ (112 mg) was added. The reaction solution was stirred at RT for 3 hours and judged complete by TLC. EtOAc was added to the reaction solution, and the organic phase was washed with H₂O and saturated NaCl solution before being dried over Na₂SO₄ and concentrated. The resulting material (450 mg) was dissolved in HOAc (27 mL) and concentrated H₂SO₄ (270 μL) was added. The reaction was stirred at RT for 2 hours and judged complete by TLC analysis. H₂O (1 mL) and EtOAc were added to the reaction solution. The organic phase was gently washed (stirring Erlenmayer flask) with saturated NaHCO₃ solution and saturated NaCl before being dried over H₂SO₄ and concentrated. The residue was purified by flash chromatography (86:14 heptane:EtOAc) to yield the title compound (300 mg). ¹H NMR (400 MHz, CDCl₃, ppm) δ 0.70 (d, J=7.14 Hz, 3H), 0.73 (d, J=6.70 Hz, 3H), 0.78-0.82 (m, 6H), 0.85 (s, 3H), 0.85-0.91 (m, 1H), 1.10 (s, 3H), 1.20-1.41 (m, 3H), 1.43-1.72 (m, 4H), 1.73 (s, 3H), 1.81-1.94 (m, 3H), 2.09 (s, 3H), 2.13-2.20 (m, 1H), 2.38 (dd, J=13.38, 7.11 Hz, 1H), 2.51-2.59 (m, 1H), 3.14 (s, 1H), 3.30-3.37 (m, 2H), 3.43-3.57 (m, 2H), 3.87 (d, J=12.03 Hz, 1H), 5.00 (d, J=12.31 Hz, 1H), 5.26 (d, J=12.25 Hz, 1H), 5.69-5.78 (m, 1H), 5.79 (d, J=2.58 Hz, 1H), 7.29-7.40 (m, 3H), and 7.45-7.51 (m, 2H).

EXAMPLES

Example 1

(1S,2R,3R,4aR,6aS,7R,8R,10aR,10bR,12aR)-3-(acetyloxy)-2-(2-amino-3-methyl-butyryloxy)-8-[(1R)-1,2-dimethylpropyl]-1,6a,8,10a-tetramethyl-1, 3,4,6,6a,7,8,9,10,10a,10b,11,12,12a-tetradecahydro-2H-1,4a-(methanooxymethano)chrysene-7-carboxylic acid

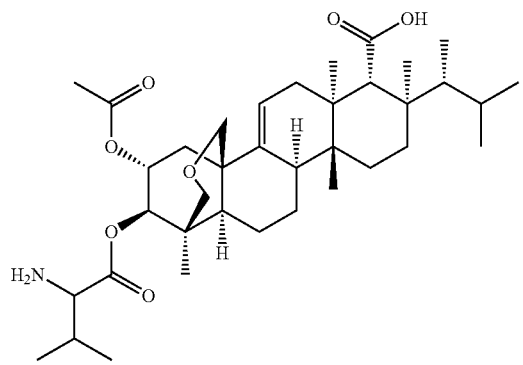

A flask was charged with Intermediate 1 (50 mg, 0.08 mmol), Cbz-Val-OH (0.32 mmol), DMAP (0.64 mmol), and DCC (0.64 mmol) in THF (5 mL). The reaction was stirred at RT for 24 hours, and the reaction was judged to be complete by TLC analysis. The reaction mixture was filtered through an ACRODISC, and the filtrate was concentrated. The residue was dissolved in MeOH and purified by reverse-phase HPLC (70:30 MeOH:H₂O to 100% MeOH). The desired product was dissolved in MeOH (2 mL) with two drops of DCM added to aid dissolution. PdOH (60 mg) was added and H₂ atmosphere was secured (balloon). The reaction mixture was stirred at RT for 20 minutes and judged complete by TLC. The reaction contents were filtered over a pad of CELITE and concentrated to yield the title compound (8 mg). Calculated for C₃₇H₅₉NO₇: 629.Observed: 630 (M+H)⁺. ¹H NMR (400 MHz, MeOH-d4) δ ppm 0.73 (s, 3 H) 0.76-0.79 (m, 3 H) 0.78-0.81 (m, 3 H) 0.87 (d, J=6.70 Hz, 3 H) 0.92 (d, J=6.81 Hz, 3 H) 1.04 (d, J=6.98 Hz, 3 H) 1.08 (d, J=6.92 Hz, 3 H) 1.19 (s, 3 H) 1.23 (s, 3 H) 1.36-1.66 (m, 4 H) 1.74-1.89 (m, 3 H) 1.92-2.02 (m, 3 H) 2.06-2.23 (m, 4 H) 2.26-2.36 (m, 1 H) 2.46-2.58 (m, 1 H) 2.86 (s, 1 H) 3.41-3.57 (m, 4 H) 3.50 (s, 4 H) 3.69 (d, J=12.25 Hz, 1 H) 4.09 (d, J=3.79 Hz, 1 H) 5.52 (s, 1 H) 5.80-5.95 (m, 1 H).

In a similar manner as described for Example 1, from Intermediate 1 and the appropriate benzyloxycarbonyl protected amino acid, the following compounds of formula (IA) were prepared, where the R⁴ group is connected to the remainder of the molecule via the right-most bond shown in the R⁴ group:

(IA)

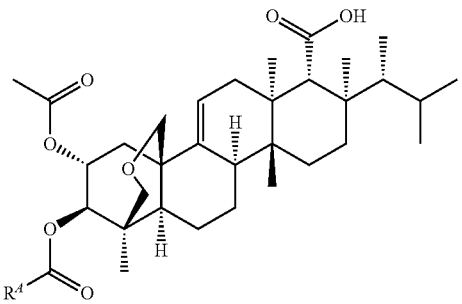

| Example # | Compound Name | $R^A$ | Mass | $^1$H NMR (400 MHz, MeOH-d4) δ |
|---|---|---|---|---|
| 2 | (1S,2R,3R,4aR,6aS,7R,8R,10aR,10bR,12aR)-3-(acetyloxy)-2-(2-amino-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | $H_2N$—CH$_2$— (glycyl) | Calculated for $C_{34}H_{53}NO_7$: 587. Observed: 588 (M + H)$^+$. | 0.69-0.73 (s, 3 H) 0.78 (d, 3 H) 0.76-0.78 (s, 3 H) 0.86 (d, 3 H) 0.91 (d, 3 H) 1.17-1.20 (s, 3 H) 1.21-1.24 (s, 3 H) 1.24-1.33 (m, 4 H) 1.38-1.67 (m, 6 H) 1.72-1.89 (m, 4 H) 1.93-1.96 (s, 3 H) 1.98-1.98 (s, 3 H) 2.08-2.26 (m, 2 H) 2.40-2.51 (m, 1 H) 2.85-2.86 (s, 1 H) 3.42-3.57 (m, 3 H) 3.62-3.83 (m, 3 H) 5.52 (d, 1 H) 5.81-5.92 (m, 1 H) |
| 3 | (1S,2R,3R,4aR,6aS,7R,8R,10aR,10bR,12aR)-3-(acetyloxy)-2-(2-amino-4-carbamoyl-butyryloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | H$_2$NOC—(CH$_2$)$_2$—CH(NH$_2$)— | Calculated for $C_{37}H_{58}N_2O_8$: 658. Observed: 659 (M + H)$^+$. | 0.78 (s, 3 H) 0.80 (s, 3 H) 0.87 (d, J = 6.65 Hz, 3 H) 0.92 (d, J = 6.81 Hz, 3 H) 1.19 (s, 3 H) 1.23 (s, 3 H) 1.35-1.68 (m, J = 66.80 Hz, 10 H) 1.71-1.89 (m, 6 H) 1.96 (s, 5 H) 2.05-2.27 (m, 5 H) 2.38-2.53 (m, 3 H) 3.41-3.57 (m, 1 H) 3.62-3.77 (m, 2 H) 4.94-5.04 (m, 1 H) 5.52 (s, 1 H) 5.78-6.01 (m, 1 H) |
| 4 | (1S,2R,3R,4aR,6aS,7R,8R,10aR,10bR,12aR)-3-(acetyloxy)-2-(2-amino-pentanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | CH$_3$CH$_2$CH$_2$—CH(NH$_2$)— | Calculated for $C_{37}H_{59}NO_7$: 629. Observed: 630 (M + H)$^+$. | 0.68-0.73 (m, 3 H) 0.78 (s, 3 H) 0.80 (s, 3 H) 0.87 (d, J = 6.70 Hz, 3 H) 0.92 (d, J = 6.70 Hz, 3 H) 1.19 (s, 1 H) 1.23 (s, 3 H) 1.33-1.68 (m, 13 H) 1.67-1.89 (m, 7 H) 1.90-2.03 (m, 6 H) 2.06-2.34 (m, 3 H) 2.40-2.58 (m, 2 H) 2.86 (s, 1 H) 3.40-3.60 (m, 1 H) 3.61-3.75 (m, 1 H) 4.93-5.05 (m, 1 H) 5.51 (s, 1 H) 5.77-6.05 (m, 1 H) |

-continued

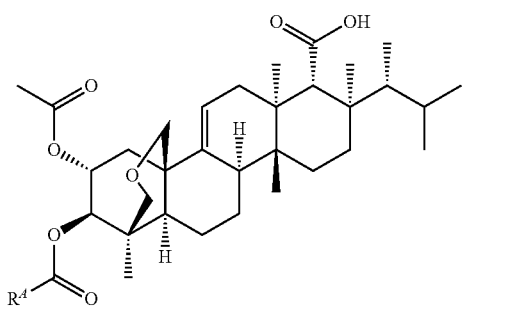

(IA)

| Example # | Compound Name | $R^A$ | Mass | $^1$H NMR (400 MHz, MeOH-d4) δ |
|---|---|---|---|---|
| 5 | (1S,2R,3R,4aR,6aS,7R,8R, 10aR,10bR,12aR)-3-(acetyloxy)-2-(2,6-diamino-hexanoyloxy)-8-[(1R)-1,2-dimethylpropyl]-1,6a,8,10a-tetramethyl-1,3,4,6,6a,7,8,9,10,10a, 10b,11,12,12a-tetradecahydro-2H-1,4a-(methanooxymethano) chrysene-7-carboxylic acid | H$_2$N~~~~~NH$_2$ | Calculated for C$_{38}$H$_{62}$N$_2$O$_7$: 658. Observed: 659 (M + H)$^+$. | 0.78 (s, 3 H) 0.80 (s, 3 H) 0.86 (d, 3 H) 0.91 (d, 3 H) 1.19 (s, 3 H) 1.21-1.25 (m, 3 H) 1.39-1.64 (m, 9 H) 1.63-1.89 (m, 7 H) 1.89-2.01 (m, 6 H) 2.05-2.30 (m, 3 H) 2.35-2.55 (m, 2 H) 2.86 (s, 1 H) 2.94 (s, 2 H) 3.42-3.58 (m, 4 H) 3.62-3.74 (m, 2 H) 4.90-5.04 (m, 1 H) 5.52 (s, 1 H) 5.81-5.98 (m, 1 H) |
| 6 | (1S,2R,3R,4aR,6aS,7R,8R, 10aR,10bR,12aR)-3-(acetyloxy)-2-(2-amino-4-hydroxy-butyryloxy)-8-[(1R)-1,2-dimethylpropyl]-1,6a,8,10a-tetramethyl-1,3,4,6,6a,7,8,9,10,10a, 10b,11,12,12a-tetradecahydro-2H-1,4a-(methanooxymethano) chrysene-7-carboxylic acid | HO~~~NH$_2$ | Calculated for C$_{35}$H$_{55}$NO$_8$: 617. Observed: 618 (M + H)$^+$. | 0.78 (s, 3 H) 0.80 (s, 3 H) 0.87 (d, J = 6.65 Hz, 3 H) 0.92 (d, J = 6.81 Hz, 3 H) 1.19 (s, 3 H) 1.23 (s, 3 H) 1.35-1.67 (m, 7 H) 1.72-1.88 (m, 5 H) 1.90-2.04 (m, 5 H) 2.05-2.26 (m, 2 H) 2.36-2.57 (m, 1 H) 2.86 (s, 1 H) 3.42-3.60 (m, 5 H) 3.61-3.77 (m, 2 H) 3.84-3.93 (m, 1 H) 3.98-4.08 (m, 1 H) 4.92-5.06 (m, 1 H) 5.52 (s, 1 H) 5.80-5.99 (m, 1 H) |
| 7 | (1S,2R,3R,4aR,6aS,7R,8R, 10aR,10bR,12aR)-3-(acetyloxy)-2-(2,5-diamino-pentanoyloxy)-8-[(1R)-1,2-dimethylpropyl]-1,6a,8,10a-tetramethyl-1,3,4,6,6a,7,8,9,10,10a, 10b,11,12,12a-tetradecahydro-2H-1,4a-(methanooxymethano) chrysene-7-carboxylic acid | H$_2$N~~~~NH$_2$ | Calculated for C$_{37}$H$_{60}$N$_2$O$_7$: 644. Observed: 645 (M + H)$^+$. | 0.78 (s, 3 H) 0.80 (s, 3 H) 0.86 (d, 3 H) 0.91 (d, 3 H) 1.19 (s, 3 H) 1.23 (s, 3 H) 1.52 (s, 8 H) 1.72-1.91 (m, 6 H) 1.91-2.03 (m, 5 H) 2.03-2.29 (m, 4 H) 2.33-2.52 (m, 1 H) 2.86 (s, 1 H) 2.94-3.08 (m, 2 H) 3.44-3.59 (m, 5 H) 3.64-3.76 (m, 1 H) 3.83-3.94 (m, 1 H) 4.95-5.07 (m, 1 H) 5.51 (s, 1 H) 5.81-6.05 (m, 1 H) |

-continued

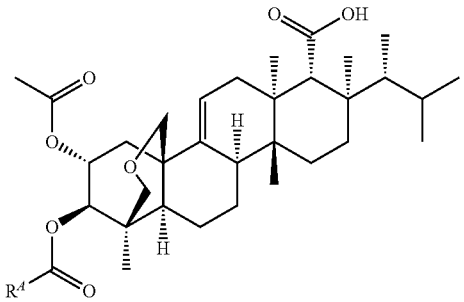

(IA)

| Example # | Compound Name | R^A | Mass | $^1$H NMR (400 MHz, MeOH-d4) δ |
|---|---|---|---|---|
| 8 | (1S,2R,3R,4aR,6aS,7R,8R,10aR,10bR,12aR)-3-(acetyloxy)-2-(2-amino-butyryloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | [structure with NH$_2$] | Calculated for $C_{36}H_{57}NO_7$: 615. Observed: 616 (M + H)$^+$. | 0.68-0.75 (m, J = 5.00 Hz, 3 H) 0.78 (s, 3 H) 0.79 (s, 3 H) 0.87 (d, J = 6.65 Hz, 3 H) 0.92 (d, J = 6.76 Hz, 3 H) 0.99-1.08 (m, 3 H) 1.19 (s, 3 H) 1.23 (s, 3 H) 1.24-1.45 (m, 3 H) 1.55-1.78 (m, 5 H) 1.77-1.93 (m, 5 H) 1.92-2.02 (m, 4 H) 2.02-2.27 (m, 2 H) 2.38-2.56 (m, 1 H) 2.86 (s, 1 H) 3.39-3.57 (m, 5 H) 3.62-3.75 (m, 1 H) 5.04 (d, 1 H) 5.51 (s, 1 H) 5.81-6.00 (m, 1 H) |
| 9 | (1S,2R,3R,4aR,6aS,7R,8R,10aR,10bR,12aR)-3-(acetyloxy)-2-(2-amino-3-carboxypropionyoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | [structure HO$_2$C, NH$_2$] | Calculated for $C_{36}H_{55}NO_9$: 645. Observed: 668 (M + Na)$^+$. | 0.77 (s, 6 H) 0.79 (s, 3 H) 0.86 (d, J = 6.54 Hz, 3 H) 0.91 (d, J = 6.59 Hz, 3 H) 1.20 (s, 3 H) 1.23 (s, 3 H) 1.38-1.68 (m, 5 H) 1.72-1.85 (m, 8 H) 1.96-2.03 (m, 5 H) 2.06-2.19 (m, 1 H) 2.22 (s, 1 H) 2.55-2.69 (m, 1 H) 2.79-2.87 (m, 1 H) 3.40-3.59 (m, 4 H) 3.63-3.79 (m, 1 H) 4.95-5.07 (m, 1 H) 5.50 (s, 1 H) 5.79-5.99 (m, 1 H) |
| 10 | (1S,2R,3R,4aR,6aS,7R,8R,10aR,10bR,12aR)-3-(acetyloxy)-2-(2-piperidinylcarboxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | [piperidine structure NH] | Calculated for $C_{38}H_{59}NO_7$: 641. Observed: 642 (M + H)$^+$. | 0.75 (s, 3 H) 0.80 (s, 3 H) 0.90 (d, J = 6.65 Hz, 3 H) 0.94 (d, J = 6.84 Hz, 3 H) 1.22 (s, 3 H) 1.25 (s, 3 H) 1.27-1.39 (m, 3 H) 1.44-1.75 (m, 9 H) 1.75-1.97 (m, 7 H) 1.98 (s, 3 H) 2.10-2.32 (m, 4 H) 2.42-2.59 (m, 1 H) 2.89 (s, 1 H) 3.00-3.14 (m, 1 H) 3.42-3.59 (m, 5 H) 3.65-3.79 (m, 1 H) 4.05-4.18 (m, 1 H) 5.00-5.13 (m, 1 H) 5.55 (s, 1 H) 5.86-6.07 (m, 1 H) |

(IA)

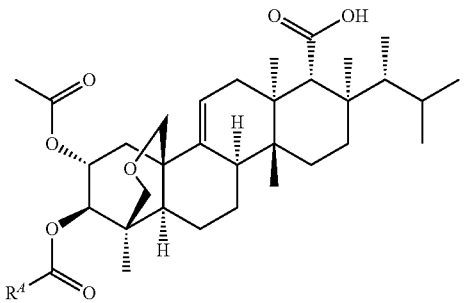

| Example # | Compound Name | R^A | Mass | $^1$H NMR (400 MHz, MeOH-d4) δ |
|---|---|---|---|---|
| 11 | (1S,2R,3R,4aR,6aS,7R,8R,10aR,10bR,12aR)-3-(acetyloxy)-2-(2-pyrrolidinylcarboxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | pyrrolidinyl-NH | Calculated for $C_{37}H_{57}NO_7$: 627. Observed: 628 $(M + H)^+$. | 0.68 (s, 3 H) 0.74-0.82 (m, 6 H) 0.86 (d, 3 H) 0.92 (d, 3 H) 1.20 (s, 3 H) 1.23 (s, 3 H) 1.26-1.66 (m, 7 H) 1.67-1.91 (m, 7 H) 1.96 (s, 3 H) 2.09-2.27 (m, 3 H) 2.37-2.49 (m, 1 H) 2.84 (s, 1 H) 2.86-2.95 (m, 2 H) 3.00-3.12 (m, 1 H) 3.41-3.56 (m, 4 H) 3.64-3.73 (m, 1 H) 3.74-3.84 (m, 1 H) 4.86-4.98 (m, 1 H) 5.34-5.63 (m, 1 H) 5.68-6.07 (m, 1 H) |
| 12 | (1S,2R,3R,4aR,6aS,7R,8R,10aR,10bR,12aR)-3-(acetyloxy)-2-(3-aminopropionyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | $H_2N$-propyl | Calculated for $C_{35}H_{55}NO_7$: 601. Observed: 602 $(M + H)^+$. | 0.78 (s, 3 H) 0.80 (s, 3 H) 0.87 (d, J = 6.65 Hz, 3 H) 0.92 (d, J = 6.76 Hz, 3 H) 1.19 (s, 3 H) 1.23 (s, 3 H) 1.57 (s, 7 H) 1.66-1.91 (m, 6 H) 1.90-2.03 (m, 5 H) 2.05-2.26 (m, 2 H) 2.33-2.53 (m, 1 H) 2.69-2.84 (m, 2 H) 2.86 (s, 1 H) 3.11-3.27 (m, 2 H) 3.38-3.59 (m, 4 H) 3.69 (d, 1 H) 4.89-4.96 (m, 1 H) 5.52 (s, 1 H) 5.80-5.94 (m, 1 H) |
| 13 | (1S,2R,3R,4aR,6aS,7R,8R,10aR,10bR,12aR)-3-(acetyloxy)-2-(3-aminobutyryloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | $H_2N$-sec-butyl | Calculated for $C_{36}H_{57}NO_7$: 615. Observed: 616 $(M + H)^+$. | 0.69-0.74 (m, J = 2.14 Hz, 3 H) 0.80 (s, 3 H) 0.90 (d, J = 6.65 Hz, 3 H) 0.94 (d, J = 6.77 Hz, 3 H) 1.22 (s, 3 H) 1.25 (s, 3 H) 1.27-1.32 (m, 3 H) 1.37 (d, J = 6.65 Hz, 3 H) 1.42-1.69 (m, 7 H) 1.73-1.93 (m, 6 H) 1.99 (s, 3 H) 2.07-2.26 (m, J = 41.44 Hz, 2 H) 2.40-2.56 (m, 1 H) 2.66-2.82 (m, 2 H) 2.89 (s, 1 H) 3.43-3.62 (m, 3 H) 3.61-3.75 (m, 2 H) 4.93-5.01 (m, 1 H) 5.54 (s, 1 H) 5.81-5.98 (m, 1 H) |

-continued

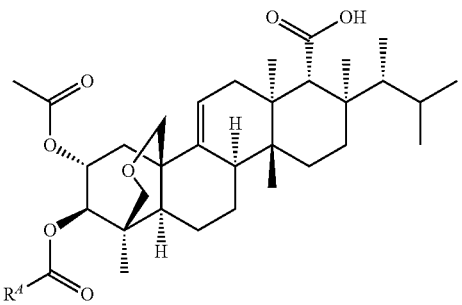

(IA)

| Example # | Compound Name | $R^A$ | Mass | $^1$H NMR (400 MHz, MeOH-d4) δ |
|---|---|---|---|---|
| 14 | (1S,2R,3R,4aR,6aS,7R,8R,10aR,10bR,12aR)-3-(acetyloxy)-2-(3-amino-propionyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | H₂N~~~ | Calculated for $C_{36}H_{57}NO_7$: 615. Observed: 616 $(M + H)^+$. | 0.70 (s, 3 H) 0.80 (s, 3 H) 0.90 (d, J = 6.71 Hz, 3 H) 0.94 (d, J = 6.77 Hz, 3 H) 1.22 (s, 3 H) 1.26 (s, 3 H) 1.27-1.33 (m, 3 H) 1.40-1.70 (m, J = 69.09 Hz, 8 H) 1.73-1.88 (m, 5 H) 1.97 (s, 3 H) 2.10-2.29 (m, J = 35.28 Hz, 3 H) 2.40-2.60 (m, 3 H) 2.89 (s, 1 H) 2.96-3.05 (m, 1 H) 3.41-3.61 (m, 4 H) 3.70 (d, J = 12.02 Hz, 1 H) 4.89-4.96 (m, 1 H) 5.54 (d, J = 5.86 Hz, 2 H) 5.81-6.02 (m, 1 H) |
| 15 | (1S,2R,3R,4aR,6aS,7R,8R,10aR,10bR,12aR)-3-(acetyloxy)-2-(2-amino-5-formylamino-pentanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | H-N(H)-CH₂~~~-NH₂ with CHO | Calculated for $C_{39}H_{62}N_2O_8$: 686. Observed: 687 $(M + H)^+$. | 0.75 (s, 3 H) 0.78 (s, 3 H) 0.87 (d, 3 H) 0.93 (d, 3 H) 1.22 (s, 3 H) 1.23-1.28 (m, 3 H) 1.40-1..59 (m, 7 H) 1.62-1.83 (m, 9 H) 1.85-1.99 (m, 6 H) 2.02-2.28 (m, 3 H) 2.40-2.51 (m, 2 H) 2.89 (s, 1 H) 2.98 (s, 2 H) 3.40-3.56 (m, 4 H) 3.60-3.70 (m, 2 H) 4.92-5.05 (m, 1 H) 5.50 (s, 1 H) 5.80-5.96 (m, 1 H) 8.23 (s, 1H). |
| 16 | (1S,2R,3R,4aR,6aS,7R,8R,10aR,10bR,12aR)-3-(acetyloxy)-2-(4-amino-pyrrolidine-2-carboxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | H₂N-pyrrolidine-NH | Calculated for $C_{37}H_{58}N_2O_7$: 642. Observed: 643 $(M + H)^+$. | 0.73-0.81 (m, J = 7.71, 7.71 Hz, 6 H) 0.87 (d, J = 6.69 Hz, 3 H) 0.92 (d, J = 6.78 Hz, 3 H) 1.19 (s, 3 H) 1.23 (s, 3 H) 1.26-1.62 (m, 8 H) 1.62-1.89 (m, 9 H) 1.99 (s, 3 H) 2.08-2.33 (m, 3 H) 2.36-2.52 (m, 1 H) 2.86 (s, 1 H) 3.42-3.61 (m, 4 H) 3.63-3.82 (m, 2 H) 4.12 (s, 1 H) 4.49-4.63 (m, 1 H) 5.03 (d, J = 9.08 Hz, 1 H) 5.51 (s, 1 H) 5.76-6.00 (m, 1 H) |

-continued

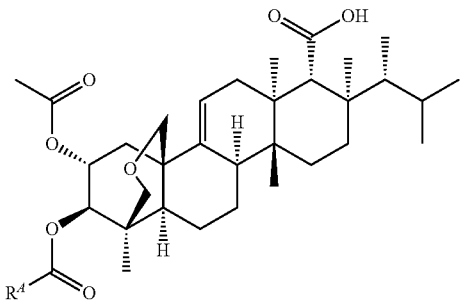
(IA)

| Example # | Compound Name | $R^4$ | Mass | $^1$H NMR (400 MHz, MeOH-d4) δ |
|---|---|---|---|---|
| 17 | (1S,2R,3R,4aR,6aS,7R,8R,10aR,10bR,12aR)-3-(acetyloxy)-2-(2-amino-6-guanidino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | H$_2$N–C(=NH)–NH–(CH$_2$)$_4$–CH(NH$_2$)– | Calculated for C$_{38}$H$_{62}$N$_4$O$_7$: 686. Observed: 687 (M + H)$^+$. | 0.77 (s, 3 H) 0.79 (s, 3 H) 0.87 (d, J = 6.64 Hz, 3 H) 0.91 (d, J = 6.78 Hz, 3 H) 1.19 (s, 3 H) 1.22 (s, 3 H) 1.39-1.67 (m, 8 H) 1.69-1.90 (m, 7 H) 1.99 (s, 6 H) 2.07-2.29 (m, 3 H) 2.36-2.56 (m, 1 H) 2.86 (s, 1 H) 3.50 (s, 4 H) 3.66 (s, 1 H) 4.06-4.24 (m, 1 H) 5.02 (d, 1 H) 5.51 (s, 1 H) 5.81-6.01 (m, 1 H) |
| 18 | (1S,2R,3R,4aR,6aS,7R,8R,10aR,10bR,12aR)-3-(acetyloxy)-2-(2-(2-amino-acetylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | H$_2$N–CH$_2$–C(=O)–NH–Et | Calculated for C$_{36}$H$_{56}$N$_2$O$_8$: 644. Observed: 645 (M + H)$^+$. | 0.69 (s, 3 H) 0.75-0.82 (m, 6 H) 0.87 (d, J = 6.74 Hz, 3 H) 0.92 (d, J = 6.78 Hz, 3 H) 1.19 (s, 3 H) 1.23 (s, 3 H) 1.24-1.37 (m, 3 H) 1.37-1.69 (m, 6 H) 1.71-1.90 (m, 3 H) 1.92-1.97 (m, 1 H) 1.99 (s, 3 H) 2.09-2.27 (m, 2 H) 2.37-2.48 (m, 1 H) 2.86 (s, 1 H) 3.40-3.56 (m, 3 H) 3.67 (d, J = 11.96 Hz, 1 H) 3.73 (s, 2 H) 3.95-4.10 (m, 2 H) 4.90 (d, J = 9.22 Hz, 1 H) 5.51 (d, J = 6.10 Hz, 1 H) 5.81-5.95 (m, 1 H) |
| 19 | (1S,2R,3R,4aR,6aS,7R,8R,10aR,10bR,12aR)-3-(acetyloxy)-2-(2-(2-methylamino-acetylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | MeHN–CH$_2$–C(=O)–NH–Et | Calculated for C$_{37}$H$_{58}$N$_2$O$_8$: 658. Observed: 659 (M + H)$^+$. | 0.74-0.81 (m, 6 H) 0.87 (d, J = 6.69 Hz, 3 H) 0.92 (d, J = 6.78 Hz, 3 H) 1.19 (s, 3 H) 1.23 (s, 3 H) 1.25-1.37 (m, 3 H) 1.37-1.69 (m, 6 H) 1.71-1.89 (m, 3 H) 1.93-1.97 (m, 1 H) 1.98 (s, 3 H) 2.08-2.27 (m, 2 H) 2.40-2.47 (m, 1 H) 2.49 (s, 3 H) 2.85 (s, 1 H) 3.43 (s, 2 H) 3.44-3.57 (m, 3 H) 3.67 (d, J = 11.91 Hz, 1 H) 3.99 (s, 2 H) 4.90 (d, J = 9.13 Hz, 1 H) 5.43-5.58 (m, 1 H) 5.76-5.95 (m, 1 H) |

Example 20

(1S,2R,3R,4aR,6aS,7R,8R,10aR,10bR,12aR)-3-(acetyloxy)-2-(4-hydroxy-pyrrolidine-2-carboxy)-8-[1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid

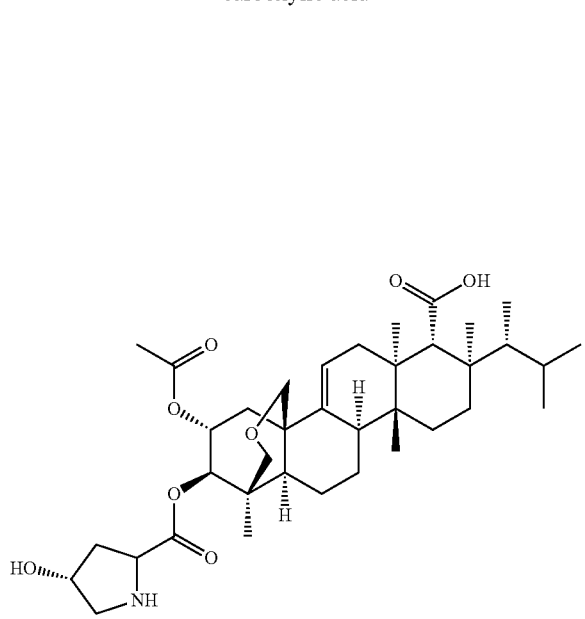

A flask was charged with Intermediate 1 (50 mg, 0.08 mmol), Cbz-(Boc-O) Hyp-OH (0.32 mmol), DMAP (0.64 mmol), and DCC (0.64 mmol) in THF (5 mL). The reaction was stirred at RT for 24 hours, and the reaction was judged to be complete by TLC analysis. The reaction mixture was filtered through an ACRODISC, and the filtrate was concentrated. The residue was dissolved in MeOH and purified by reverse-phase HPLC (70:30 MeOH:H₂O to 100% MeOH). The product was dissolved in MeOH (2 mL) with two drops of DCM added to aid dissolution. PdOH (60 mg) was added, and H₂ atmosphere was secured (balloon). The reaction mixture was stirred at RT for 20 minutes and judged complete by TLC. The reaction contents were filtered over a pad of CELITE and concentrated. The concentrate was then dissolved in TFA:DCM 1:1 (6 mL) and stirred at RT for 30 minutes and judged complete by TLC analysis. The reaction solution was concentrated to yield the title compound (32 mg). Calculated for $C_{37}H_{57}NO_8$: 643.Observed: 644 (M+H)⁺. ¹H NMR (400 MHz, MeOH-d4) δ ppm 0.75-0.79 (m, 3 H) 0.79-0.82 (m, 3 H) 0.87 (d, 3 H) 0.92 (d, 3 H) 1.17-1.20 (m, 3 H) 1.21-1.23 (m, 3 H) 1.36-1.69 (m, 8 H) 1.72-1.90 (m, 7 H) 1.91-2.04 (m, 4 H) 2.04-2.28 (m, 3 H) 2.40-2.56 (m, 2 H) 2.78-2.89 (m, 1 H) 3.25-3.37 (m, 2 H) 3.42-3.60 (m, 4 H) 3.66 (d, 1 H) 4.61 (s, 1 H) 4.97-5.08 (m, 1 H) 5.53 (s, 1 H) 5.78-6.04 (m, 1 H).

Example 21

(1S,2R,3R,4aR,6aS,7R,8R,10aR,10bR,12aR)-3-(acetyloxy)-2-(2-amino-3-(2-amino-ethoxy)-propionyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid

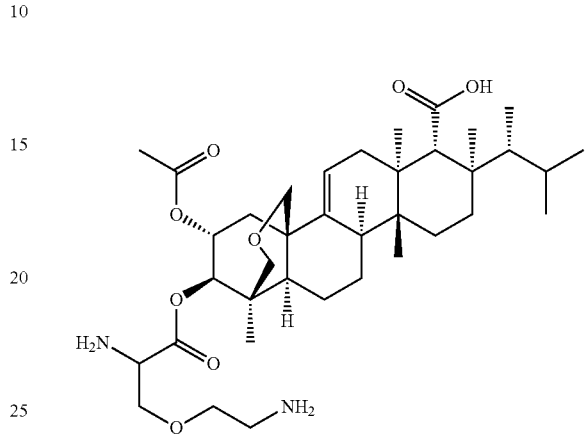

Step 1: (S)-2-tert-Butoxycarbonylamino-3-(2-tert-butoxycarbonylamino-ethoxy)-propionic acid (S)-2-amino-3-(2-amino-ethoxy)-propionic acid (200 mg) and Boc anhydride (661 mg) were added to a mixture of dioxane:H₂O:1N NaOH (1:1:1, 3 mL). The reaction mixture was stirred at RT for 2.5 hours. Additional NaOH solution was added (2N NaOH; 200 µL), and the reaction was stirred for 16 hours. The reaction was judged complete by TLC analysis, and the reaction contents were concentrated to 1 mL total volume. Several drops of 10% aqueous NaHSO₄ solution were added to obtain a pH of 2, and the resulting suspension was extracted with EtOAc. The organic phase was concentrated, and the residue was flash chromatographed (silica gel, 95:5 DCM:MeOH) to yield the title product (142 mg). Calculated for $C_{15}H_{28}N_2O_7$: 348.Observed: 371 (M+Na)⁺.

Step 2: (1S,2R,3R,4aR,6aS,7R,8R,10aR,10bR,12aR)-3-(acetyloxy)-2-(2-amino-3-(2-amino-ethoxy)-propionyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid The title compound (10 mg) was obtained as described in Example 20, using Intermediate 1 (40 mg, 0.065 mmol) and (S)-2-tert-butoxycarbonylamino-3-(2-tert-butoxycarbonylamino-ethoxy)-propionic acid (0.258 mmol), DMAP (0.161 mmol), and DCC (0.258 mmol) in THF (4 mL) was obtained the title compound (10 mg). Calculated for $C_{37}H_{60}N_2O_8$: 660.Observed: 661 (M+H)⁺. ¹H NMR (400 MHz, MeOH-d4) δ ppm 0.63 (d, J=10.79 Hz, 3 H) 0.67-0.73 (m, 6 H) 0.78 (d, J=6.59 Hz, 3 H) 0.83 (d, J=6.69 Hz, 3 H) 1.10 (s, 3H) 1.14 (s, 3 H) 1.16-1.27 (m, 3 H) 1.28-1.64 (m, 6 H) 1.64-1.83 (m, 3 H) 1.84-1.88 (m, 1 H) 1.90 (s, 3 H) 2.02-2.17 (m, 2 H) 2.28-2.45 (m, 1 H) 2.78 (s, 1 H) 2.97-3.16 (m, 2 H) 3.34-3.51 (m, 2 H)

3.53-3.77 (m, 3 H) 3.82-3.93 (m, 2 H) 3.95-4.05 (m, 1 H) 4.25-4.40 (m, 1 H) 4.92 (dd, J=16.94, 9.13 Hz, 1 H) 5.43 (d, J=4.59 Hz, 1 H) 5.74-5.91 (m, 1 H).

Example 22

(1S,2R,3R,4aR,6aS,7R,8R,10aR,10bR,12aR)-3-(acetyloxy)-2-(2-amino-3-(2-amino-ethanesulfonyl)-propionyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid

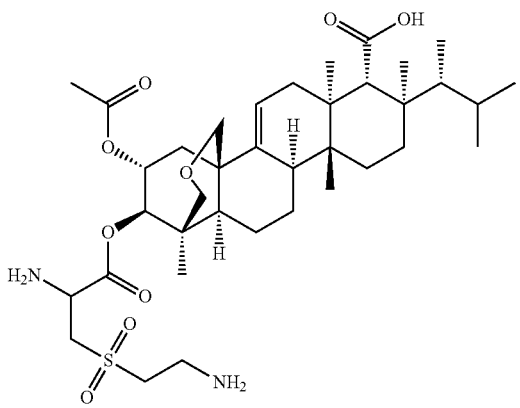

(R)-2-tert-butoxycarbonylamino-3-(2-tert-butoxycarbonylamino-ethylsulfanyl)-propionic acid (780 mg) was obtained as described in Example 21, step 1, from (R)-2-amino-3-(2-amino-ethylsulfanyl)-propionic acid (500 mg).

A round-bottomed flask was charged with Intermediate 1 (50 mg, 0.08 mmol), protected acid from above (0.32 mmol), DMAP (0.32 mmol), and DCC (0.32 mmol) in THF (6 mL). The reaction was stirred at RT for 24 hours, and the reaction was judged to be complete by TLC analysis. The reaction mixture was filtered through silica gel, and the filtrate was concentrated. The residue was dissolved in MeOH and purified by reverse-phase HPLC (70:30 MeOH:H$_2$O to 100% MeOH).

The product (25 mg) was dissolved in dry DCM (3 mL), 3-chloroperoxybenzoic acid (77%; 0.065 mmol) was added, and the reaction was stirred at RT for 2 hours. The reaction was judged complete by TLC analysis, and the reaction solution was washed with Na$_2$S$_2$O$_3$ solution and with saturated, aqueous NaCl. The organic phase was dried over Na$_2$SO$_4$ before being concentrated. The residue was purified by reverse phase HPLC (70:30 MeOH:H$_2$O to 100% MeOH).

The product was dissolved in TFA:DCM 1:1 (2 mL) and stirred at room RT for 5 minutes. The reaction was judged complete by TLC analysis. The reaction contents were concentrated and purified by flash chromatography (95:5 to 90:10 DCM:MeOH). The recovered material was dissolved in MeOH (2 mL) with two drops of DCM added to aid dissolution. PdOH (80 mg) was added, and H$_2$ atmosphere was secured (balloon). The reaction mixture was stirred at RT for 6.5 hours and judged complete by TLC. The reaction contents were filtered over a pad of CELITE and concentrated to yield the title compound (10 mg). Calculated for C$_{37}$H$_{60}$N$_2$O$_9$S: 708. Observed: 709 (M+H)$^+$. $^1$H NMR (400 MHz, MeOH-d4) δ ppm 0.71 (s, 3 H) 0.75-0.81 (m, 6 H) 0.87 (d, J=6.69 Hz, 3 H) 0.92 (d, J=6.83 Hz, 3 H) 1.19 (s, 3 H) 1.23 (s, 3 H) 1.24-1.38 (m, 3 H) 1.38-1.71 (m, 6 H) 1.71-1.91 (m, 3 H) 1.96-1.98 (m, 1 H) 1.99 (s, 3 H) 2.12-2.24 (m, 2 H) 2.42-2.50 (m, 1 H) 2.86 (s, 1 H) 3.40-3.58 (m, 7 H) 3.64-3.77 (m, 4 H) 4.96 (d, J=9.71 Hz, 1 H) 5.51 (s, 1 H) 5.85-6.00 (m, 1 H).

Example 23

(1S,2R,3R,4aR,6aS,7R,8R,10aR,10bR,12aR)-3-(acetyloxy)-2-(2-amino-3-(2-amino-ethylamino)-propionyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid

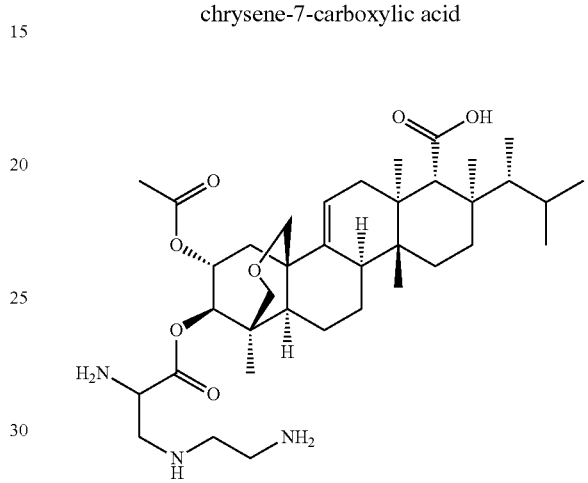

A round-bottomed flask was charged with Intermediate 1 (50 mg, 0.08 mmol), (S)-2-benzyloxycarbonylamino-3-tert-butoxycarbonylamino-propionic acid (0.32 mmol), DMAP (0.32 mmol), and DCC (0.32 mmol) in THF (6 mL). The reaction was stirred at RT for 24 hours, and the reaction was judged to be complete by TLC analysis. The reaction mixture was filtered through silica gel, and the filtrate was concentrated. The residue was dissolved in MeOH and purified by reverse-phase HPLC (70:30 MeOH:H$_2$O to 100% MeOH). The product (63 mg) was dissolved in TFA:DCM 1:1 (3 mL) and stirred at RT for 5 minutes. The reaction was judged complete by TLC analysis. The reaction contents were concentrated, and a portion of the material (31 mg) was dissolved in DCE (2 mL). (2-Oxo-ethyl)-carbamic acid tert-butyl ester (0.044 mmol), TEA (0.111 mmol), and HOAc (0.111 mmol) were added to this solution. The reaction solution was stirred for 5 minutes, and sodium triacetoxyborohydride (0.111 mmol) was added. The reaction mixture was stirred for 2.5 hours at RT and judged complete by TLC analysis. The reaction was quenched by adding several drops of H$_2$O, and the organic phase was filtered through a small pad of silica gel. The filtrate was concentrated and purified by reverse-phase HPLC (70:30 to 100:0 MeOH:H$_2$O). The purified product (22 mg) was collected from relevant fractions and dissolved in a 1:1 solution of TFA:DCM (2 mL). The reaction solution was stirred at RT for 5 minutes and judged complete by TLC analysis. The reaction solution was concentrated to dryness, and the residue was purified by flash chromatography (silica gel, 98:2 DCM:MeOH) to yield 19 mg of Boc-deprotected material. This Boc-departed material was dissolved in MeOH (2 mL) with two drops of DCM added to aid dissolution. PdOH (35 mg) was added, and H$_2$ atmosphere was secured (balloon). The reaction mixture was stirred at RT for 30 minutes and judged complete by TLC. The reaction contents were filtered over a pad of CELITE and concentrated to yield the title compound (13 mg). Calculated for $C_{37}H_{61}N_3O_7$: 659. Observed: 660 (M+H)+. 1H NMR (400 MHz, MeOH-d4) δ ppm 0.68-0.75 (m, J=10.54 Hz, 3 H) 0.75-0.82 (m, 6 H) 0.87 (d, J=6.69 Hz, 3 H) 0.92 (d, J=6.83 Hz, 3 H) 1.19 (s, 3 H) 1.23 (s, 3 H) 1.24-1.36 (m, 3 H) 1.38-1.69 (m, 6 H) 1.72-1.90 (m, 3 H) 1.93-1.97 (m, 1 H) 1.99 (s, 3 H) 2.08-2.26 (m, 2 H) 2.38-2.51 (m, 1 H) 2.86 (s, 1 H) 2.88-3.00 (m, 3 H) 3.01-3.08 (m, 2 H) 3.10-3.18 (m, 1 H) 3.43-3.59 (m, 3 H) 3.64-3.74 (m, 1 H) 4.07-4.24 (m, 1 H) 5.01 (dd, J=15.16, 9.15 Hz, 1H) 5.52 (d, J=4.25 Hz, 1 H) 5.84-6.01 (m, 1 H).

Example 24

(1S,2R,3R,4aR,6aS,7R,8R,10aR,10bR,12aR)-3-(acetyloxy)-2-(2-(2-amino-ethylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid

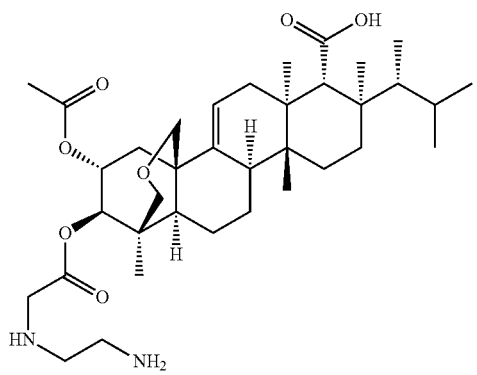

A round-bottomed flask was charged with Intermediate 1 (50 mg, 0.08 mmol), Cbz-N-(N-β-Boc-aminoethyl)-Gly-OH (0.2 mmol), DMAP (0.2 mmol), and DCC (0.2 mmol) in THF (6 mL). The reaction was stirred at RT for 24 hours, and the reaction was judged to be complete by TLC analysis. The reaction solution was concentrated and purified by flash chromatography (2:1 heptane:EtOAc). The product was dissolved in TFA:DCM 1:1 (1 mL) and stirred at RT for 25 minutes. The reaction was judged complete by TLC analysis. The reaction contents were concentrated, and the residue was purified by reverse-phase HPLC (85:15 to 100:0 MeOH:H2O). The product (30 mg) was dissolved in MeOH (2 mL) with 2 drops of EtOAc added to aid dissolution. PdOH (50 mg) and one drop HOAc were added, and H2atmosphere was secured (balloon). The reaction mixture was stirred at RT for 30 minutes and judged complete by TLC. The reaction contents were filtered over a pad of CELITE and concentrated to yield the title compound (24 mg). Calculated for $C_{36}H_{58}N_2O_7$: 630.Observed: 631 (M+H)+. 1H NMR (400 MHz, MeOH-d4) δ ppm 0.69 (s, 3 H) 0.78 (s, 3 H) 0.79 (d, 3 H) 0.87 (d, J=6.69 Hz, 3 H) 0.92 (d, J=6.78 Hz, 3 H) 1.19 (s, 3 H) 1.23 (s, 3 H) 1.24 (s, 3 H) 1.36-1.68 (m 5 H) 1.72-1.90 (m, 5 H) 1.96 (s, 3 H) 1.99 (s, 3 H) 2.10-2.27 (m, 3H) 2.38-2.48 (m, 1 H) 2.86 (s, 1 H) 2.87-2.94 (m, 1 H) 2.96-3.04 (m, 2 H) 3.40-3.61 (m, 5 H) 3.67 (d, J=11.96 Hz, 1 H) 4.93 (d, J=9.27 Hz, 1 H) 5.47-5.54 (m, 1 H) 5.82-5.94 (m, 1 H).

Example 25

(1S,2R,3R,4aR,6aS,7R,8R,10aR,10bR,12aR)-3-(acetyloxy)-2-(4-amino-5-hydroxy-pentanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid The title compound (2 mg) was obtained as described in Example 24, from Intermediate 3 (50 mg, 0.08 mmol) and 5-benzyloxy-4-(S-tert-butoxycarbonylamino)-pentanoic acid (0.2 mmol). Calculated for $C_{37}H_{59}NO_8$: 645.Observed: 646 (M+H)+. 1H NMR (400 MHz, MeOH-d4) δ ppm 0.68 (s, 3 H) 0.77 (s, 3 H) 0.78 (d, 3 H) 0.87 (d, J=6.74 Hz, 3 H) 0.91 (d, J=6.74 Hz, 3 H) 1.19 (s, 3 H) 1.23 (s, 3 H) 1.24-1.48 (m, 5 H) 1.48-1.74 (m, 5 H) 1.76-2.02 (m, 5H) 2.06 (s, 3 H) 2.10 (s, 3 H) 2.13-2.27 (m, 2 H) 2.34-2.59 (m, 3 H) 2.86 (s, 1 H) 3.11-3.15 (m,1H) 3.41-3.61 (m, 3 H) 3.63-3.78 (m, 2 H) 4.10-4.16 (m,1 H) 4.40-4.63 (m, 1 H) 5.47-5.55 (m, 1H) 5.79-5.93 (m, 1 H).

Example 26

(1S,2R,3R,4aR,6aS,7R,8R,10aR,10bR,12aR)-3-(acetyloxy)-2-(2-(N-hydroxycarbamimidoyl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid A flask was charged with Intermediate 1 (50 mg, 0.08 mmol), cyanoacetic acid (0.24 mmol), DMAP (0.32 mmol), and DCC (0.32 mmol) in THF (2 mL) and the reaction was stirred at RT for 24 hours. Additional cyanoacetic acid (0.24 mmol), DMAP (0.32 mmol), and DCC (0.32 mmol) were added, and the reaction solution was stirred at RT for 8 hours. The reaction was judged complete by TLC analysis. The reaction was concentrated, and the residue was purified by reverse-phase HPLC (70:30 to 100:0 MeOH:H$_2$O). The purified material (30 mg) was dissolved in MeOH (3 mL), hydroxylamine hydrochloride (15 mg; 0.22 mmol) and TEA (31 μL; 0.22 mmol) were added, and the reaction solution was stirred at RT overnight. The reaction was judged complete by TLC analysis, and the reaction contents were concentrated. The residue was purified by flash chromatography (silica gel; 75:25 heptane:EtOAc, then 90:10 DCM:MeOH). The desired product (15 mg) was dissolved in MeOH, PdOH (20 mg) was added and H$_2$ atmosphere was secured (balloon). The reaction mixture was stirred for 20 minutes at RT and judged complete by TLC analysis. The reaction contents were filtered over a pad of CELITE and concentrated to yield the title compound (12 mg). Calculated for C$_{35}$H$_{54}$N$_2$O$_8$: 630. Observed: 631 (M+H)$^+$. $^1$H NMR (400 MHz, MeOH-d4) δ ppm 0.70 (s, 3 H) 0.77 (s, 3 H) 0.87 (d, J=6.69 Hz, 3 H) 0.91 (d, J=6.78 Hz, 3 H) 1.19 (s, 3 H) 1.23 (s, 3 H) 1.25-1.33 (m, 3 H) 1.35-1.65 (m, J=77.95 Hz, 5 H) 1.69-1.89 (m, 7 H) 1.96 (s, 3 H) 2.00-2.29 (m, 4 H) 2.36-2.54 (m, 1H) 2.85 (s, 1 H) 3.50 (s, 3 H) 3.65-3.81 (m, 2 H) 4.82-4.95 (m, 1 H) 5.49 (s, 1 H) 5.73-5.92 (m, 1H).

Example 27

(1S,2R,3R,4aR,6aS,7R,8R,10aR,10bR,12aR)-3-(acetyloxy)-2-(2-(N-(2,6-diaminohexanoyloxy)carbamimidoyl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid As described in Example 26, material (12 mg) was collected prior to the final hydrogenation step and was dissolved in DMF (1 mL). N(α)-Cbz-(N(ε)-Cbz)-Lys-OH (0.018 mmol), 1-(3-dimethylaminopropyl)-3-ethylcarbodiimide hydrochloride (0.018 mmol), and 1-hydroxybenzotriazole (0.018 mmol) were added. The reaction solution was stirred at RT for 16 hours and judged complete by TLC analysis. The reaction contents were concentrated, and the residue was purified by flash chromatography (silica gel; 97:3 DCM:MeOH). The purified material (10 mg) was dissolved in MeOH (2 mL) with DCM (0.5 mL) added to aid dissolution. PdOH (45 mg) was added and H$_2$ atmosphere was secured (balloon). The reaction mixture was stirred for 40 minutes at RT and judged complete by TLC analysis. The reaction contents were filtered over a pad of CELITE and concentrated to yield the title compound (2.4 mg). Calculated for C$_{41}$H$_{66}$N$_4$O$_9$: 758. Observed: 614 (M-Lys)$^+$. $^1$H NMR (400 MHz, MeOH-d4) δ ppm 0.68-1.00 (m, 12 H) 1.11-1.39 (m, J=28.60 Hz, 8 H) 1.61 (s, 8 H) 1.70-1.94 (m, 8 H) 1.91-2.06 (m, 8H) 2.39-2.54 (m, 1 H) 2.86 (s, 1 H) 2.95 (s, 2 H) 3.52 (s, 5 H) 3.60-3.78 (m, 1 H) 4.95 (s, 1 H) 5.50 (s, 1 H) 5.74-6.01 (m, 1 H).

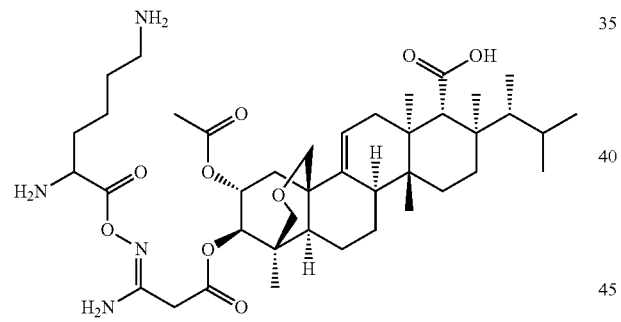

Example 28

(1S,2R,3R,4aR,6aS,7R,8R,10aR,10bR,12aR)-3-(acetyloxy)-2-(2-amino-6-(3,5-bis-trifluoromethyl-benzoylamino)-hexanoyloxy)-8-[(1R)-1,2-dimethyl-propyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid

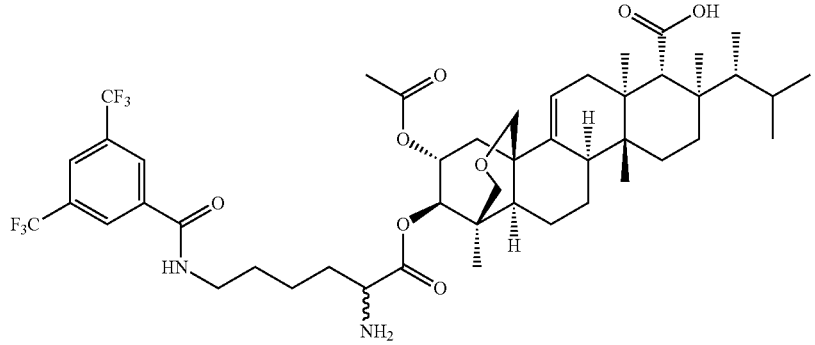

3,5 Bis(trifluoromethyl)benzoyl chloride (0.107 mmol) and TEEA (0.35 mmol) were added to a solution of the compound of Example 5 (0.036 mmol) in DCE (1 mL). The reaction solution was stirred at RT for 16 hours, and the reaction was judged complete by TLC. The reaction solution was concentrated under $N_2$ stream, and the residue was purified by reverse-phase HPLC (70:30 gradient to 100:0 MeOH: $H_2O$). The relevant fractions were concentrated, and the material obtained was dissolved in MeOH (2 mL). PdOH (70 mg) was added and $H_2$ atmosphere (balloon) was secured. The reaction mixture was stirred for 20 minutes at RT. The reaction contents were filtered over CELITE, and the cake was washed extensively with MeOH. The filtrate was concentrated to yield the title compound (6.9 mg). Calculated for $C_{47}H_{64}F_6N_2O_8$: 898. Observed: 899 $(M+H)^+$. $^1H$ NMR (400 MHz, MeOH-d4) δ ppm 0.77 (s, 3H) 0.79 (s, 3 H) 0.87 (d, J=6.64 Hz, 3 H) 0.92 (d, J=6.74 Hz, 3 H) 1.15-1.20 (m, 4 H) 1.20-1.25 (m, 3 H) 1.20-1.35 (m, 4 H) 1.63 (d, J=110.31 Hz, 14 H) 1.86-2.05 (m, 6 H) 2.19 (s, 3 H) 2.30-2.52 (m, 1 H) 2.86 (s, 1 H) 3.44 (s, 4 H) 3.57-3.74 (m, 1 H) 3.95-4.19 (m, 1 H) 5.01 (d, 1 H) 5.50 (s, 1 H) 5.74-5.94 (m, 1 H) 8.18 (s, 1 H) 8.46 (s, 2 H).

In a similar manner as described in Example 28, from the compound described in Example 5 and the appropriate acid chloride, isocyanate or sulfonyl chloride, the following compounds of formula (IB) were prepared, in which the $R^B$ group as shown is connected to the remainder of the molecule via a bond to the carbonyl or sulfonyl portion of the $R^B$ group:

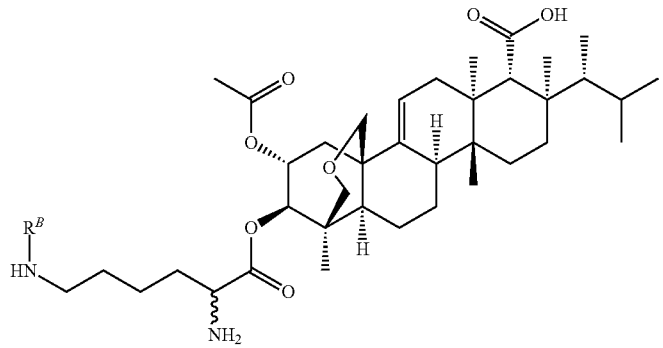

(IB)

| Example # | Compound Name | $R^B$ | Mass | $^1H$ NMR (400 MHz, MeOH-d4) δ |
|---|---|---|---|---|
| 29 | (1S,2R,3R,4aR,6aS,7R,8R,10aR,10bR,12aR)-3-(acetyloxy)-2-(2-amino-6-(3-bromo-benzoylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | 3-bromobenzoyl | Calculated for $C_{45}H_{66}BrN_2O_8$: 841. Observed: 763 $(M - Br)^+$. | 0.77 (s, 3 H) 0.79 (s, 3 H) 0.87 (d, J = 6.64 Hz, 3 H) 0.92 (d, J = 6.74 Hz, 3 H) 1.18 (s, 3 H) 1.23 (s, 3 H) 1.21-1.34 (m, 5 H) 1.38-1.65 (m, 5 H) 1.56-1.87 (m, 9 H) 1.88-2.01 (m, 5 H) 2.05-2.30 (m, 3 H) 2.35-2.55 (m, 1 H) 2.86 (s, 1 H) 3.36-3.54 (m, 5 H) 3.66 (s, 1 H) 4.00-4.26 (m, 1 H) 4.95-5.10 (m, 1 H) 5.51 (s, 1 H) 5.76-6.01 (m, 1 H) 7.39-7.62 (m, 3 H) 7.83 (d, 1 H) |
| 30 | (1S,2R,3R,4aR,6aS,7R,8R,10aR,10bR,12aR)-3-(acetyloxy)-2-(2-amino-6-(2,2,3,3,4,4,4-heptafluoro-butyrylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | $C_3F_7$-C(O)- | Calculated for $C_{42}H_{61}F_7N_2O_8$: 854. Observed: 855 $(M + H)^+$. | 0.78 (s, 3 H) 0.79 (s, 3 H) 0.87 (d, J = 6.83 Hz, 3 H) 0.92 (d, J = 6.64 Hz, 3 H) 1.19 (s, 3 H) 1.22 (s, 3 H) 1.24-1.44 (m, 4 H) 1.38-1.64 (m, J = 39.10 Hz, 8 H) 1.81 (s, 6 H) 1.93-2.04 (m, 3 H) 2.12-2.30 (m, 5 H) 2.34-2.55 (m, 2 H) 2.87 (s, 1 H) 3.51 (s, 5 H) 3.61-3.78 (m, 1 H) 3.63-3.76 (m, 1 H) 3.88-4.13 (m, 1 H) 3.93-4.13 (m, 255 H) 4.93-5.06 (m, 1 H) 5.53 (s, 1 H) 5.81-6.00 (m, 1 H) |

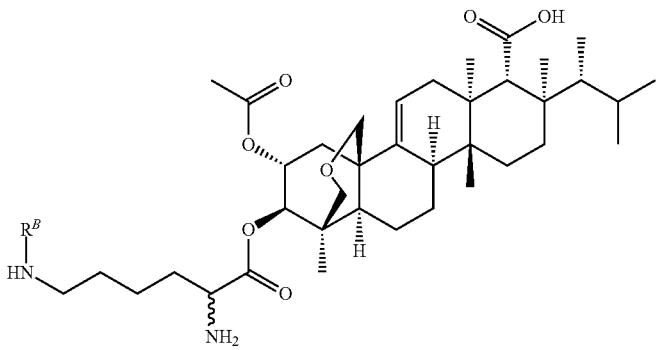

(IB)

| Example # | Compound Name | $R^B$ | Mass | $^1$H NMR (400 MHz, MeOH-d4) δ |
|---|---|---|---|---|
| 31 | (1S,2R,3R,4aR,6aS,7R,8R,10aR,10bR,12aR)-3-(acetyloxy)-2-(2-amino-6-(2-bromo-propionylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | Br with CHO | Calculated for $C_{41}H_{65}BrN_2O_8$: 793. Observed: 716 (M − Br)$^+$. | 0.78 (s, 3 H) 0.79 (s, 3 H) 0.88 (d, 3 H) 0.92 (d, 3 H) 1.12 (s, 3 H) 1.19 (s, 3 H) 1.23 (s, 3 H) 1.36-1.66 (m, J = 41.39 Hz, 8 H) 1.71-1.95 (m, 8 H) 1.99 (s, 3 H) 2.21 (s, 5 H) 2.36-2.62 (m, 1 H) 2.86 (s, 1 H) 3.10-3.26 (m, 2 H) 3.40-3.59 (m, 5 H) 3.62-3.75 (m, 1 H) 3.96-4.17 (m, 1 H) 4.93-5.09 (m, 2 H) 5.44-5.59 (m, 1 H) 5.51 (s, 1 H) 5.77-6.01 (m, 1 H) |
| 32 | (1S,2R,3R,4aR,6aS,7R,8R,10aR,10bR,12aR)-3-(acetyloxy)-2-(2-amino-6-(2-methoxy-acetylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | MeO-CH$_2$-CHO | Calculated for $C_{41}H_{66}N_2O_9$: 730. Observed: 731 (M + H)$^+$. | 0.78 (s, 3 H) 0.79 (s, 3 H) 0.87 (d, J = 6.64 Hz, 3 H) 0.92 (d, J = 6.69 Hz, 3 H) 1.19 (s, 3 H) 1.23 (s, 3 H) 1.26-1.33 (m, 4 H) 1.61 (s, 9 H) 1.68-1.94 (m, 9 H) 1.93-2.04 (m, 3 H) 2.07-2.26 (m, 4 H) 2.40-2.54 (m, 1 H) 2.86 (s, 1 H) 3.41 (s, 3 H) 3.44-3.59 (m, 5 H) 3.59-3.75 (m, 1 H) 4.00-4.20 (m, 1 H) 4.94-5.08 (m, 1 H) 5.51 (s, 1 H) 5.80-6.02 (m, 1 H) |
| 33 | (1S,2R,3R,4aR,6aS,7R,8R,10aR,10bR,12aR)-3-(acetyloxy)-2-(2-amino-6-[(tetrahydro-furan-2-carbonyl)-amino]-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | tetrahydrofuran-3-carbaldehyde | Calculated for $C_{43}H_{68}N_2O_9$: 756. Observed: 757 (M + H)$^+$. | 0.78 (s, 5 H) 0.79 (s, 3 H) 0.87 (d, J = 6.69 Hz, 3 H) 0.92 (d, J = 6.74 Hz, 3 H) 1.19 (s, 3 H) 1.23 (s, 3 H) 1.24-1.31 (m, 3 H) 1.38-1.70 (m, 9 H) 1.75-1.98 (m, 8 H) 1.99 (s, 3 H) 2.09-2.31 (m, 5 H) 2.39-2.59 (m, 1 H) 2.86 (s, 1 H) 3.40-3.57 (m, 6 H) 3.62-3.74 (m, 2 H) 3.80-4.02 (m, 2 H) 4.05-4.34 (m, 1 H) 4.97-5.08 (m, 1 H) 5.52 (s, 1 H) 5.77-6.03 (m, 1 H) |

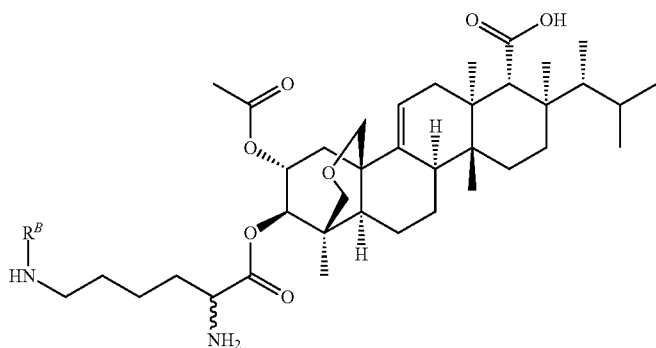

(IB)

| Example # | Compound Name | $R^B$ | Mass | $^1$H NMR (400 MHz, MeOH-d4) δ |
|---|---|---|---|---|
| 34 | (1S,2R,3R,4aR,6aS,7R,8R,10aR,10bR,12aR)-3-(acetyloxy)-2-(2-amino-6-(3-methoxy-benzoylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | 3-MeO-C6H4-C(=O)- | Calculated for $C_{46}H_{68}N_2O_9$: 792. Observed: 793 $(M+H)^+$. | 0.78 (s, 3 H) 0.79 (s, 3 H) 0.87 (d, J = 6.64 Hz, 3 H) 0.92 (d, J = 6.69 Hz, 3 H) 1.19 (s, 3 H) 1.23 (s, 3 H) 1.28 (s, 2 H) 1.56 (s, 11 H) 1.81 (s, 7 H) 1.99 (s, 3 H) 2.21 (s, 3 H) 2.36-2.60 (m, 1 H) 2.86 (s, 1 H) 3.24-3.36 (m, 3 H) 3.37-3.58 (m, 5 H) 3.61-3.73 (m, 1 H) 3.84 (s, 1 H) 4.04-4.21 (m, 1 H) 4.94-5.09 (m, 1 H) 5.51 (s, 1 H) 5.84-5.97 (m, 1 H) 7.02-7.18 (m, 1 H) 7.33-7.46 (m, 3 H) |
| 35 | (1S,2R,3R,4aR,6aS,7R,8R,10aR,10bR,12aR)-3-(acetyloxy)-2-(2-amino-6-(3-fluoro-benzoylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | 3-F-C6H4-C(=O)- | Calculated for $C_{45}H_{65}FN_2O_8$: 780. Observed: 781 $(M+H)^+$. | 0.78 (s, 3 H) 0.79 (s, 3 H) 0.87 (d, J = 6.69 Hz, 3 H) 0.92 (d, J = 6.59 Hz, 3 H) 1.19 (s, 3 H) 1.22 (s, 3 H) 1.25-1.37 (m, 5 H) 1.40-1.71 (m, 10 H) 1.73-1.87 (m, 5 H) 1.96-2.01 (m, 3 H) 2.08-2.27 (m, 3 H) 2.38-2.54 (m, 1 H) 2.89 (s, 1 H) 3.38-3.56 (m, 5 H) 3.59-3.73 (m, 1 H) 4.02-4.17 (m, 1 H) 4.94-5.07 (m, 1 H) 5.44-5.56 (m, 1 H) 5.51 (s, 1 H) 5.79-5.98 (m, 1 H) 7.22-7.35 (m, 1 H) 7.44-7.53 (m, 1 H) 7.54-7.62 (m, 1 H) 7.62-7.74 (m, J = 3.81 Hz, 1 H) |
| 36 | (1S,2R,3R,4aR,6aS,7R,8R,10aR,10bR,12aR)-3-(acetyloxy)-2-(2-amino-6-phenylacetylamino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | PhCH2-C(=O)- | Calculated for $C_{46}H_{68}N_2O_8$: 776. Observed: 777 $(M+H)^+$. | 0.78 (s, 3 H) 0.79 (s, 3 H) 0.87 (d, J = 6.49 Hz, 3 H) 0.92 (d, J = 6.83 Hz, 3 H) 1.19 (s, 3 H) 1.22 (s, 3 H) 1.25-1.36 (m, 4 H) 1.34-1.72 (m, 9 H) 1.71-1.93 (m, 8 H) 1.97 (s, 3 H) 2.07-2.27 (m, 3 H) 2.39-2.57 (m, 1 H) 2.79-2.93 (m, 1 H) 3.42-3.58 (m, 5 H) 3.58-3.76 (m, 1 H) 3.95-4.14 (m, 1 H) 4.77-4.91 (m, 2 H) 4.95-5.11 (m, 1 H) 5.52 (s, 1 H) 5.81-6.01 (m, 1 H) 7.14-7.38 (m, 5 H) |

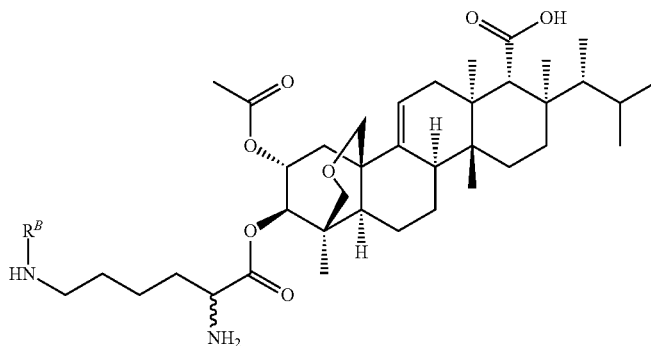

(IB)

| Example # | Compound Name | $R^B$ | Mass | $^1$H NMR (400 MHz, MeOH-d4) δ |
|---|---|---|---|---|
| 37 | (1S,2R,3R,4aR,6aS,7R,8R,10aR,10bR,12aR)-3-(acetyloxy)-2-(2-amino-6-(cyclobutanecarbonyl-amino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | cyclobutyl-CHO | Calculated for $C_{43}H_{68}N_2O_8$: 740. Observed: 741 $(M + H)^+$. | 0.78 (s, 3 H) 0.79 (s, 3 H) 0.87 (d, J = 6.69 Hz, 3 H) 0.92 (d, J = 6.78 Hz, 3 H) 1.19 (s, 3 H) 1.23 (s, 3 H) 1.27-1.35 (m, 8 H) 1.36-1.67 (m, 13 H) 1.73-1.93 (m, 7 H) 1.97 (s, 3 H) 2.05-2.30 (m, 3 H) 2.39-2.55 (m, 1 H) 2.86 (s, 1 H) 3.50 (s, 5 H) 3.58-3.76 (m, 1 H) 3.98-4.17 (m, 1 H) 4.98-5.10 (m, 1 H) 5.52 (s, 1 H) 5.83-6.02 (m, 1 H) |
| 38 | (1S,2R,3R,4aR,6aS,7R,8R,10aR,10bR,12aR)-3-(acetyloxy)-2-(2-amino-6-(3,5-dimethoxy-benzoylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | 3,5-dimethoxybenzaldehyde | Calculated for $C_{47}H_{70}N_2O_{10}$: 822. Observed: 823 $(M + H)^+$. | 0.78 (s, 3 H) 0.79 (s, 3 H) 0.87 (d, J = 6.64 Hz, 3 H) 0.92 (d, J = 6.74 Hz, 3 H) 1.19 (s, 3 H) 1.23 (s, 3 H) 1.21-1.35 (m, 4 H) 1.54 (s, 10 H) 1.72-1.93 (m, 8 H) 1.99 (s, 3 H) 2.07-2.28 (m, 3 H) 2.36-2.56 (m, 1 H) 2.86 (s, 1 H) 3.33-3.74 (m, J = 60.47 Hz, 5 H) 3.82 (s, 6 H) 3.98-4.22 (m, 1 H) 4.95-5.15 (m, 1 H) 5.51 (s, 1 H) 5.75-6.03 (m, 1 H) 6.65 (s, 1 H) 6.99 (s, 2 H) |
| 39 | (1S,2R,3R,4aR,6aS,7R,8R,10aR,10bR,12aR)-3-(acetyloxy)-2-(2-amino-6-(2-oxo-propionylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | methyl 2-oxoacetate | Calculated for $C_{41}H_{64}N_2O_{10}$: 744. Observed: 745 $(M + H)^+$. | 0.78 (s, 3 H) 0.79 (s, 3 H) 0.87 (d, J = 6.64 Hz, 3 H) 0.92 (d, J = 6.74 Hz, 3 H) 1.19 (s, 3 H) 1.22 (s, 3 H) 1.24-1.33 (m, 3 H) 1.63 (s, 11 H) 1.70-1.95 (m, 7 H) 1.99 (s, 3 H) 2.03-2.26 (m, 3 H) 2.37-2.56 (m, 1 H) 2.86 (s, 1 H) 3.53 (s, 5 H) 3.60-3.74 (m, 1 H) 3.87 (s, 3 H) 4.02-4.21 (m, 1 H) 4.96-5.09 (m, 1 H) 5.52 (s, 1 H) 5.81-6.03 (m, 1 H) |

(IB)

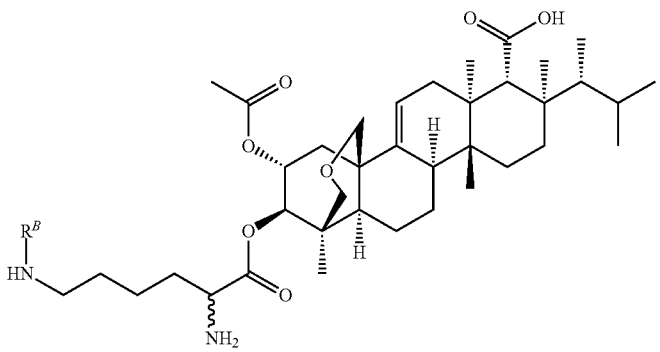

| Example # | Compound Name | $R^B$ | Mass | $^1$H NMR (400 MHz, MeOH-d4) δ |
|---|---|---|---|---|
| 40 | (1S,2R,3R,4aR,6aS,7R,8R,10aR,10bR,12aR)-3-(acetyloxy)-2-(2-amino-6-(3-chloro-benzoylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | 3-chlorobenzoyl | Calculated for $C_{45}H_{65}ClN_2O_8$: 796. Observed: 761 $(M - Cl)^+$. | 0.78 (s, 3 H) 0.79 (s, 3 H) 0.87 (d, J = 6.59 Hz, 3 H) 0.92 (d, J = 6.69 Hz, 3 H) 1.19 (s, 3 H) 1.22 (s, 3 H) 1.28 (s, 2 H) 1.36-1.69 (m, 10 H) 1.67-1.94 (m, 9 H) 1.95 (s, 3 H) 2.19 (s, 3 H) 2.49 (s, 1 H) 2.86 (s, 1 H) 3.50 (s, 5 H) 3.58-3.78 (m, 1 H) 4.00-4.25 (m, 1 H) 4.98-5.06 (m, 1 H) 5.40-5.65 (m, 1 H) 5.76-6.02 (m, 1 H) 7.46 (s, 3 H) 7.79-7.94 (m, 1 H) |
| 41 | (1S,2R,3R,4aR,6aS,7R,8R,10aR,10bR,12aR)-3-(acetyloxy)-2-(2-amino-6-propionylamino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | propionyl | Calculated for $C_{41}H_{66}N_2O_8$: 714. Observed: 715 $(M + H)^+$. | 0.71-0.75 (m, 3 H) 0.78 (s, 3 H) 0.79 (s, 3 H) 0.87 (d, J = 6.64 Hz, 3 H) 0.92 (d, J = 6.74 Hz, 3 H) 1.10-1.17 (m, 2 H) 1.19 (s, 3 H) 1.23 (s, 3 H) 1.25-1.32 (m, 3 H) 1.39-1.68 (m, 10 H) 1.71-1.95 (m, 8 H) 1.99 (s, 3 H) 2.17 (s, 3 H) 2.51 (s, 1 H) 2.86 (s, 1 H) 3.33-3.55 (m, 5 H) 3.61-3.80 (m, J = 27.19 Hz, 1 H) 4.02-4.17 (m, 1 H) 4.98-5.07 (m, 1 H) 5.43-5.58 (m, 1 H) 5.80-6.01 (m, 1 H) |
| 42 | (1S,2R,3R,4aR,6aS,7R,8R,10aR,10bR,12aR)-3-(acetyloxy)-2-(2-amino-6-(4-chloro-benzoylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | 4-chlorobenzoyl | Calculated for $C_{45}H_{65}ClN_2O_8$: 796. Observed: 761 $(M - Cl)^+$. | 0.77 (s, 3 H) 0.79 (s, 3 H) 0.87 (d, J = 6.64 Hz, 3 H) 0.92 (d, J = 6.74 Hz, 3 H) 1.18 (s, 3 H) 1.22 (s, 3 H) 1.24-1.30 (m, 4 H) 1.48 (s, 9 H) 1.74-1.93 (m, 8 H) 1.96-2.04 (m, 3 H) 2.11 (s, 3 H) 2.37-2.56 (m, 1 H) 2.86 (s, 1 H) 3.35-3.54 (m, 5 H) 3.58-3.79 (m, 1 H) 4.02-4.21 (m, 1 H) 4.92-5.09 (m, 1 H) 5.51 (s, 1 H) 5.79-6.00 (m, 1 H) 7.39-7.59 (m, 2 H) 7.82 (d, 2 H |

-continued

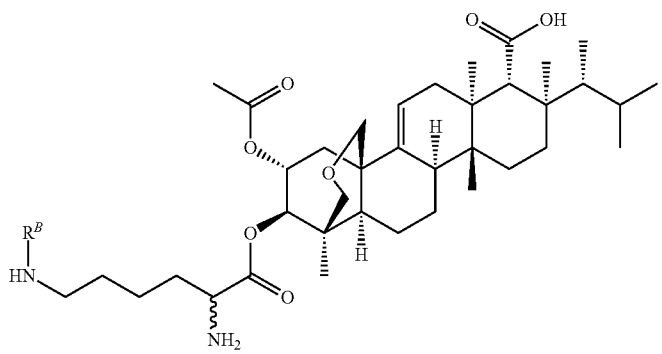

(IB)

| Example # | Compound Name | $R^B$ | Mass | $^1$H NMR (400 MHz, MeOH-d4) δ |
|---|---|---|---|---|
| 43 | (1S,2R,3R,4aR,6aS,7R,8R,10aR,10bR,12aR)-3-(acetyloxy)-2-(6-(2-acetoxy-2-methyl-propionylamino)-2-amino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | AcO — C(CH$_3$)$_2$ — C(=O)— | Calculated for $C_{44}H_{70}N_2O_{10}$: 786. Observed: 787 (M + H)$^+$. | 0.76-0.79 (m, 3 H) 0.79 (s, 3 H) 0.87 (d, J = 6.64 Hz, 4 H) 0.92 (d, J = 6.78 Hz, 4 H) 1.19 (s, 3 H) 1.23 (s, 3 H) 1.26 (s, 4 H) 1.44 (s, 7 H) 1.54 (s, 6 H) 1.77-1.96 (m, 8 H) 1.99 (s, 3 H) 2.07 (s, 3 H) 2.11-2.26 (m, 3 H) 2.51 (s, 1 H) 2.86 (s, 1 H) 3.43-3.57 (m, 5 H) 3.64-3.75 (m, 1 H) 3.96-4.18 (m, 1 H) 4.96-5.07 (m, 1 H) 5.52 (s, 1 H) 5.81-6.03 (m, 1 H) |
| 44 | (1S,2R,3R,4aR,6aS,7R,8R,10aR,10bR,12aR)-3-(acetyloxy)-2-(6-acetylamino-2-amino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | CH$_3$—C(=O)— | Calculated for $C_{40}H_{64}N_2O_8$: 700. Observed: 701 (M + H)$^+$. | 0.78 (s, 3 H) 0.79 (s, 3 H) 0.87 (d, J = 6.69 Hz, 3 H) 0.92 (d, J = 6.78 Hz, 3 H) 1.19 (s, 3 H) 1.23 (s, 3 H) 1.24-1.30 (m, 3 H) 1.55 (s, 10 H) 1.75-1.89 (m, 8 H) 1.95 (s, 3 H) 1.99 (s, 3 H) 2.08-2.28 (m, 3 H) 2.42-2.61 (m, 1 H) 2.86 (s, 1 H) 3.53 (s, 5 H) 3.63-3.78 (m, 1 H) 3.99-4.19 (m, 1 H) 5.03 (s, 1 H) 5.52 (s, 1 H) 5.79-5.98 (m, 1 H) |
| 45 | (1S,2R,3R,4aR,6aS,7R,8R,10aR,10bR,12aR)-3-(acetyloxy)-2-(2-amino-6-(2,2,2-trifluoro-acetylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | F$_3$C—C(=O)— | Calculated for $C_{40}H_{61}F_3N_2O_8$: 754. Observed: 755 (M + H)$^+$. | 0.78 (s, 3 H) 0.79 (s, 3 H) 0.87 (d, J = 6.54 Hz, 3 H) 0.91 (d, J = 6.59 Hz, 3 H) 1.19 (s, 3 H) 1.22 (s, 3 H) 1.24-1.31 (m, 3 H) 1.40-1.70 (m, 10 H) 1.72-1.95 (m, 8 H) 1.99 (s, 3 H) 2.06-2.26 (m, 3 H) 2.36-2.58 (m, 1 H) 2.86 (s, 1 H) 3.48 (s, 5 H) 3.66 (s, 1 H) 3.98-4.25 (m, 1 H) 4.97-5.11 (m, 1 H) 5.51 (s, 1 H) 5.82-6.01 (m, 1 H |

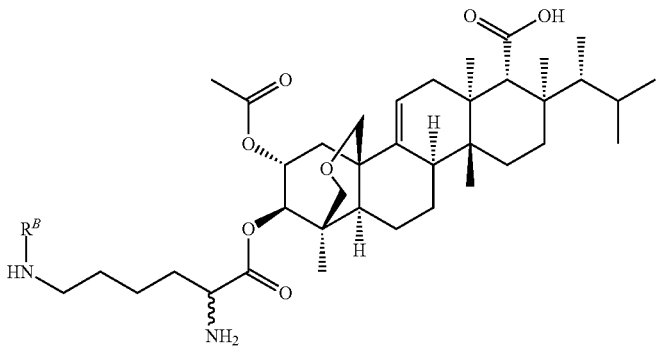

(IB)

| Example # | Compound Name | $R^B$ | Mass | $^1$H NMR (400 MHz, MeOH-d4) δ |
|---|---|---|---|---|
| 46 | (1S,2R,3R,4aR,6aS,7R,8R, 10aR,10bR,12aR)-3-(acetyloxy)-2-(2-amino-6-[3-(4-fluoro-phenyl)-ureido]-hexanoyloxy hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid | 4-F-C6H4-NH-C(O)- | Calculated for $C_{45}H_{66}FN_3O_8$: 795. Observed: 796 (M + H)+. | 0.69-0.75 (m, 3 H) 0.74-0.81 (m, 3 H) 0.87 (d, J = 6.64 Hz, 3 H) 0.92 (d, J = 6.78 Hz, 3 H) 1.17 (s, 3 H) 1.22 (s, 3 H) 1.22-1.30 (m, 3 H) 1.37-1.64 (m, J = 55.01 Hz, 10 H) 1.70-1.87 (m, 7 H) 1.98 (s, 3 H) 2.15 (d, J = 65.50 Hz, 3 H) 2.45 (s, 1 H) 2.85 (s, 1 H) 3.44 (s, 5 H) 3.62-3.74 (m, 2 H) 3.97-4.20 (m, 1 H) 4.95-5.07 (m, 1 H) 5.46 (s, 1 H) 5.82-6.03 (m, 1 H) 7.02 (s, 1 H) 7.27 (s, 1 H) 7.32-7.40 (m, 1 H) 7.42-7.53 (m, 1 H) |
| 47 | (1S,2R,3R,4aR,6aS,7R,8R, 10aR,10bR,12aR)-3-(acetyloxy)-2-(2-amino-6-[3-(4-trifluoromethylphenyl)-ureido]-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid | 4-CF3-C6H4-NH-C(O)- | Calculated for $C_{46}H_{66}F_3N_3O_8$: 845. Observed: 846 (M + H)+. | 0.69-0.73 (m, 3 H) 0.76-0.80 (m, 3 H) 0.87 (d, J = 6.49 Hz, 3 H) 0.92 (d, J = 6.78 Hz, 3 H) 1.15-1.18 (m, 3 H) 1.22 (s, 3 H) 1.23-1.31 (m, 4 H) 1.51 (s, 10 H) 1.61-1.89 (m, 7 H) 1.96 (s, 3 H) 2.03-2.27 (m, 3 H) 2.33-2.59 (m, 1 H) 2.85 (s, 1 H) 3.36-3.51 (m, 5 H) 3.60-3.75 (m, 1 H) 3.84-4.21 (m, 1 H) 4.90-5.10 (m, 1 H) 5.32-5.51 (m, 1 H) 5.82-6.06 (m, 1 H) 7.60 (s, 2 H) 7.65-7.75 (m, 1 H) 7.80-7.94 (m, 1 H) |
| 48 | (1S,2R,3R,4aR,6aS,7R,8R, 10aR,10bR,12aR)-3-(acetyloxy)-2-(2-amino-6-(3-isopropyl-ureido)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid | iPr-NH-C(O)- | Calculated for $C_{42}H_{69}N_3O_8$: 43. Observed: 744 (M + H)+. | 0.71-0.74 (m, J = 6.44 Hz, 3 H) 0.76-0.80 (m, 3 H) 0.87 (d, J = 6.64 Hz, 3 H) 0.91 (d, J = 6.78 Hz, 3 H) 1.11 (d, J = 6.49 Hz, 6 H) 1.19 (s, 3 H) 1.22 (s, 3 H) 1.25-1.30 (m, 4 H) 1.36-1.66 (m, 12 H) 1.75-1.92 (m, 7 H) 1.99 (s, 3 H) 2.05-2.25 (m, 3 H) 2.36-2.54 (m, 1 H) 2.86 (s, 1 H) 3.40-3.60 (m, 4 H) 3.60-3.84 (m, 1 H) 4.00-4.20 (m, 1 H) 4.95-5.14 (m, 1 H) 5.51 (s, 1 H) 5.79-6.02 (m, 1 H |

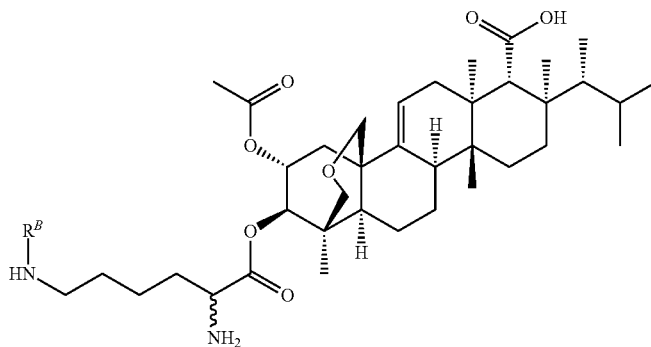

(IB)

| Example # | Compound Name | $R^B$ | Mass | $^1$H NMR (400 MHz, MeOH-d4) δ |
|---|---|---|---|---|
| 49 | (1S,2R,3R,4aR,6aS,7R,8R, 10aR,10bR,12aR)-3-(acetyloxy)-2-(2-amino-6-[3-(4-methoxyphenyl)-ureido]-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | MeO—C6H4—NH—C(O)—NH— | Calculated for $C_{46}H_{69}N_3O_9$: 807. Observed: 808 (M + H)$^+$. | 0.65-0.73 (m, J = 16.06 Hz, 3 H) 0.79 (s, 3 H) 0.87 (d, J = 6.64 Hz, 3 H) 0.92 (d, J = 6.69 Hz, 3 H) 1.18 (s, 3 H) 1.22 (s, 3 H) 1.23-1.32 (m, 4 H) 1.39-1.69 (m, 13 H) 1.72-1.95 (m, 9 H) 2.00-2.24 (m, 4 H) 2.36-2.56 (m, 1 H) 2.86 (s, 1 H) 3.37-3.68 (m, 5 H) 4.00-4.22 (m, 1 H) 4.92-5.13 (m, 1 H) 5.46 (s, 1 H) 5.76-6.10 (m, 2 H) 6.83 (d, 2 H) 7.08-7.38 (m, 2 H) |
| 50 | (1S,2R,3R,4aR,6aS,7R,8R, 10aR,10bR,12aR)-3-(acetyloxy)-2-(2-amino-6-(3-cyclopentyl-ureido)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | cyclopentyl—NH—C(O)—NH— | Calculated for $C_{44}H_{71}N_3O_8$: 769. Observed: 770 (M + H)$^+$. | 0.70-0.74 (m, J = 6.44 Hz, 3 H) 0.78 (s, 3 H) 0.87 (d, J = 6.59 Hz, 3 H) 0.92 (d, J = 6.78 Hz, 3 H) 1.19 (s, 3 H) 1.23 (s, 3 H) 1.26-1.38 (m, 5 H) 1.38-1.74 (m, 14 H) 1.64-1.95 (m, 10 H) 1.99 (s, 3 H) 2.06-2.26 (m, 4 H) 2.35-2.60 (m, 1 H) 2.86 (s, 1 H) 3.38-3.57 (m, 4 H) 3.61-3.80 (m, 1 H) 3.84-4.01 (m, 1 H) 4.02-4.22 (m, 1 H) 5.01 (d, 1 H) 5.51 (s, 1 H) 5.82-6.01 (m, 1 H) |
| 51 | (1S,2R,3R,4aR,6aS,7R,8R, 10aR,10bR,12aR)-3-(acetyloxy)-2-(2-amino-6-[3-(1-methoxycarbonyl-ethyl)-ureido]-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | MeO2C—CH(CH3)—NH—C(O)—NH— | Calculated for $C_{43}H_{69}N_3O_{10}$: 787. Observed: 788 (M + H)$^+$. | 0.70-0.75 (m, J = 6.78 Hz, 3 H) 0.79 (s, 3 H) 0.87 (d, J = 6.64 Hz, 3 H) 0.92 (d, J = 6.78 Hz, 3 H) 1.19 (s, 3 H) 1.23 (s, 3 H) 1.24-1.30 (m, 4 H) 1.34 (d, J = 7.22 Hz, 3 H) 1.40-1.68 (m, 10 H) 1.72-1.93 (m, 8 H) 1.93-2.02 (m, 3 H) 2.08-2.31 (m, 3 H) 2.38-2.58 (m, 1 H) 2.86 (s, 1 H) 3.43-3.58 (m, 4 H) 3.60-3.70 (m, 1 H) 3.71 (s, 3 H) 3.97-4.16 (m, 1 H) 4.20-4.32 (m, 1 H) 5.01 (d, 1 H) 5.52 (s, 1 H) 5.76-6.05 (m, 1 H) |

-continued

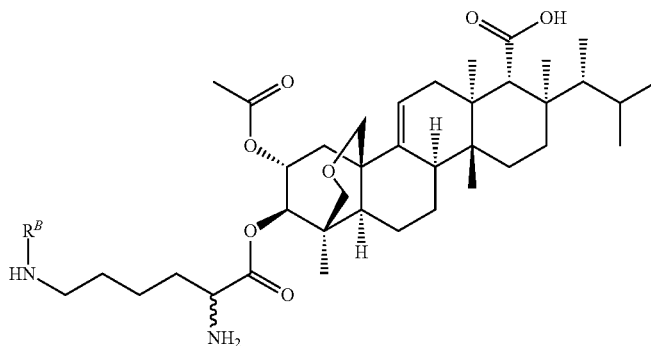

(IB)

| Example # | Compound Name | $R^B$ | Mass | $^1$H NMR (400 MHz, MeOH-d4) δ |
|---|---|---|---|---|
| 52 | (1S,2R,3R,4aR,6aS,7R,8R,10aR,10bR,12aR)-3-(acetyloxy)-2-(2-amino-6-[3-(2-bromo-ethyl)-ureido]-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | Br−⟨⟩−NH−CHO | Calculated for $C_{41}H_{66}BrN_3O_8$: 808. Observed: 809 (M + H)⁺. | 0.72 (s, 3 H) 0.75 (s, 3 H) 0.85 (d, J = 6.45 Hz, 3 H) 0.90 (d, J = 6.50 Hz, 3 H) 1.20 (s, 3 H) 1.23-1.27 (m, 2 H) 1.24-1.39 (m, 9 H) 1.47-1.65 (m, 11 H) 1.75-1.87 (m, 9 H) 1.99 (s, 3 H) 2.02-2.20 (m, 5 H) 2.30-2.40 (m, 1 H) 2.65 (s, 1 H) 3.30-3.60 (m, 1 H) 3.91-4.08 (m, 1 H) 4.97-5.15 (m, 1 H) 5.55 (s, 1 H) 5.88-6.07 (m, 1 H) |
| 53 | (1S,2R,3R,4aR,6aS,7R,8R,10aR,10bR,12aR)-3-(acetyloxy)-2-(2-amino-6-[3-(2-chloro-ethyl)-ureido]-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | Cl−⟨⟩−NH−CHO | Calculated for $C_{41}H_{66}ClN_3O_8$: 763. Observed: 764 (M + H)⁺. | 0.69-0.73 (m, 3 H) 0.78 (s, 3 H) 0.87 (d, J = 6.39 Hz, 3 H) 0.91 (d, J = 6.69 Hz, 3 H) 1.19 (s, 3 H) 1.21-1.24 (m, 3 H) 1.25-1.39 (m, 8 H) 1.46-1.66 (m, 11 H) 1.78-1.89 (m, 9 H) 1.98 (s, 3 H) 2.02-2.29 (m, 5 H) 2.32-2.44 (m, 1 H) 2.63 (s, 1 H) 3.39-3.66 (m, 1 H) 3.91-4.06 (m, 1 H) 4.96-5.19 (m, 1 H) 5.53 (s, 1 H) 5.84-6.05 (m, 1 H) |
| 54 | (1S,2R,3R,4aR,6aS,7R,8R,10aR,10bR,12aR)-3-(acetyloxy)-2-(2-amino-6-(3-hexylureido)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | $C_6H_{13}$−NH−CHO | Calculated for $C_{45}H_{75}N_3O_8$: 785. Observed: 786 (M + H)⁺. | 0.70-0.74 (m, J = 6.93 Hz, 3 H) 0.76-0.80 (m, 3 H) 0.87 (d, J = 6.64 Hz, 3 H) 0.89-0.94 (m, J = 6.59 Hz, 6 H) 1.19 (s, 3 H) 1.25-1.37 (m, 13 H) 1.40-1.67 (m, 15 H) 1.72-1.92 (m, 7 H) 1.99 (s, 3 H) 2.06-2.28 (m, 3 H) 2.41-2.55 (m, 1 H) 2.86 (s, 1 H) 3.39-3.58 (m, 4 H) 3.68 (s, 1 H) 4.00-4.18 (m, 1 H) 5.02 (d, J = 9.13 Hz, 1 H) 5.52 (s, 1 H) 5.79-5.99 (m, 1 H) |

-continued

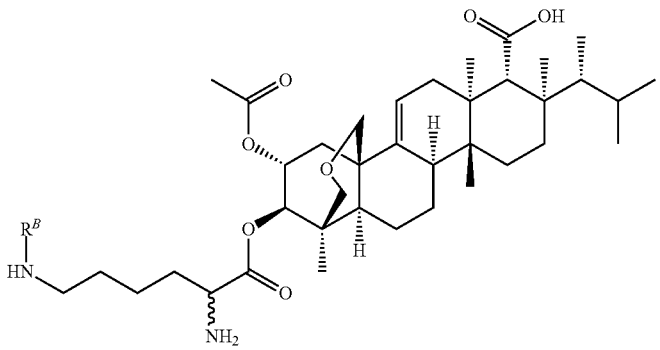

(IB)

| Example # | Compound Name | $R^B$ | Mass | $^1$H NMR (400 MHz, MeOH-d4) δ |
|---|---|---|---|---|
| 55 | (1S,2R,3R,4aR,6aS,7R,8R, 10aR,10bR,12aR)-3-(acetyloxy)-2-(2-amino-6-(3-phenyl-ureido)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | phenyl-NH-C(=O)- | Calculated for $C_{45}H_{67}N_3O_8$: 777. Observed: 800 (M + Na)$^+$. | 0.70-0.73 (m, 3 H) 0.78 (s, 3 H) 0.87 (d, J = 6.49 Hz, 3 H) 0.91 (d, J = 6.44 Hz, 3 H) 1.19 (s, 3 H) 1.22 (s, 3 H) 1.38 (d, J = 78.97 Hz, 10 H) 1.80 (s, 5 H) 1.92-1.96 (m, 7 H) 1.99 (s, 3 H) 2.15 (s, 3 H) 2.38-2.52 (m, 1 H) 2.83 (s, 1 H) 3.37-3.59 (m, 5 H) 3.61-3.77 (m, 1 H) 3.96-4.24 (m, 1 H) 5.01 (d, 1 H) 5.48 (s, 1 H) 5.86 (s, 1 H) 7.20-7.28 (m, 2 H) 7.28-7.42 (m, 2 H) |
| 56 | (1S,2R,3R,4aR,6aS,7R,8R, 10aR,10bR,12aR)-3-(acetyloxy)-2-(2-amino-6-[3-(4-methoxycarbonylphenyl)-ureido]-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | MeO$_2$C-phenyl-NH-C(=O)- | Calculated for $C_{48}H_{71}N_3O_{10}$: 849. Observed: 850 (M + H)$^+$. | 0.57-0.65 (m, J = 13.91, 9.13 Hz, 3 H) 0.67-0.74 (m, J = 7.17 Hz, 3 H) 0.78 (d, J = 6.54 Hz, 3 H) 0.83 (d, J = 6.64 Hz, 3 H) 1.05-1.09 (m, J = 5.52 Hz, 3 H) 1.13 (s, 3 H) 1.16-1.22 (m, 2 H) 1.29 (s, 8 H) 1.46-1.84 (m, J = 61.55 Hz, 13 H) 1.89 (s, 3 H) 1.96-2.18 (m, 3 H) 2.22-2.39 (m, 1 H) 2.76 (s, 1 H) 3.26-3.44 (m, 5 H) 3.45-3.66 (m, 1 H) 3.83-4.09 (m, J = 44.56 Hz, 1 H) 4.27 (d, J = 24.99 Hz, 2 H) 4.83-5.00 (m, 2 H) 5.17-5.44 (m, 1 H) 5.74-5.92 (m, 1 H) 7.28-7.64 (m, J = 45.69 Hz, 2 H) 7.78-8.20 (m, J = 97.52 Hz, 2 H) |
| 57 | (1S,2R,3R,4aR,6aS,7R,8R, 10aR,10bR,12aR)-3-(acetyloxy)-2-(2-amino-6-(3-ethoxycarbonylmethy-ureido)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | EtO-C(=O)-CH$_2$-NH-C(=O)- | Calculated for $C_{43}H_{69}N_3O_{10}$: 787. Observed: 788 (M + H)$^+$. | 0.70-0.74 (m, J = 6.25 Hz, 3 H) 0.78 (s, 3 H) 0.87 (d, J = 6.69 Hz, 3 H) 0.92 (d, J = 6.74 Hz, 3 H) 1.19 (s, 3 H) 1.23 (s, 3 H) 1.27 (t, J = 7.13 Hz, 3 H) 1.48 (s, 11 H) 1.81 (s, 10 H) 1.99 (s, 3 H) 2.05-2.24 (m, 3 H) 2.36-2.53 (m, 1 H) 2.86 (s, 1 H) 3.39-3.58 (m, 5 H) 3.62-3.77 (m, 1 H) 3.86 (s, 2H) 4.05 (s, 1 H) 4.13-4.26 (m, 2 H) 5.02 (d, J = 9.27 Hz, 1 H) 5.51 (s, 1 H) 5.91 (s, 1 H) |

-continued

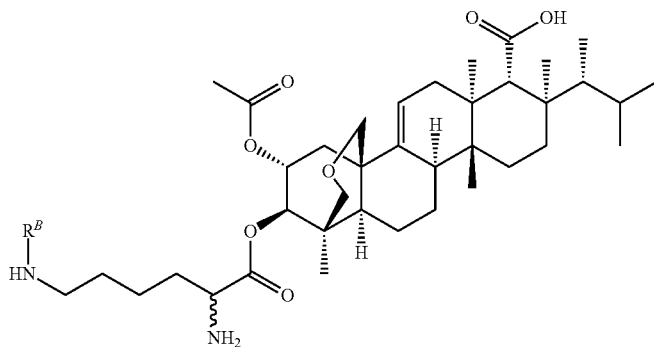
(IB)

| Example # | Compound Name | R$^B$ | Mass | $^1$H NMR (400 MHz, MeOH-d4) δ |
|---|---|---|---|---|
| 58 | (1S,2R,3R,4aR,6aS,7R,8R,10aR,10bR,12aR)-3-(acetyloxy)-2-(2-amino-6-(4-tert-butylbenzenesulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | t-Bu–C$_6$H$_4$–SO$_2$– | Calculated for C$_{48}$H$_{74}$N$_2$O$_9$S: 854. Observed: 855 (M + H)$^+$. | 0.72 (s, 3 H) 0.78 (s, 3 H) 0.87 (d, J = 6.54 Hz, 3 H) 0.92 (d, J = 6.54 Hz, 3 H) 1.19 (s, 3 H) 1.23 (s, 3 H) 1.36 (s, 9 H) 1.40-1.61 (m, 11 H) 1.60-1.89 (m, 9 H) 1.98 (s, 3 H) 2.04-2.30 (m, 3 H) 2.39-2.53 (m, 1 H) 2.84 (s, 1 H) 3.50 (s, 5 H) 3.62-3.79 (m, 1 H) 3.99-4.22 (m, 1 H) 4.97-5.10 (m, 1 H) 5.52 (s, 1 H) 5.80-6.01 (m, 1 H) 7.55-7.71 (m, 2 H) 7.73-7.91 (m, 2 H) |
| 59 | (1S,2R,3R,4aR,6aS,7R,8R,10aR,10bR,12aR)-3-(acetyloxy)-2-(2-amino-6-(4-trifluoromethylbenzenesulfonyl-amino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | F$_3$C–C$_6$H$_4$–SO$_2$– | Calculated for C$_{45}$H$_{65}$F$_3$N$_2$O$_9$S: 866. Observed: 867 (M + H)$^+$. | 0.71-0.73 (m, J = 4.25 Hz, 3 H) 0.78 (s, 3 H) 0.87 (d, J = 6.54 Hz, 3 H) 0.92 (d, J = 6.69 Hz, 3 H) 1.19 (s, 3 H) 1.23 (s, 3 H) 1.25-1.31 (m, 4 H) 1.39-1.68 (m, 9 H) 1.72-1.90 (m, 8 H) 1.99 (s, 3 H) 2.06-2.28 (m, 2 H) 2.37-2.55 (m, 1 H) 2.90 (s, 1 H) 3.42-3.60 (m, 4 H) 3.57-3.78 (m, 1 H) 3.95-4.20 (m, 1 H) 4.94-5.07 (m, 2 H) 5.51 (s, 1 H) 5.76-6.00 (m, 1 H) 7.85-8.01 (m, 2 H) 8.00-8.15 (m, 2 H) |
| 60 | (1S,2R,3R,4aR,6aS,7R,8R,10aR,10bR,12aR)-3-(acetyloxy)-2-(2-amino-6-(4-fluorobenzenesulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | F–C$_6$H$_4$–SO$_2$– | Calculated for C$_{44}$H$_{65}$FN$_2$O$_9$S: 816. Observed: 817 (M + H)$^+$. | 0.69-0.75 (m, J = 4.44 Hz, 3 H) 0.78 (s, 3 H) 0.87 (d, J = 6.59 Hz, 3 H) 0.92 (d, J = 6.69 Hz, 3 H) 1.19 (s, 3 H) 1.23 (s, 3 H) 1.25-1.32 (m, 3 H) 1.39-1.64 (m, 9 H) 1.60-1.90 (m, 8 H) 1.99 (s, 3 H) 2.07-2.32 (m, 3 H) 2.35-2.57 (m, 1 H) 2.86 (s, 1 H) 3.40-3.60 (m, 5 H) 3.58-3.76 (m, 1 H) 3.98-4.16 (m, 1 H) 4.96-5.10 (m, 1 H) 5.52 (s, 1 H) 5.77-6.00 (m, 1 H) 7.15-7.46 (m, 2 H) 7.70-8.06 (m, 2 H) |

-continued

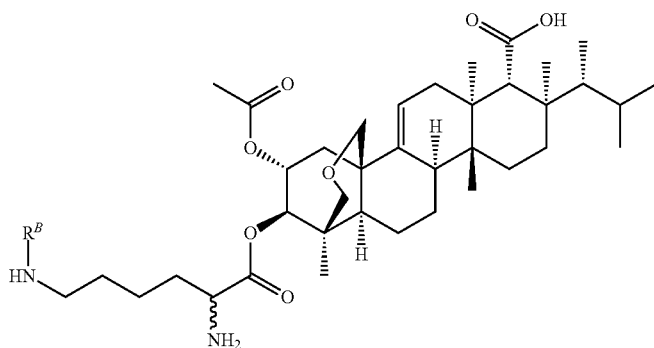

(IB)

| Example # | Compound Name | $R^B$ | Mass | $^1$H NMR (400 MHz, MeOH-d4) δ |
|---|---|---|---|---|
| 61 | (1S,2R,3R,4aR,6aS,7R,8R,10aR,10bR,12aR)-3-(acetyloxy)-2-(2-amino-6-(4-bromobenzenesulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | 4-bromophenylsulfonyl | Calculated for $C_{44}H_{65}BrN_2O_9S$: 877. Observed: 800 $(M - Br)^+$. | 0.70-0.73 (m, J = 4.83 Hz, 3 H) 0.78 (s, 3 H) 0.87 (d, J = 6.64 Hz, 3 H) 0.92 (d, J = 6.78 Hz, 3 H) 1.19 (s, 3 H) 1.23 (s, 3 H) 1.25-1.30 (m, 3 H) 1.39-1.61 (m, 10 H) 1.69-1.91 (m, 7 H) 1.98 (s, 3 H) 2.19 (s, 3 H) 2.40-2.58 (m, 1 H) 2.86 (s, 1 H) 3.39-3.61 (m, 5 H) 3.62-3.76 (m, 1 H) 3.95-4.13 (m, 1 H) 4.98-5.12 (m, 1 H) 5.52 (s, 1 H) 5.74-6.01 (m, 1 H) 7.45-7.66 (m, 2 H) 7.79-7.96 (m, 2 H) |
| 62 | (1S,2R,3R,4aR,6aS,7R,8R,10aR,10bR,12aR)-3-(acetyloxy)-2-(2-amino-6-(4-methoxybenzenesulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | 4-methoxyphenylsulfonyl | Calculated for $C_{45}H_{68}N_2O_{10}S$: 828. Observed: 829 $(M + H)^+$. | 0.70-0.73 (m, J = 7.42 Hz, 3 H) 0.78 (s, 3 H) 0.87 (d, J = 6.54 Hz, 3 H) 0.92 (d, J = 6.64 Hz, 3 H) 1.19 (s, 3 H) 1.22 (s, 3 H) 1.25-1.35 (m, 4 H) 1.37-1.66 (m, 10 H) 1.71-1.89 (m, 8 H) 1.98 (s, 3 H) 2.04-2.26 (m, 3 H) 2.38-2.56 (m, 1 H) 2.86 (s, 1 H) 3.40-3.59 (m, 3 H) 3.59-3.77 (m, 1 H) 3.88 (s, 3 H) 3.97-4.20 (m, 1 H) 4.94-5.14 (m, 1 H) 5.42-5.64 (m, 1 H) 5.77-6.03 (m, 1 H) 7.08 (d, J = 8.74 Hz, 2 H) 7.63-7.99 (m, 2 H) |
| 63 | (1S,2R,3R,4aR,6aS,7R,8R,10aR,10bR,12aR)-3-(acetyloxy)-2-(2-amino-6-(3,5-dimethylisoxazole-4-sulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | 3,5-dimethylisoxazol-4-ylsulfonyl | Calculated for $C_{43}H_{69}N_3O_{10}S$: 819. Observed: 820 $(M + H)^+$. | 0.70-0.75 (m, J = 8.00 Hz, 3 H) 0.76-0.79 (m, 3 H) 0.87 (d, J = 6.64 Hz, 4 H) 0.92 (d, J = 6.74 Hz, 3 H) 1.19 (s, 3 H) 1.23 (s, 3 H) 1.25-1.35 (m, 6 H) 1.38-1.69 (m, 8 H) 1.68-1.91 (m, 9 H) 1.99 (s, 3 H) 2.06-2.28 (m, 4 H) 2.37-2.60 (m, 4 H) 2.86 (s, 1 H) 3.43-3.60 (m, 5 H) 3.60-3.76 (m, 1 H) 3.95-4.20 (m, 1 H) 5.02 (d, J = 8.83 Hz, 1 H) 5.52 (s, 1 H) 5.83-5.99 (m, 1 H) |

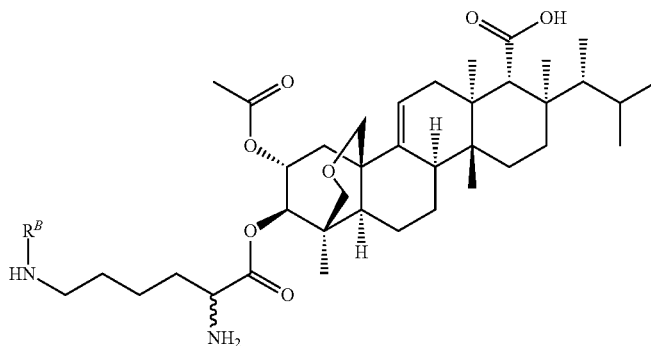

(IB)

| Example # | Compound Name | $R^B$ | Mass | $^1$H NMR (400 MHz, MeOH-d4) δ |
|---|---|---|---|---|
| 64 | (1S,2R,3R,4aR,6aS,7R,8R,10aR,10bR,12aR)-3-(acetyloxy)-2-(2-amino-6-methanesulfonylamino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | Me–S(=O)(=O)– | Calculated for $C_{39}H_{64}N_2O_9S$: 736. Observed: 737 $(M + H)^+$. | 0.73 (s, 3 H) 0.78 (s, 3 H) 0.87 (d, J = 6.59 Hz, 3 H) 0.91 (d, J = 6.69 Hz, 4 H) 1.19 (s, 3 H) 1.22 (s, 3 H) 1.26-1.33 (m, 3 H) 1.38-1.67 (m, 9 H) 1.67-1.93 (m, 7 H) 1.99 (s, 3 H) 2.05-2.28 (m, 3 H) 2.41-2.54 (m, 1 H) 2.86 (s, 1 H) 2.93 (s, 3 H) 3.50 (s, 5 H) 3.58-3.78 (m, 1 H) 4.05-4.18 (m, 1 H) 4.94-5.08 (m, 1 H) 5.52 (s, 1 H) 5.81-5.99 (m, 1 H) |
| 65 | (1S,2R,3R,4aR,6aS,7R,8R,10aR,10bR,12aR)-3-(acetyloxy)-2-(2-amino-6-ethanesulfonylamino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | Et–S(=O)(=O)– | Calculated for $C_{40}H_{66}N_2O_9S$: 750. Observed: 751 $(M + H)^+$. | 0.73 (s, 3 H) 0.78 (s, 3 H) 0.87 (d, J = 6.39 Hz, 3 H) 0.91 (d, J = 6.54 Hz, 3 H) 1.19 (s, 3 H) 1.22 (s, 3 H) 1.23-1.36 (m, 7 H) 1.40-1.67 (m, 10 H) 1.77-1.96 (m, 8 H) 1.99 (s, 3 H) 2.16 (s, 3 H) 2.41-2.54 (m, 1 H) 2.86 (s, 1 H) 3.50 (s, 5 H) 3.64-3.77 (m, 1 H) 3.95-4.23 (m, 1 H) 4.97-5.08 (m, 1 H) 5.51 (s, 1 H) 5.80-6.03 (m, 1 H) |
| 66 | (1S,2R,3R,4aR,6aS,7R,8R,10aR,10bR,12aR)-3-(acetyloxy)-2-(2-amino-6-propanesulfonylamino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | n-$C_3H_7$–S(=O)(=O)– | Calculated for $C_{41}H_{68}N_2O_9S$: 764. Observed: 765 $(M + H)^+$. | 0.73 (s, 3 H) 0.87 (d, J = 6.59 Hz, 2 H) 0.91 (d, J = 6.64 Hz, 2 H) 1.03-1.10 (m, 3 H) 1.19 (s, 3 H) 1.22 (s, 3 H) 1.23-1.32 (m, 4 H) 1.37-1.66 (m, 12 H) 1.69-1.88 (m, 9 H) 1.99 (s, 3 H) 2.05-2.28 (m, 4 H) 2.34-2.58 (m, 1 H) 2.86 (s, 1 H) 2.97-3.11 (m, 3 H) 3.47 (s, 5 H) 3.63-3.82 (m, 1 H) 3.93-4.22 (m, 1 H) 4.95-5.11 (m, 1 H) 5.51 (s, 1 H) 5.76-6.01 (m, 1 H) |

-continued

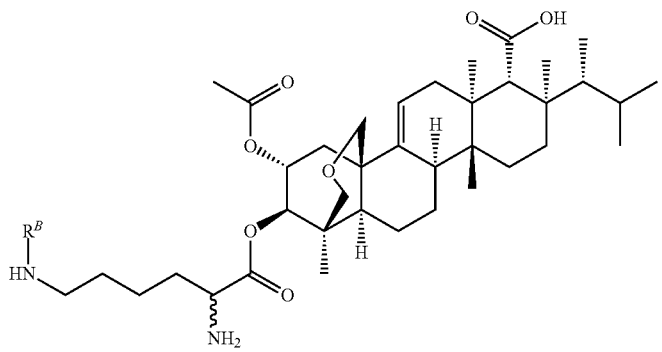

(IB)

| Example # | Compound Name | $R^B$ | Mass | $^1$H NMR (400 MHz, MeOH-d4) δ |
|---|---|---|---|---|
| 67 | (1S,2R,3R,4aR,6aS,7R,8R,10aR,10bR,12aR)-3-(acetyloxy)-2-(2-amino-6-(3-chloropropane-1-sulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | Cl-CH$_2$CH$_2$CH$_2$-S(O)$_2$- (3-chloropropylsulfonyl) | Calculated for $C_{41}H_{67}ClN_2O_9S$: 798. Observed: 799 (M + H)$^+$. | 0.73 (s, 3 H) 0.78 (s, 3 H) 0.87 (d, J = 6.49 Hz, 3 H) 0.92 (d, J = 6.69 Hz, 3 H) 1.22 (s, 3 H) 1.24-1.33 (m, 4 H) 1.37-1.67 (m, 12 H) 1.73-1.90 (m, 9 H) 1.99 (s, 3 H) 2.19 (s, 3 H) 2.37-2.56 (m, 1 H) 2.86 (s, 1 H) 3.13-3.26 (m, 2 H) 3.37-3.57 (m, 5 H) 3.66-3.81 (m, 3 H) 4.02-4.18 (m, 1 H) 4.97-5.12 (m, 1 H) 5.52 (s, 1 H) 5.82-6.04 (m, 1 H) |
| 68 | (1S,2R,3R,4aR,6aS,7R,8R,10aR,10bR,12aR)-3-(acetyloxy)-2-(2-amino-6-(3,5-bis-trifluoromethylbenzenesulfonyl-amino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | 3,5-bis(trifluoromethyl)phenylsulfonyl | Calculated for $C_{46}H_{64}F_6N_2O_9S$: 934. Observed: 935 (M + H)$^+$. | 0.72 (s, 3 H) 0.78 (s, 3 H) 0.87 (d, J = 6.64 Hz, 3 H) 0.92 (d, J = 6.69 Hz, 3 H) 1.19 (s, 3 H) 1.23 (s, 3 H) 1.25-1.32 (m, 3 H) 1.36-1.66 (m, 9 H) 1.82 (s, 8 H) 1.99 (s, 3 H) 2.07-2.26 (m, 3 H) 2.39-2.51 (m, 1 H) 2.86 (s, 1 H) 3.50 (s, 5 H) 3.62-3.74 (m, 1 H) 3.96-4.14 (m, 1 H) 4.96-5.10 (m, 1 H) 5.51 (s, 1 H) 5.83-5.94 (m, 1 H) 8.29 (s, 1 H) 8.38 (s, 1 H) 8.41 (s, 1 H) |
| 69 | (1S,2R,3R,4aR,6aS,7R,8R,10aR,10bR,12aR)-3-(acetyloxy)-2-(2-amino-6-(3-trifluoromethylbenzenesulfonyl-amino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | 3-(trifluoromethyl)phenylsulfonyl | Calculated for $C_{45}H_{65}F_3N_2O_9S$: 866. Observed: 867 (M + H)$^+$. | 0.72 (s, 3 H) 0.78 (s, 3 H) 0.87 (d, J = 6.59 Hz, 3 H) 0.92 (d, J = 6.74 Hz, 3 H) 1.19 (s, 3 H) 1.23 (s, 3 H) 1.26 (s, 3 H) 1.39-1.61 (m, 8 H) 1.66-1.89 (m, 9 H) 1.98 (s, 3 H) 2.11 (s, 3 H) 2.35-2.53 (m, 1 H) 2.76-2.95 (m, 1 H) 3.37-3.56 (m, 5 H) 3.59-3.76 (m, 1 H) 3.97-4.17 (m, 1 H) 4.96-5.15 (m, 1 H) 5.41-5.61 (m, 1 H) 5.81-5.97 (m, 1 H) 7.71-7.86 (m, 1 H) 7.91-8.01 (m, 1 H) 8.07-8.21 (m, 2 H) |

-continued

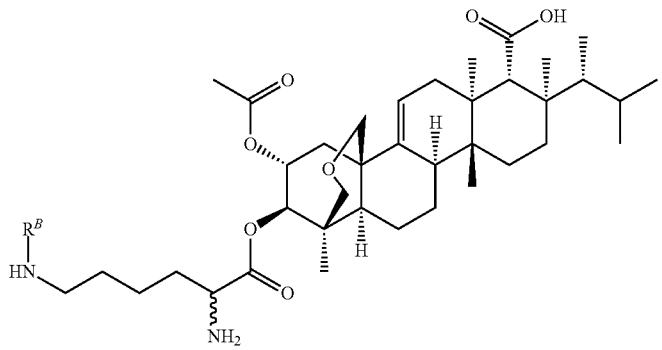

(IB)

| Example # | Compound Name | $R^B$ | Mass | $^1$H NMR (400 MHz, MeOH-d4) δ |
|---|---|---|---|---|
| 70 | (1S,2R,3R,4aR,6aS,7R,8R,10aR,10bR,12aR)-3-(acetyloxy)-2-(6-(4-acetylamino-benzenesulfonylamino)-2-amino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | AcHN-C6H4-SO2- | Calculated for $C_{46}H_{69}N_3O_{10}S$: 855. Observed: 856 (M + H)$^+$. | 0.72 (s, 3 H) 0.78 (s, 3 H) 0.87 (d, J = 6.54 Hz, 3 H) 0.91 (d, J = 6.64 Hz, 3 H) 1.19 (s, 3 H) 1.22 (s, 3 H) 1.25-1.31 (m, 3 H) 1.40-1.67 (m, 9 H) 1.70-1.90 (m, 8 H) 1.99 (s, 3 H) 2.08-2.15 (m, 3 H) 2.16 (s, 3 H) 2.37-2.56 (m, 1 H) 2.86 (s, 1 H) 3.49 (s, 5 H) 3.56-3.75 (m, 1 H) 3.96-4.15 (m, 1 H) 4.96-5.06 (m, 2 H) 5.51 (s, 1 H) 5.76-6.03 (m, 1 H) 7.68-7.87 (m, 4 H) |
| 71 | (1S,2R,3R,4aR,6aS,7R,8R,10aR,10bR,12aR)-3-(acetyloxy)-2-(2-amino-6-(3-chloro-4-fluorobenzenesulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | 3-Cl-4-F-C6H3-SO2- | Calculated for $C_{44}H_{64}ClFN_2O_9S$: 850. Observed: 851 (M + H)$^+$. | 0.71-0.73 (m, J = 4.25 Hz, 3 H) 0.78 (s, 3 H) 0.87 (d, J = 6.59 Hz, 3 H) 0.92 (d, J = 6.69 Hz, 3 H) 1.19 (s, 3 H) 1.23 (s, 3 H) 1.25-1.34 (m, 3 H) 1.38-1.64 (m, 9 H) 1.70-1.90 (m, 8 H) 1.99 (s, 3 H) 2.07-2.28 (m, 3 H) 2.39-2.58 (m, 1 H) 2.86 (s, 1 H) 3.41-3.63 (m, 5 H) 3.63-3.80 (m, 1 H) 3.95-4.23 (m, 1 H) 4.94-5.09 (m, 1 H) 5.52 (s, 1 H) 5.83-6.04 (m, 1 H) 7.22-7.44 (m, 1 H) 7.77-8.05 (m, 2 H) |
| 72 | (1S,2R,3R,4aR,6aS,7R,8R,10aR,10bR,12aR)-3-(acetyloxy)-2-(2-amino-6-(toluene-2-sulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | 2-Me-C6H4-SO2- | Calculated for $C_{45}H_{68}N_2O_9S$: 812. Observed: 813 (M + H)$^+$. | 0.74 (s, 3 H) 0.78 (s, 3 H) 0.87 (d, J = 6.64 Hz, 3 H) 0.90-0.93 (m, J = 6.74 Hz, 3 H) 1.19 (s, 3 H) 1.23 (s, 3 H) 1.25-1.34 (m, 3 H) 1.56 (d, J = 32.51 Hz, 8 H) 1.66-1.90 (m, 8 H) 2.00 (s, 3 H) 2.02-2.29 (m, 4 H) 2.34-2.54 (m, 1 H) 2.76-3.09 (m, 4 H) 3.47 (s, 5 H) 3.60-3.80 (m, 1 H) 3.94-4.19 (m, 1 H) 4.98-5.11 (m, 1 H) 5.51 (s, 1 H) 5.93 (s, 1 H) 7.28-7.53 (m, 4 H) |

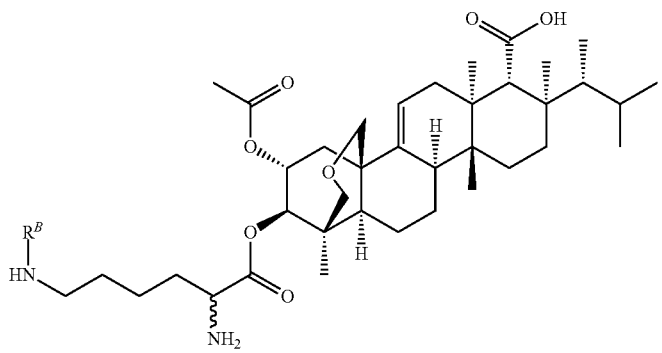

(IB)

| Example # | Compound Name | $R^B$ | Mass | $^1$H NMR (400 MHz, MeOH-d4) δ |
|---|---|---|---|---|
| 73 | (1S,2R,3R,4aR,6aS,7R,8R, 10aR,10bR,12aR)-3-(acetyloxy)-2-(2-amino-6-(3,4-dimethoxy-benzenesulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | 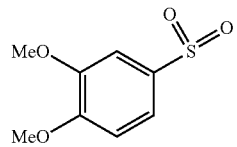 | Calculated for $C_{46}H_{70}N_2O_{11}S$: 858. Observed: 859 $(M + H)^+$. | 0.72 (s, 3 H) 0.78 (s, 3 H) 0.87 (d, J = 6.64 Hz, 3 H) 0.92 (d, J = 6.74 Hz, 3 H) 1.19 (s, 4 H) 1.22 (s, 3 H) 1.28 (s, 3 H) 1.55 (s, 8 H) 1.74-1.89 (m, 7 H) 1.99-1.99 (m, 3 H) 2.17 (s, 3 H) 2.40-2.56 (m, 2 H) 2.86 (s, 1 H) 3.49 (s, 5 H) 3.60-3.75 (m, 1 H) 3.90 (s, 3 H) 3.90 (s, 3 H) 4.12 (s, 1 H) 5.01 (s, 1 H) 5.52 (s, 1 H) 5.76-6.02 (m, 1 H) 7.10 (d, J = 8.49 Hz, 1 H) 7.36 (dd, J = 6.47, 1.93 Hz, 1 H) 7.40-7.49 (m, 1 H) |

Example 74

Benzyl (1S,2R,3R,4aR,6aS,7R,8R,10aR,10bR,12aR)-3-(acetyloxy)-2-(2-aminoacetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylate

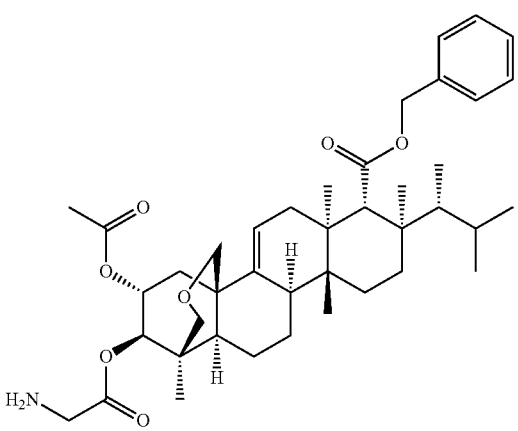

Fmoc-Gly-OH (4.3 mmol), DCC (4.3 mmol), and DMAP (4.3 mmol) were added to a solution of Intermediate 1 (1.1 g) in THF (16 mL). The reaction mixture was stirred at RT for 1.5 hours. The reaction mixture was filtered over silica gel that was washed with EtOAc. The filtrate was concentrated, and the residue was purified by flash chromatography (silica gel; 95:5 then 90:10 heptane:EtOAc). The purified material (1.55 g) was dissolved in DMF (18 mL), and piperidine (2 mL) was added. The reaction solution was stirred at RT for 45 minutes and judged complete by TLC. Ice was added to the reaction solution, and the reaction was partitioned by addition of $H_2O$ (80 mL) and EtOAc (100 mL). The organic phase was washed with $H_2O$ and saturated aqueous NaCl before being dried over $Na_2SO_4$ and concentrated. The residue was purified by flash chromatography (silica gel, 50:50 heptane:EtOAc, then 90:10 EtOAc:MeOH) to yield the title compound (1.1 g).

Example 75

(1S, 2R, 3R, 4aR, 6aS, 7R, 8R, 10aR, 10bR, 12aR)-3-(acetyloxy)-2-(2,2-dimethyl-propylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid

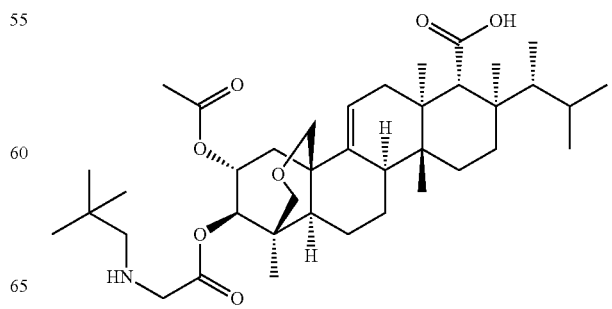

TEA (25 μL) and HOAc (10 μL) were added to a solution of the compound from Example 74 (40 mg, 0.06 mmol) in DMC (2 mL). Trimethylacetaldehyde (0.07 mmol) was added, and the reaction solution was stirred for 5 minutes. Sodium triacetoxyborohydride (0.18 mmol) was added, and the reaction was stirred at RT for 16 hours. The reaction was judged complete by TLC analysis, and the reaction was quenched by the addition of several drops of $H_2O$. The reaction solution was filtered over a small pad of silica gel and CHEMTUBE hydromatrix, and the filtrate was concentrated. The residue was dissolved in MeOH and purified by reverse-phase HPLC (70:30 to 100:0 MeOH:$H_2O$). The product was collected from the relevant fractions and dissolved in MeOH (1.5 mL). PdOH (130 mg) and cyclohexadiene (180 μL) were added, and the reactions were stirred at 50° C. for 3 hours. The reaction was judged complete by TLC analysis. The reaction mixture was cooled to RT and filtered over CELITE. The filtrate was concentrated and purified by reverse-phase HPLC (70:30 to 100:0 MeOH:$H_2O$) to yield the title compound (14.2 mg). Calculated for $C_{39}H_{63}NO_7$: 657. Observed: 658 $(M+H)^+$. $^1H$ NMR (400 MHz, $CDCl_3$) δ ppm 0.63 (s, 3 H) 0.69 (s, 3 H) 0.72 (d, J=7.14 Hz, 3 H) 0.80 (d, J=6.65 Hz, 3 H) 0.86 (d, J=6.81 Hz, 3 H) 0.91 (s, 9 H) 1.10 (s, 3 H) 1.16 (s, 3 H) 1.18-1.28 (m, 3 H) 1.29-1.48 (m, 3 H) 1.48-1.68 (m, 3 H) 1.68-1.79 (m, 3 H) 1.86-1.91 (m, 1 H) 1.93 (s, 3 H) 1.96-2.04 (m, 1 H) 2.06-2.17 (m, 1 H) 2.28-2.37 (m, 2 H) 2.37-2.47 (m, 1 H) 2.82 (s, 1 H) 3.27-3.46 (m, 4 H) 3.49 (d, 1 H) 3.66 (d, J=12.03 Hz, 1 H) 4.92 (d, J=9.28 Hz, 1 H) 5.40 (d, J=4.01 Hz, 1 H) 5.75-5.89 (m, 1 H).

In a similar manner as described in Example 75, using the compound described in Example 74 and an appropriate aldehyde, the following compounds of formula (IC) were prepared, where the $R^C$ group is connected to the remainder of the molecule via the right-most bond shown in the $R^C$ group:

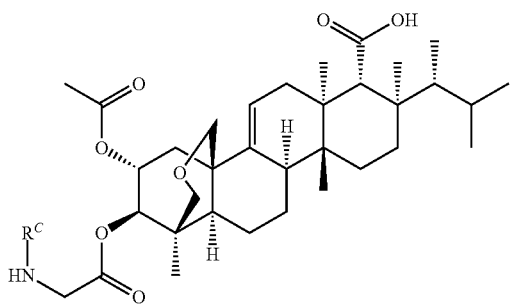

(IC)

| Example # | Compound Name | $R^C$ | Mass | $^1H$ NMR (400 MHz, MeOH-d4) δ |
|---|---|---|---|---|
| 76 | (1S,2R,3R,4aR,6aS,7R,8R,10aR,10bR,12aR)-3-(acetyloxy)-2-(2-[(tetrahydro-furan-2-ylmethyl)-amino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | | Calculated for $C_{39}H_{61}NO_8$: 671. Observed: 672 $(M + H)^+$. | 0.64 (s, 3 H) 0.69 (s, 3 H) 0.72 (d, J = 7.14 Hz, 3 H) 0.80 (d, J = 6.65 Hz, 3 H) 0.86 (d, J = 6.76 Hz, 3 H) 1.10 (s, 3 H) 1.16 (s, 3 H) 1.17-1.28 (m, 3 H) 1.29-1.48 (m, 3 H) 1.48-1.80 (m, 8 H) 1.86-1.91 (m, 1 H) 1.94 (s, 3 H) 1.97-2.15 (m, 4 H) 2.34-2.44 (m, 1 H) 2.48-2.56 (m, 1 H) 2.68-2.77 (m, 1 H) 2.83 (s, 1 H) 3.28-3.89 (m, 9 H) 4.91 (d, J = 9.06 Hz, 1 H) 5.40 (s, 1 H) 5.76-5.88 (m, 1 H) |
| 77 | (1S,2R,3R,4aR,6aS,7R,8R,10aR,10bR,12aR)-3-(acetyloxy)-2-(2-[2-(4-fluoro-phenyl)-1-methyl-ethylamino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | | Calculated for $C_{43}H_{62}FNO_7$: 723. Observed: 724 $(M + H)^+$. | 0.61 (s, 2 H) 0.69 (s, 3 H) 0.72 (d, J = 7.14 Hz, 3 H) 0.80 (d, J = 6.65 Hz, 3 H) 0.86 (d, J = 6.76 Hz, 3 H) 1.02-1.08 (m, 3 H) 1.10 (s, 3 H) 1.16 (s, 3 H) 1.18-1.28 (m, 3 H) 1.29-1.47 (m, 3 H) 1.48-1.67 (m, 3 H) 1.68-1.79 (m, 3 H) 1.86-1.89 (m, 2 H) 1.90 (s, 3 H) 1.95-2.03 (m, 1 H) 2.05-2.15 (m, 1 H) 2.34-2.46 (m, 1 H) 2.56-2.67 (m, 1 H) 2.82 (s, 2 H) 2.92-3.03 (m, 1 H) 3.24-3.66 (m, 6 H) 4.89 (dd, J = 8.98, 5.80 Hz, 1 H) 5.40 (s, 1 H) 5.74-5.89 (m, 1 H) 6.89-7.00 (m, 2 H) 7.05-7.17 (m, 2 H) |

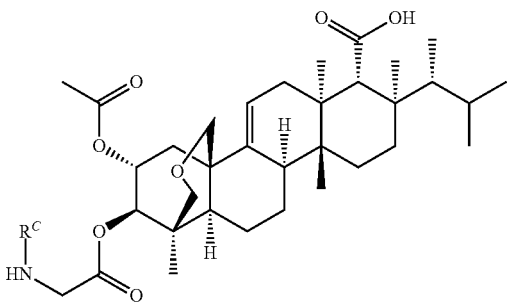

(IC)

| Example # | Compound Name | $R^C$ | Mass | $^1$H NMR (400 MHz, MeOH-d4) δ |
|---|---|---|---|---|
| 78 | (1S,2R,3R,4aR,6aS,7R,8R,10aR,10bR,12aR)-3-(acetyloxy)-2-(2-(tetrahydro-pyran-4-ylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | (tetrahydropyran-4-yl) | Calculated for $C_{39}H_{61}NO_8$: 671. Observed: 672 $(M + H)^+$. | 0.62 (s, 3 H) 0.69 (s, 3 H) 0.72 (d, J = 7.14 Hz, 3 H) 0.80 (d, J = 6.70 Hz, 3 H) 0.86 (d, J = 6.76 Hz, 3 H) 1.10 (s, 3 H) 1.16 (s, 3 H) 1.17-1.28 (m, 3 H) 1.29-1.47 (m, 4 H) 1.48-1.63 (m, 3 H) 1.63-1.81 (m, 5 H) 1.85-1.89 (m, 1 H) 1.93 (s, 3 H) 1.96-2.04 (m, 1 H) 2.06-2.16 (m, 1 H) 2.34-2.47 (m, 2 H) 2.61-2.71 (m, 1 H) 2.82 (s, 1 H) 3.26-3.42 (m, 4 H) 3.42-3.46 (m, 2 H) 3.46-3.52 (m, 1 H) 3.64 (d, J = 11.98 Hz, 1 H) 3.88-4.01 (m, 2 H) 4.91 (d, J = 8.95 Hz, 1 H) 5.40 (d, J = 5.60 Hz, 1 H) 5.74-5.87 (m, 1 H) |
| 79 | (1S,2R,3R,4aR,6aS,7R,8R,10aR,10bR,12aR)-3-(acetyloxy)-2-(2-isopropyl aminoacetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | isopropyl (Me, Me) | Calculated for $C_{37}H_{59}NO_7$: 629. Observed: 630 $(M + H)^+$. | 0.65 (s, 3 H) 0.70 (s, 3 H) 0.73 (d, J = 7.09 Hz, 3 H) 0.81 (d, J = 6.65 Hz, 3 H) 0.86 (d, J = 6.81 Hz, 3 H) 1.10 (s, 3 H) 1.12-1.18 (m, 9 H) 1.17-1.26 (m, 3 H) 1.27-1.69 (m, 6 H) 1.69-1.80 (m, 3 H) 1.85-1.90 (m, 1 H) 1.93 (s, 3 H) 1.97-2.04 (m, 1 H) 2.06-2.15 (m, 1 H) 2.35-2.46 (m, 1 H) 2.84 (s, 1 H) 3.28-3.54 (m, 4 H) 3.60-3.71 (m, 1 H) 3.72-3.82 (m, 1 H) 4.86-4.96 (m, 1 H) 5.37-5.44 (m, 1 H) 5.74-5.90 (m, 1 H) |
| 80 | (1S,2R,3R,4aR,6aS,7R,8R,10aR,10bR,12aR)-3-(acetyloxy)-2-(2-(2-methyl-tetrahydro-furan-3-ylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | (2-methyl-tetrahydrofuran-3-yl) | Calculated for $C_{39}H_{61}NO_8$: 671. Observed: 672 $(M + H)^+$. | 0.63 (d, J = 1.65 Hz, 3 H) 0.69 (s, 3 H) 0.72 (d, J = 7.14 Hz, 3 H) 0.80 (d, J = 6.65 Hz, 3 H) 0.86 (d, J = 6.81 Hz, 3 H) 1.10 (s, 3 H) 1.16 (s, 3 H) 1.17-1.29 (m, J = 6.48 Hz, 6 H) 1.29-1.47 (m, 3 H) 1.48-1.62 (m, 2 H) 1.63-1.84 (m, 5 H) 1.85-1.90 (m, 1 H) 1.93 (d, J = 1.81 Hz, 3 H) 1.96-2.17 (m, 3 H) 2.35-2.45 (m, 1 H) 2.82 (s, 1 H) 3.13-3.22 (m, 1 H) 3.26-3.52 (m, 5 H) 3.58-3.77 (m, 2 H) 3.84-4.00 (m, 2 H) 4.91 (d, J = 9.23 Hz, 1 H) 5.40 (d, J = 5.55 Hz, 1 H) 5.76-5.87 (m, 1 H) |

(IC)

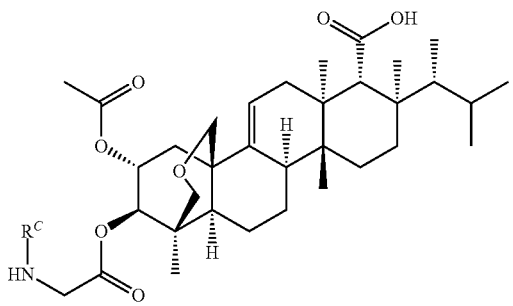

| Example # | Compound Name | $R^C$ | Mass | $^1$H NMR (400 MHz, MeOH-d4) δ |
|---|---|---|---|---|
| 81 | (1S,2R,3R,4aR,6aS,7R, 8R,10aR,10bR,12aR)-3-(acetyloxy)-2-(2-(1-methyl-3-methylsulfanyl-propylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid | MeS—⋯—Me | Calculated for $C_{39}H_{63}NO_7S$: 689. Observed: 690 $(M + H)^+$. | 0.65 (s, 3 H) 0.72 (s, 3 H) 0.75 (d, J = 7.14 Hz, 3 H) 0.83 (d, J = 6.65 Hz, 3 H) 0.89 (d, J = 6.71 Hz, 3 H) 1.13 (s, 3 H) 1.19 (s, 3 H) 1.21-1.31 (m, 4 H) 1.32-1.51 (m, 3 H) 1.50-1.71 (m, 3 H) 1.71-1.80 (m, 3 H) 1.89-1.93 (m, 1 H) 1.94 (s, 3 H) 1.98-2.02 (m, 1 H) 2.11-2.20 (m, 1 H) 2.26-2.34 (m, 3 H) 2.40-2.58 (m, 2 H) 2.65-2.74 (m, 1 H) 2.83 (s, 1 H) 3.28-3.45 (m, 7 H) 3.51 (d, 1 H) 3.67 (d, J = 11.72 Hz, 1 H) 4.88-4.96 (m, 1 H) 5.44 (d, J = 5.68 Hz, 1 H) 5.77-5.89 (m, 1 H) |
| 82 | (1S,2R,3R,4aR,6aS,7R, 8R,10aR,10bR,12aR)-3-(acetyloxy)-2-(2-(4-diethylamino-1-methyl-butylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid | $Et_2N$—⋯—Me | Calculated for $C_{43}H_{72}N_2O_7$: 728. Observed: 729 $(M + H)^+$. | 0.60 (s, 3 H) 0.68 (s, 3 H) 0.71 (d, J = 7.14 Hz, 3 H) 0.78 (d, J = 6.65 Hz, 3 H) 0.84 (d, J = 6.70 Hz, 3 H) 0.99 (dd, J = 6.18, 2.01 Hz, 3 H) 1.10 (s, 3 H) 1.12 (d, J = 5.66 Hz, 3 H) 1.16 (s, 6 H) 1.18-1.34 (m, 3 H) 1.34-1.45 (m, 3 H) 1.46-1.77 (m, 6 H) 1.90 (s, 3 H) 1.92-2.02 (m, 2 H) 2.10-2.22 (m, 2 H) 2.34-2.45 (m, 1 H) 2.53-2.63 (m, 1 H) 2.63-2.71 (m, 2 H) 2.73 (s, 1 H) 2.75-2.91 (m, 4 H) 3.27-3.41 (m, 4 H) 3.44-3.52 (m, 1 H) 3.63 (d, J = 11.81 Hz, 1 H) 4.21-4.70 (m, 3 H) 4.87 (d, J = 9.06 Hz, 1 H) 5.39 (d, J = 4.29 Hz, 1 H) 5.73-5.86 (m, 1 H) |
| 83 | (1S,2R,3R,4aR,6aS,7R, 8R,10aR,10bR,12aR)-3-(acetyloxy)-2-[(1-Methyl-pyrrolidin-2-ylmethyl)-amino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid | (1-methyl-pyrrolidine with ethyl) | Calculated for $C_{40}H_{64}N_2O_7$: 684. Observed: 685 $(M + H)^+$. | 0.58-0.61 (m, 3 H) 0.62 (s, 3 H) 0.65 (d, J = 7.03 Hz, 3 H) 0.73 (d, J = 6.32 Hz, 3 H) 0.79 (d, J = 6.48 Hz, 3 H) 1.03 (s, 3 H) 1.08 (s, 3 H) 1.10-1.23 (m, 3 H) 1.22-1.53 (m, 6 H) 1.53-1.73 (m, 5 H) 1.80-1.87 (m, 1 H) 1.88 (s, 3 H) 1.90-1.98 (m, 2 H) 2.00-2.22 (m, 3 H) 2.29-2.40 (m, 1 H) 2.57-2.64 (m, 1 H) 2.71 (s, 3 H) 2.74-2.83 (m, 1 H) 2.97-3.36 (m, 6 H) 3.38-3.46 (m, 1 H) 3.54-3.80 (m, 4 H) 4.86 (d, J = 8.90 Hz, 1 H) 5.32-5.37 (m, 1 H) 5.67-5.78 (m, 1 H) |

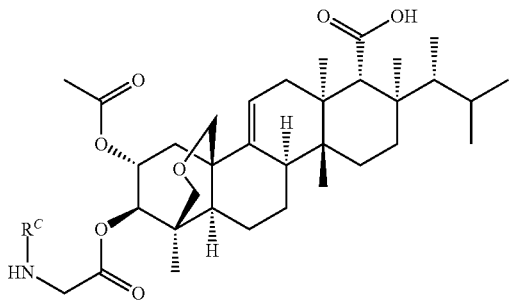

(IC)

| Example # | Compound Name | $R^C$ | Mass | $^1$H NMR (400 MHz, MeOH-d4) δ |
|---|---|---|---|---|
| 84 | (1S,2R,3R,4aR,6aS,7R,8R,10aR,10bR,12aR)-3-(acetyloxy)-2-(2-(1-methyl-piperidin-4-ylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | MeN–(4-methylpiperidine) | Calculated for $C_{40}H_{64}N_2O_7$: 684. Observed: 685 (M + H)$^+$. | 0.61 (s, 3 H) 0.69 (s, 3 H) 0.72 (d, J = 7.09 Hz, 3 H) 0.80 (d, J = 6.65 Hz, 3 H) 0.85 (d, J = 6.81 Hz, 3 H) 1.10 (s, 3 H) 1.15 (s, 3 H) 1.17-1.27 (m, 3 H) 1.29-1.47 (m, 3 H) 1.48-1.62 (m, 3 H) 1.63-1.82 (m, 7 H) 1.86-1.90 (m, 1 H) 1.92 (s, 3 H) 1.96-2.03 (m, 1 H) 2.06-2.16 (m, 1 H) 2.32-2.49 (m, 2 H) 2.71 (s, 3 H) 2.82 (s, 1 H) 2.97-3.05 (m, 1 H) 3.11-3.24 (m, 3 H) 3.28-3.41 (m, 4 H) 3.46-3.51 (m, 1 H) 3.58-3.67 (m, 1 H) 4.88 (d, J = 9.01 Hz, 1 H) 5.39 (s, 1 H) 5.77-5.87 (m, 1 H) |
| 85 | (1S,2R,3R,4aR,6aS,7R,8R,10aR,10bR,12aR)-3-(acetyloxy)-2-(2-(2-methoxy-1-methyl-ethylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | MeO–CH(Me)–CH2– | Calculated for $C_{38}H_{61}NO_8$: 659. Observed: 660 (M + H)$^+$. | 0.63 (d, J = 2.86 Hz, 3 H) 0.69 (s, 3 H) 0.72 (d, J = 7.14 Hz, 3 H) 0.80 (d, J = 6.65 Hz, 3 H) 0.85 (d, J = 6.81 Hz, 3 H) 1.01 (dd, J = 6.43, 1.48 Hz, 3 H) 1.10 (s, 3 H) 1.16 (s, 3 H) 1.17-1.26 (m, 3 H) 1.28-1.47 (m, 3 H) 1.48-1.80 (m, 6 H) 1.85-1.89 (m, 1 H) 1.92 (s, 3 H) 1.96-2.18 (m, 2 H) 2.34-2.49 (m, 1 H) 2.81 (s, 1 H) 2.86-2.97 (m, 1 H) 3.22-3.29 (m, 2 H) 3.31 (d, J = 2.97 Hz, 3 H) 3.33-3.40 (m, 2 H) 3.40-3.59 (m, 3 H) 3.66 (dd, J = 12.06, 4.53 Hz, 1 H) 4.92 (d, J = 9.12 Hz, 1 H) 5.40 (d, J = 5.27 Hz, 1 H) 5.75-5.87 (m, 1 H) |
| 86 | (1S,2R,3R,4aR,6aS,7R,8R,10aR,10bR,12aR)-3-(acetyloxy)-2-(2-(2-methyl-cyclopentylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | 2-methylcyclopentyl | Calculated for $C_{40}H_{63}NO_7$: 669. Observed: 670 (M + H)$^+$. | 0.63 (s, 3 H) 0.69 (s, 3 H) 0.72 (d, J = 7.14 Hz, 3 H) 0.80 (d, J = 6.65 Hz, 3 H) 0.85 (d, J = 6.76 Hz, 3 H) 0.90 (dd, J = 7.03, 1.70 Hz, 3 H) 1.10 (s, 3 H) 1.16 (s, 3 H) 1.18-1.27 (m, 3 H) 1.29-1.47 (m, 5 H) 1.48-1.62 (m, 3 H) 1.62-1.81 (m, 7 H) 1.85-1.89 (m, 1 H) 1.92 (d, J = 2.31 Hz, 3 H) 1.96-2.16 (m, 3 H) 2.36-2.47 (m, 1 H) 2.81 (s, 1 H) 2.86-2.94 (m, 1 H) 3.28-3.53 (m, 5 H) 3.61-3.69 (m, 1 H) 4.91 (dd, J = 9.39, 1.92 Hz, 1 H) 5.40 (d, J = 5.33 Hz, 1 H) 5.76-5.88 (m, 1 H) |

Example 87

(1S, 2R, 3R, 4aR, 6aS, 7R, 8R, 10aR, 10bR, 12aR)-3-(acetyloxy)-2-(2-guanidino-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid

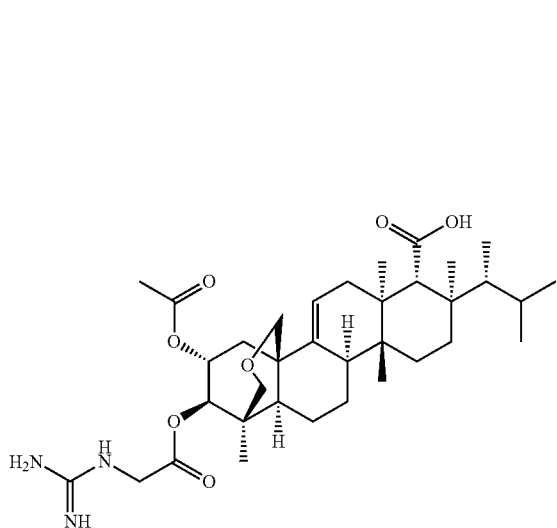

A flask was charged with the compound from Example 74 (76 mg, 0.11 mmol) and 1H-pyrazole carboxamidine (0.11 mmol) in DMF (1.5 mL). The reaction was stirred at RT for 48 hours, and the reaction was judged to be complete by TLC analysis. The reaction was concentrated and the residue was purified by flash chromatography (78:20:2 DCM:MeOH:NH$_4$OH). The desired material (73 mg) was dissolved in MeOH (3 mL) with two drops of DCM added to aid dissolution. PdOH (70 mg) was added, and H$_2$ atmosphere was secured (balloon). The reaction mixture was stirred at RT for 20 minutes and judged complete by TLC. The reaction contents were filtered over a pad of CELITE and concentrated. The residue was purified by flash chromatography (83:15:2 DCM:MeOH:NH$_4$OH) to yield the title compound (26 mg). Calculated for $C_{35}H_{55}N_3O_7$: 629. Observed: 630 (M+H)$^+$. $^1$H NMR (400 MHz, MeOH-d4) δ ppm 0.72 (s, 3 H) 0.77 (s, 3 H) 0.87 (d, J=6.69 Hz, 3 H) 0.91 (d, J=6.83 Hz, 3 H) 1.19 (s, 3 H) 1.23 (s, 3 H) 1.27 (s, 2 H) 1.39-1.65 (m, J=75.51 Hz, 4 H) 1.66-1.87 (m, 5 H) 1.97 (s, 1 H) 2.06-2.25 (m, 3 H) 2.34-2.56 (m, 1 H) 2.86 (s, 1 H) 3.40-3.60 (m, 5 H) 3.69 (d, J=12.01 Hz, 1 H) 4.11 (dd, 2 H) 3.99-4.21 (m, 2 H) 5.50 (s, 1 H) 5.81 (s, 1 H) 6.75 (s, 1 H) 7.97 (s, 1 H) 8.48 (s, 1 H).

Example 88

(1S, 2R, 3R, 4aR, 6aS, 7R, 8R, 10aR, 10bR, 12aR)-3-(acetyloxy)-2-(2-(cyclopropylmethyl-propyl-amino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid

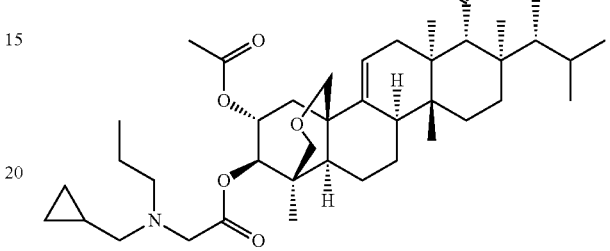

Step 1:

Chloroacetic acid (4.2 mmol), DCC (4.2 mmol), and DMAP (4.2 mmol) were added to a solution of Intermediate 1 (1.03 g) in THF (12 mL). The reaction mixture was stirred at RT for 45 minutes. The reaction mixture was filtered over silica gel that was washed with DCM. The filtrate was concentrated, and the residue was purified by flash chromatography (silica gel; 85:15 then 70:30 heptane:EtOAc) to yield the title compound (1.1 g).

Step 2:

Cyclopropylmethylpropylamine (0.2 mmol) and TEA (0.4 mmol) were added to a solution of the chloroacetate of step 1 (19 mg, 0.027 mmol) in THF (1 mL). The reaction solution was heated to 65° C. for 16 hours, and the reaction was judged complete by TLC analysis. The reaction was cooled and concentrated to dryness. The residue was purified by reverse-phase HPLC (70:30 to 100:0 MeOH:H$_2$O). The product was collected from the relevant fractions and redissolved in MeOH (1.5 mL). PdOH (30 mg) was added, and H$_2$ atmosphere was secured (balloon). The reaction was stirred at RT for 1 hour, and the reaction was judged complete by TLC analysis. The reaction mixture was filtered over CELITE, and the filtrate was concentrated to yield the title compound (8 mg). Calculated for $C_{41}H_{65}NO_7$: 683. Observed: 684 (M+H)$^+$. $^1$H NMR (400 MHz, CDCl$_3$) δ ppm 0.19 (s, 2 H) 0.52-0.60 (m, J=6.04 Hz, 2 H) 0.63 (s, 3 H) 0.69 (s, 3 H) 0.73 (d, J=7.14 Hz, 3 H) 0.80 (d, J=6.65 Hz, 3 H) 0.86 (d, J=6.81 Hz, 3 H) 0.88-0.93 (m, 3 H) 1.10 (s, 3 H) 1.16 (s, 3 H) 1.18-1.27 (m, 4 H) 1.29-1.48 (m, 4 H) 1.48-1.68 (m, 3 H) 1.69-1.81 (m, 4 H) 1.85-1.90 (m, 1 H) 1.92 (s, 3 H) 1.93-1.95 (m, 1 H) 1.97-2.04 (m, 1H) 2.07-2.15 (m, 1 H) 2.38-2.47 (m, 1 H) 2.83 (s, 1 H) 2.84-2.91 (m, 1 H) 3.35 (t, J=12.20 Hz, 2H) 3.45-3.53 (m, 2 H) 3.64 (d, J=11.92 Hz, 1 H) 3.71-3.83 (m, 2 H) 4.89 (d, J=9.39 Hz, 1 H) 5.41 (d, J=4.61 Hz, 1 H) 5.72-5.86 (m, 1 H).

In a similar manner as described in Example 88, using an appropriate amine, the following compounds of formula (ID) were prepared, where the R$^D$ group is connected to the remainder of the molecule via a bond to the right-most N shown in the R$^D$ group:

(ID)

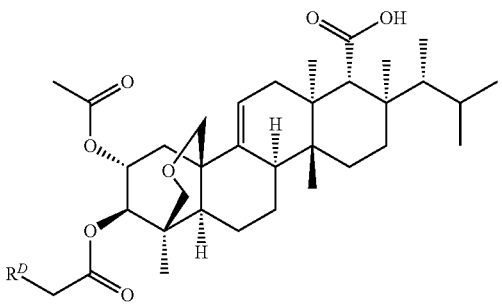

| Example # | Compound Name | $R^D$ | Mass | $^1$H NMR (400 MHz, MeOH-d4) δ |
|---|---|---|---|---|
| 89 | (1S,2R,3R,4aR,6aS,7R,8R, 10aR,10bR,12aR)-3-(acetyloxy)-2-(2-[bis-(2-hydroxy-ethyl)-amino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid | HOH$_2$CH$_2$C\N/HOH$_2$CH$_2$C | Calculated for $C_{38}H_{61}NO_9$: 675. Observed: 676 (M + H)$^+$. | 0.63 (s, 3 H) 0.67 (s, 3 H) 0.70 (d, J = 7.09 Hz, 3 H) 0.78 (d, J = 6.59 Hz, 3 H) 0.84 (d, J = 6.70 Hz, 3 H) 1.08 (s, 3 H) 1.13 (s, 3 H) 1.16-1.26 (m, 3 H) 1.27-1.60 (m, 5 H) 1.61-1.79 (m, 4 H) 1.83-1.89 (m, 1 H) 1.92 (s, 3 H) 1.94-2.21 (m, 6 H) 2.33-2.44 (m, 1 H) 2.78 (s, 1 H) 3.21-3.54 (m, 4 H) 3.57-3.67 (m, 1 H) 3.81-3.98 (m, 3 H) 4.04-4.18 (m, 2 H) 4.87 (d, J = 8.84 Hz, 1 H) 5.38 (s, 1 H) 5.72-5.85 (m, 1 H) |
| 90 | (1S,2R,3R,4aR,6aS,7R,8R, 10aR,10bR,12aR)-3-(acetyloxy)-2-(2-[4-(4-fluoro-2-methoxyphenyl)-piperidin-1-yl]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid | (4-fluoro-2-methoxyphenyl piperidine structure) | Calculated for $C_{45}H_{66}N_2O_8$: 762. Observed: 763 (M + H)$^+$. | 0.68 (s, 6 H) 0.71 (d, J = 7.14 Hz, 3 H) 0.79 (d, J = 6.59 Hz, 3 H) 0.84 (d, J = 6.76 Hz, 3 H) 1.09 (s, 3 H) 1.14 (s, 3 H) 1.16-1.26 (m, 3 H) 1.28-1.67 (m, 6 H) 1.68-1.79 (m, 3 H) 1.85-1.92 (m, 1 H) 1.94 (s, 3 H) 1.98-2.16 (m, 2 H) 2.32-2.45 (m, 1 H) 2.80 (s, 1 H) 3.42 (d, 12 H) 3.67 (d, J = 12.14 Hz, 2 H) 3.82 (s, 3 H) 4.92 (d, J = 8.95 Hz, 1 H) 5.40 (d, J = 5.11 Hz, 1 H) 5.74-5.88 (m, 1 H) 6.76-7.12 (m, 4 H) |
| 91 | (1S,2R,3R,4aR,6aS,7R,8R, 10aR,10bR,12aR)-3-(acetyloxy)-2-(2-(2-piperidin-1-ylethylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid | (piperidinyl-ethylamino structure) | Calculated for $C_{41}H_{66}N_2O_7$: 698. Observed: 699 (M + H)$^+$. | 0.73-0.76 (m, 3 H) 0.76-0.80 (m, 6 H) 0.87 (d, J = 6.70 Hz, 3 H) 0.91 (d, J = 6.76 Hz, 3 H) 1.19 (s, 3 H) 1.22 (s, 3 H) 1.24-1.36 (m, 3 H) 1.38-1.71 (m, 5 H) 1.72-1.90 (m, 3 H) 1.91-2.00 (m, 6 H) 2.02 (s, 3 H) 2.10-2.26 (m, 2 H) 2.43-2.53 (m, 1 H) 2.86 (s, 1 H) 3.41-3.78 (m, 14 H) 4.08-4.28 (m, 2 H) 5.03 (d, J = 9.17 Hz, 1 H) 5.51 (d, J = 5.60 Hz, 1 H) 5.83-5.92 (m, 1 H) |

(ID)

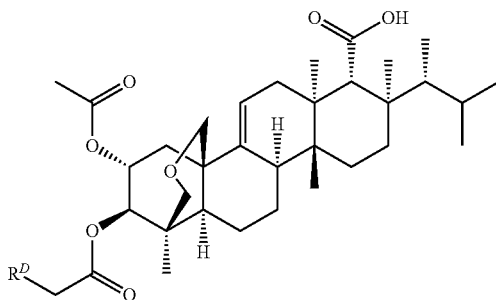

| Example # | Compound Name | $R^D$ | Mass | $^1$H NMR (400 MHz, MeOH-d4) δ |
|---|---|---|---|---|
| 92 | (1S,2R,3R,4aR,6aS,7R,8R,10aR,10bR,12aR)-3-(acetyloxy)-2-(2-(3-imidazol-1-ylpropylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | imidazol-N-CH2CH2CH2-NH- | Calculated for $C_{40}H_{61}N_3O_7$: 695. Observed: 696 (M + H)$^+$. | 0.59 (s, 3 H) 0.67 (s, 3 H) 0.70 (d, J = 7.14 Hz, 3 H) 0.78 (d, J = 6.54 Hz, 3 H) 0.84 (d, J = 6.59 Hz, 3 H) 1.08 (s, 3 H) 1.14 (s, 3 H) 1.16-1.25 (m, 3 H) 1.26-1.45 (m, 2 H) 1.46-1.60 (m, 3 H) 1.61-1.80 (m, 3 H) 1.89 (s, 3 H) 1.90-1.94 (m, 1 H) 1.95-2.02 (m, 2 H) 2.05-2.19 (m, 2 H) 2.29-2.51 (m, 4 H) 2.66-2.77 (m, 1 H) 2.78 (s, 1 H) 3.27-3.71 (m, 5 H) 4.03-4.26 (m, 2 H) 4.81-4.93 (m, 1 H) 5.35-5.45 (m, 1 H) 5.73-5.88 (m, 1 H) 7.00-7.07 (m, 1 H) 7.12 (s, 1 H) 8.03 (d, J = 8.57 Hz, 1 H) |
| 93 | (1S,2R,3R,4aR,6aS,7R,8R,10aR,10bR,12aR)-3-(acetyloxy)-2-(2-(cyclohexyl-methylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | cyclohexyl-N(Me)- | Calculated for $C_{41}H_{65}NO_7$: 683. Observed: 684 (M + H)$^+$. | 0.63 (s, 3 H) 0.68 (s, 3 H) 0.72 (d, J = 7.09 Hz, 3 H) 0.80 (d, J = 6.59 Hz, 3 H) 0.85 (d, J = 6.76 Hz, 3 H) 1.10 (s, 3 H) 1.11-1.14 (m, 1 H) 1.15 (s, 3 H) 1.16-1.26 (m, 5 H) 1.26-1.47 (m, 5 H) 1.48-1.84 (m, 9 H) 1.85-1.90 (m, 3 H) 1.91 (s, 3 H) 1.95-2.03 (m, 1 H) 2.06-2.16 (m, 1 H) 2.39 (dd, J = 13.40, 7.20 Hz, 1 H) 2.55 (s, 3 H) 2.80 (s, 1 H) 3.28-3.39 (m, 2 H) 3.44 (s, 1 H) 3.48 (d, J = 11.65 Hz, 1 H) 3.51-3.60 (m, 1 H) 3.64 (d, J = 12.09 Hz, 1 H) 4.89 (d, J = 9.06 Hz, 1 H) 5.40 (d, J = 5.60 Hz, 1 H) 5.73-5.86 (m, 1 H) |

-continued

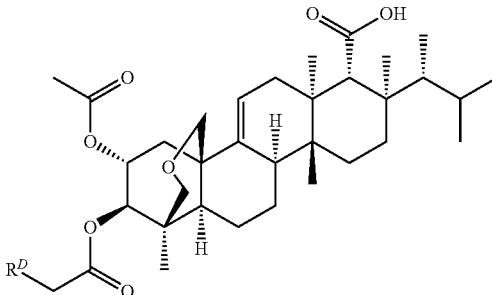

(ID)

| Example # | Compound Name | $R^D$ | Mass | $^1$H NMR (400 MHz, MeOH-d4) δ |
|---|---|---|---|---|
| 94 | (1S,2R,3R,4aR,6aS,7R,8R,10aR,10bR,12aR)-3-(acetyloxy)-2-(2-pyrrolidin-1-yl-acetoxy)-8-[(1R)-1,2-dimethylpropyl]-1,6a,8,10a tetramethyl1,3,4,6,6a,7,8,9,10,10a,10b,11,12,12a-tetradecahydro-2H-1,4a-(methanooxymethano) chrysene-7-carboxylic acid | pyrrolidine | Calculated for $C_{38}H_{59}NO_7$: 641. Observed: 642 (M + H)$^+$. | 0.65 (s, 6 H) 0.68 (d, J = 7.14 Hz, 3 H) 0.76 (d, J = 6.65 Hz, 3 H) 0.82 (d, J = 6.76 Hz, 3 H) 1.06 (s, 3 H) 1.11 (s, 3 H) 1.13-1.22 (m, 3 H) 1.24-1.64 (m, 6 H) 1.65-1.75 (m, 3 H) 1.82-1.90 (m, 1 H) 1.92 (s, 3 H) 1.93-2.00 (m, 1 H) 2.02-2.18 (m, 4 H) 2.27-2.37 (m, 1 H) 2.68-2.84 (m, 5 H) 2.89-3.07 (m, 2 H) 3.26-3.38 (m, 2 H) 3.40-3.48 (m, 1 H) 3.59-3.71 (m, 1 H) 3.76-4.14 (m, 3 H) 4.86 (d, J = 8.52 Hz, 1 H) 5.37 (d, J = 5.11 Hz, 1 H) 5.69-5.85 (m, 1 H) |
| 95 | (1S,2R,3R,4aR,6aS,7R,8R,10aR,10bR,12aR)-3-(acetyloxy)-2-(2-(3-hydroxy-pyrrolidin-1-yl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid | 3-hydroxypyrrolidine | Calculated for $C_{38}H_{59}NO_8$: 657. Observed: 658 (M + H)$^+$. | 0.64 (d, J = 2.97 Hz, 3 H) 0.66 (s, 3 H) 0.69 (d, J = 7.14 Hz, 3 H) 0.77 (d, J = 6.59 Hz, 3 H) 0.83 (d, J = 6.76 Hz, 3 H) 1.07 (s, 3 H) 1.13 (s, 3 H) 1.14-1.23 (m, 3 H) 1.25-1.58 (m, 6 H) 1.59-1.78 (m, 4 H) 1.83-1.91 (m, 2 H) 1.93 (s, 3 H) 1.94-2.01 (m, 2 H) 2.05-2.24 (m, 2 H) 2.31-2.40 (m, 1 H) 2.77 (s, 1 H) 2.79-2.91 (m, 2 H) 3.05-3.23 (m, 2 H) 3.33 (t, J = 11.45 Hz, 2 H) 3.42-3.49 (m, 1 H) 3.61-3.87 (m, 3 H) 4.39-4.48 (m, 1 H) 4.88 (d, J = 8.73 Hz, 1 H) 5.38 (d, J = 5.49 Hz, 1 H) 5.73-5.84 (m, 1 H) |
| 96 | (1S,2R,3R,4aR,6aS,7R,8R,10aR,10bR,12aR)-3-(acetyloxy)-2-(2-[4-(4-fluoro-phenyl)-piperazin-1-yl]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid | 4-(4-fluorophenyl)piperazine | Calculated for $C_{44}H_{63}FN_2O_7$: 750. Observed: 751 (M + H)$^+$. | 0.68 (s, 6 H) 0.71 (d, J = 7.14 Hz, 3 H) 0.79 (d, J = 6.43 Hz, 3 H) 0.84 (d, J = 6.59 Hz, 3 H) 1.10 (s, 3 H) 1.14 (s, 3 H) 1.17-1.27 (m, 3 H) 1.28-1.68 (m, 7 H) 1.68-1.81 (m, 3 H) 1.84-1.93 (m, 2 H) 1.95 (s, 3 H) 2.05-2.14 (m, 1 H) 2.31-2.44 (m, 1 H) 2.80 (s, 1 H) 4.85-4.96 (m, J = 7.58 Hz, 14 H) 5.39 (s, 1 H) 5.75-5.89 (m, 1 H) 6.91-7.09 (m, 4 H) |

-continued

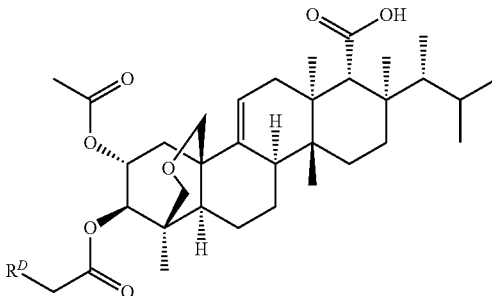

(ID)

| Example # | Compound Name | $R^D$ | Mass | $^1$H NMR (400 MHz, MeOH-d4) δ |
|---|---|---|---|---|
| 97 | (1S,2R,3R,4aR,6aS,7R,8R,10aR,10bR,12aR)-3-(acetyloxy)-2-(2-(4-methyl-piperazin-1-yl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | Me—N⌒N | Calculated for $C_{39}H_{62}N_2O_7$: 670. Observed: 671 (M + H)$^+$. | 0.60 (s, 3 H) 0.68 (s, 3 H) 0.72 (d, J = 7.14 Hz, 3 H) 0.79 (d, J = 6.59 Hz, 3 H) 0.85 (d, J = 6.81 Hz, 3 H) 1.09 (s, 3 H) 1.15 (s, 3 H) 1.17-1.26 (m, 3 H) 1.27-1.47 (m, 3 H) 1.47-1.68 (m, 3 H) 1.67-1.78 (m, 3 H) 1.88 (s, 3 H) 1.91-2.03 (m, 2 H) 2.08-2.18 (m, 1 H) 2.32-2.41 (m, 1 H) 2.43 (s, 3 H) 2.60-2.92 (m, 9 H) 3.22 (d, J = 2.20 Hz, 1 H) 3.33 (dd, J = 17.28, 12.44 Hz, 2 H) 3.49 (d, J = 11.54 Hz, 1 H) 3.62 (d, J = 11.98 Hz, 1 H) 4.87 (d, J = 9.06 Hz, 1 H) 5.43 (d, J = 5.27 Hz, 1 H) 5.72-5.84 (m, 1 H) |
| 98 | (1S,2R,3R,4aR,6aS,7R,8R,10aR,10bR,12aR)-3-(acetyloxy)-2-(2-morpholin-4-yl-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | O⌒N | Calculated for $C_{38}H_{58}NO_8$: 657. Observed: 658 (M + H)$^+$. | 0.69 (s, 6 H) 0.72 (d, J = 7.09 Hz, 3 H) 0.80 (d, J = 6.54 Hz, 3 H) 0.85 (d, J = 6.65 Hz, 3 H) 1.10 (s, 3 H) 1.14 (s, 3 H) 1.17-1.26 (m, 3 H) 1.29-1.68 (m, 7 H) 1.68-1.82 (m, 3 H) 1.86-1.90 (m, 1 H) 1.94 (s, 3 H) 1.96-2.05 (m, 1 H) 2.06-2.15 (m, 1 H) 2.29-2.43 (m, 1 H) 2.81 (s, 1 H) 3.27-3.52 (m, 8 H) 3.61-3.91 (m, 3 H) 3.96-4.19 (m, 3 H) 4.90 (d, J = 8.52 Hz, 1 H) 5.40 (s, 1 H) 5.74-5.87 (m, 1 H) |
| 99 | (1S,2R,3R,4aR,6aS,7R,8R,10aR,10bR,12aR)-3-(acetyloxy)-2-(2-dimethylamino-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | Me\N/Me | Calculated for $C_{36}H_{57}NO_7$: 615. Observed: 616 (M + H)$^+$. | 0.61-0.66 (m, 6 H) 0.67 (d, J = 7.14 Hz, 3 H) 0.76 (d, J = 6.65 Hz, 3 H) 0.81 (d, J = 6.70 Hz, 3 H) 1.06 (s, 3 H) 1.11 (s, 3 H) 1.13-1.23 (m, 3 H) 1.25-1.64 (m, 6 H) 1.65-1.75 (m, 3 H) 1.80-1.86 (m, 1 H) 1.90 (s, 3 H) 1.92-2.00 (m, 1 H) 2.03-2.12 (m, 1 H) 2.29-2.38 (m, 1 H) 2.75 (s, 1 H) 2.87-3.00 (m, 6 H) 3.26-3.38 (m, 2 H) 3.40-3.48 (m, 1 H) 3.61 (d, J = 11.87 Hz, 1 H) 3.81-4.09 (m, 2 H) 4.87 (d, J = 8.68 Hz, 1 H) 5.37 (d, J = 5.16 Hz, 1 H) 5.69-5.81 (m, 1 H) |

-continued (ID)

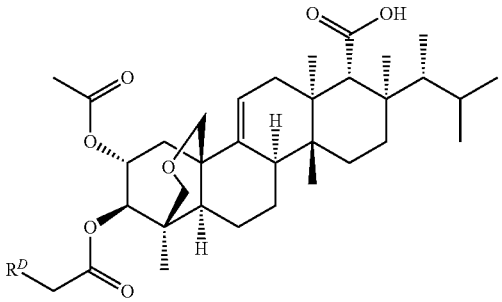

| Example # | Compound Name | $R^D$ | Mass | $^1$H NMR (400 MHz, MeOH-d4) δ |
|---|---|---|---|---|
| 100 | (1S,2R,3R,4aR,6aS,7R,8R, 10aR,10bR,12aR)-3-(acetyloxy)-2-(2-[(2,2-dimethoxyethyl)-methyl-amino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | MeO—⟨CH(OMe)—CH$_2$—N(Me)—⟩ | Calculated for $C_{39}H_{63}NO_9$: 689. Observed: 690 (M + H)$^+$. | 0.62 (s, 3 H) 0.68 (s, 3 H) 0.72 (d, J = 7.14 Hz, 3 H) 0.80 (d, J = 6.65 Hz, 3 H) 0.85 (d, J = 6.76 Hz, 3 H) 1.10 (s, 3 H) 1.15 (s, 3 H) 1.17-1.26 (m, 3 H) 1.28-1.47 (m, 3 H) 1.48-1.79 (m, 6 H) 1.84-1.89 (m, 1 H) 1.92 (s, 3 H) 1.95-2.05 (m, 2 H) 2.06-2.15 (m, 1 H) 2.36-2.45 (m, 1 H) 2.55 (s, 3 H) 2.81 (s, 1 H) 2.81-2.87 (m, 2 H) 3.34 (s, 7 H) 3.44-3.55 (m, 2 H) 3.64 (d, J = 11.98 Hz, 1 H) 4.51-4.65 (m, 1 H) 4.90 (d, J = 9.12 Hz, 1 H) 5.40 (d, J = 5.55 Hz, 1 H) 5.74-5.86 (m, 1 H) |
| 101 | (1S,2R,3R,4aR,6aS,7R,8R, 10aR,10bR,12aR)-3-(acetyloxy)-2-(2-(ethyl-methyl-amino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | Et—N(Me)— | Calculated for $C_{37}H_{59}NO_7$: 629. Observed: 630 (M + H)$^+$. | 0.62 (s, 3 H) 0.68 (s, 3 H) 0.72 (d, J = 7.14 Hz, 3 H) 0.80 (d, J = 6.70 Hz, 3 H) 0.85 (d, J = 6.76 Hz, 3 H) 1.10 (s, 3 H) 1.11-1.14 (m, 3 H) 1.15 (s, 3 H) 1.17-1.26 (m, 3 H) 1.28-1.46 (m, 3 H) 1.46-1.79 (m, 6 H) 1.85-1.89 (m, 1 H) 1.92 (s, 3 H) 1.95-2.05 (m, 1 H) 2.06-2.17 (m, 1 H) 2.36-2.43 (m, 1 H) 2.48 (s, 3 H) 2.76 (d, J = 7.14 Hz, 2 H) 2.80 (s, 1 H) 3.27-3.40 (m, 2 H) 3.40-3.45 (m, 2 H) 3.45-3.53 (m, 1 H) 3.64 (d, J = 11.98 Hz, 1 H) 4.90 (d, J = 9.12 Hz, 1 H) 5.40 (d, J = 5.66 Hz, 1 H) 5.74-5.86 (m, 1 H) |

-continued

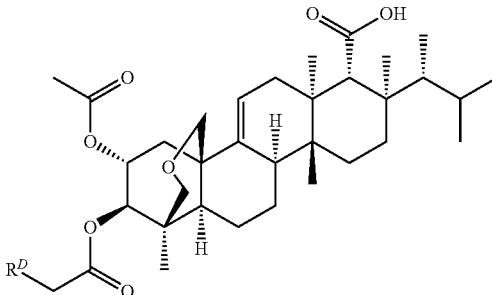

(ID)

| Example # | Compound Name | $R^D$ | Mass | $^1$H NMR (400 MHz, MeOH-d4) δ |
|---|---|---|---|---|
| 102 | (1S,2R,3R,4aR,6aS,7R,8R, 10aR,10bR,12aR)-3-(acetyloxy)-2-(2-[(2-diethylamino-ethyl)-methylamino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | Et$_2$N⁀⁀N(Me) | Calculated for $C_{42}H_{70}N_2O_7$: 714. Observed: 715 (M + H)$^+$. | 0.62 (s, 3 H) 0.68 (s, 3 H) 0.71 (d, J = 7.09 Hz, 3 H) 0.79 (d, J = 6.65 Hz, 3 H) 0.85 (d, J = 6.76 Hz, 3 H) 1.00 (t, J = 7.11 Hz, 3 H) 1.10 (s, 3 H) 1.15 (s, 3 H) 1.17-1.29 (m, J = 7.14, 7.14 Hz, 9 H) 1.29-1.46 (m, 3 H) 1.48-1.80 (m, 5 H) 1.85-1.89 (m, 1 H) 1.91 (s, 3 H) 1.95-2.03 (m, 1 H) 2.07-2.18 (m, 1 H) 2.32-2.43 (m, 1 H) 2.53-2.68 (m, 3 H) 2.79 (s, 1 H) 2.89-3.09 (m, 8 H) 3.28-3.40 (m, 4 H) 3.44-3.51 (m, 1 H) 3.63 (d, J = 12.03 Hz, 1 H) 4.87 (d, J = 9.06 Hz, 1 H) 5.39 (d, J = 5.55 Hz, 1 H) 5.74-5.85 (m, 1 H) |
| 103 | (1S,2R,3R,4aR,6aS,7R,8R, 10aR,10bR,12aR)-3-(acetyloxy)-2-(2-(4-ethyl-piperazin-1-yl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | Et—N(piperazine)N— | Calculated for $C_{40}H_{64}N_2O_7$: 684. Observed: 685 (M + H)$^+$. | 0.59 (s, 3 H) 0.68 (s, 3 H) 0.71 (d, J = 7.14 Hz, 3 H) 0.79 (d, J = 6.65 Hz, 3 H) 0.85 (d, J = 6.70 Hz, 3 H) 1.09 (s, 3 H) 1.15 (s, 3 H) 1.16-1.27 (m, 6 H) 1.28-1.46 (m, 3 H) 1.45-1.80 (m, 6 H) 1.87 (s, 3 H) 1.91-2.03 (m, 2 H) 2.08-2.20 (m, 1 H) 2.31-2.42 (m, 1 H) 2.53-3.00 (m, 11 H) 3.13-3.28 (m, 2 H) 3.33 (dd, J = 17.72, 12.06 Hz, 2 H) 3.49 (d, J = 11.59 Hz, 1 H) 3.62 (d, J = 11.98 Hz, 1 H) 4.86 (d, J = 9.01 Hz, 1 H) 5.44 (d, J = 5.49 Hz, 1 H) 5.72-5.84 (m, 1 H) |

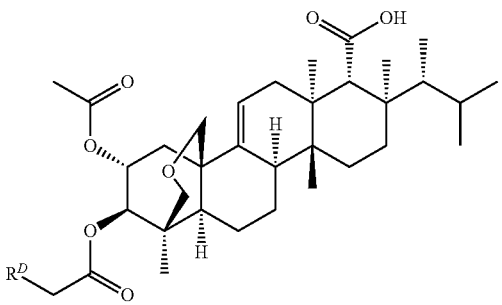

(ID)

| Example # | Compound Name | $R^D$ | Mass | $^1$H NMR (400 MHz, MeOH-d4) δ |
|---|---|---|---|---|
| 104 | (1S,2R,3R,4aR,6aS,7R,8R,10aR,10bR,12aR)-3-(acetyloxy)-2-(2-(2-pyrrolidin-1-yl-ethylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | pyrrolidine-CH2CH2-NH | Calculated for $C_{40}H_{64}N_2O_7$: 684. Observed: 685 $(M + H)^+$. | 0.64 (s, 3 H) 0.71 (s, 3 H) 0.75 (d, J = 7.14 Hz, 3 H) 0.75 (d, J = 7.14 Hz, 3 H) 0.83 (d, J = 6.65 Hz, 3 H) 0.88 (d, J = 6.77 Hz, 3 H) 1.13 (s, 3 H) 1.19 (s, 3 H) 1.20-1.29 (m, 3 H) 1.30-1.48 (m, 3 H) 1.50-1.70 (m, 3 H) 1.71-1.81 (m, 3 H) 1.82-1.92 (m, 2 H) 1.94 (s, 3 H) 1.99-2.06 (m, 1 H) 2.13-2.20 (m, 1 H) 2.37 (s, 1 H) 2.38-2.45 (m, 1 H) 2.70-3.08 (m, 9 H) 3.28-3.45 (m, 4 H) 3.48-3.55 (m, 1 H) 3.67 (t, J = 12.18 Hz, 1 H) 4.90 (d, J = 9.09 Hz, 1 H) 5.44 (s, 1 H) 5.76-5.88 (m, 1 H) |
| 105 | (1S,2R,3R,4aR,6aS,7R,8R,10aR,10bR,12aR)-3-(acetyloxy)-2-(2-[3-(2-oxo-pyrrolidin-1-yl)-propylamino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | 2-oxo-pyrrolidine-CH2CH2CH2-NH | Calculated for $C_{41}H_{64}N_2O_8$: 712. Observed: 713 $(M + H)^+$. | 0.64-0.69 (m, 3 H) 0.72 (s, 3 H) 0.75 (d, J = 7.14 Hz, 3 H) 0.83 (d, J = 6.65 Hz, 3 H) 0.88 (d, J = 6.77 Hz, 3 H) 1.13 (s, 3 H) 1.18 (s, 3 H) 1.20-1.30 (m, 4 H) 1.30-1.49 (m, 3 H) 1.48-1.73 (m, 4 H) 1.72-1.82 (m, 2 H) 1.82-1.93 (m, 3 H) 1.93-1.97 (m, 1 H) 1.98 (s, 3 H) 2.00-2.09 (m, 1 H) 2.09-2.22 (m, 1 H) 2.35-2.48 (m, 3 H) 2.68-2.78 (m, 2 H) 2.85 (s, 1 H) 3.29-3.45 (m, 6 H) 3.47-3.58 (m, 3 H) 3.67-3.76 (m, 1 H) 4.76-4.92 (m, 2 H) 4.94 (d, J = 9.16 Hz, 1 H) 5.43 (d, J = 5.74 Hz, 1 H) 5.78-5.91 (m, 1 H) |

-continued

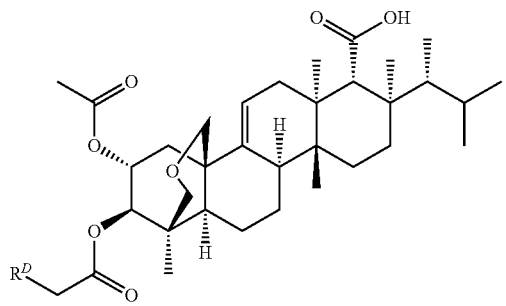

(ID)

| Example # | Compound Name | $R^D$ | Mass | $^1$H NMR (400 MHz, MeOH-d4) δ |
|---|---|---|---|---|
| 106 | (1S,2R,3R,4aR,6aS,7R,8R,10aR,10bR,12aR)-3-(acetyloxy)-2-(2-(2-morpholin-4-yl-ethylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | morpholine-CH2CH2-NH | Calculated for $C_{40}H_{64}N_2O_8$: 700. Observed: 701 (M + H)$^+$. | 0.65 (s, 3 H) 0.71 (s, 3 H) 0.75 (d, J = 7.02 Hz, 3 H) 0.83 (d, J = 6.47 Hz, 3 H) 0.88 (d, J = 6.59 Hz, 3 H) 1.12 (s, 3 H) 1.18 (s, 3 H) 1.20-1.29 (m, 3 H) 1.30-1.49 (m, 3 H) 1.51-1.71 (m, 4 H) 1.72-1.84 (m, 3 H) 1.87-1.93 (m, 1 H) 1.95 (s, 3 H) 1.98-2.06 (m, 1 H) 2.08-2.18 (m, 1 H) 2.37-2.61 (m, 7 H) 2.63-2.74 (m, 2 H) 2.82 (s, 1 H) 3.27-3.43 (m, 2 H) 3.44 (s, 2 H) 3.51 (d, J = 11.54 Hz, 1 H) 3.67 (d, J = 12.02 Hz, 1 H) 3.69-3.77 (m, 4 H) 4.93 (d, J = 9.09 Hz, 1 H) 5.43 (d, J = 4.09 Hz, 1 H) 5.76-5.90 (m, 1 H) |
| 107 | (1S,2R,3R,4aR,6aS,7R,8R,10aR,10bR,12aR)-3-(acetyloxy)-2-(2-(1-ethoxycarbonyl piperidin-4-yl)-amino-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | EtO-C(O)-N-piperidine-NH | Calculated for $C_{42}H_{66}N_2O_9$: 742. Observed: 743 (M + H)$^+$. | 0.65 (s, 3 H) 0.72 (s, 2 H) 0.75 (d, J = 7.14 Hz, 3 H) 0.83 (d, J = 6.65 Hz, 3 H) 0.88 (d, J = 6.77 Hz, 3 H) 1.13 (s, 3 H) 1.18 (s, 3 H) 1.19-1.28 (m, 3 H) 1.24 (t, J = 7.11 Hz, 3 H) 1.28-1.49 (m, 5 H) 1.51-1.72 (m, 4 H) 1.71-1.84 (m, 5 H) 1.88-1.92 (m, 1 H) 1.95 (s, 3 H) 1.98-2.02 (m, 1 H) 2.10-2.18 (m, 1 H) 2.43 (dd, J = 13.43, 7.20 Hz, 1 H) 2.56-2.65 (m, 1 H) 2.84 (s, 3 H) 3.35 (d, J = 11.41 Hz, 1 H) 3.39 (d, J = 10.32 Hz, 1 H) 3.45 (d, J = 1.95 Hz, 2 H) 3.51 (d, J = 11.60 Hz, 1 H) 3.66 (d, J = 12.02 Hz, 1 H) 3.99-4.08 (m, 2 H) 4.10 (q, J = 7.10 Hz, 2 H) 4.93 (d, J = 9.16 Hz, 1 H) 5.43 (d, J = 5.68 Hz, 1 H) 5.80-5.90 (m, 1 H) |

(ID)

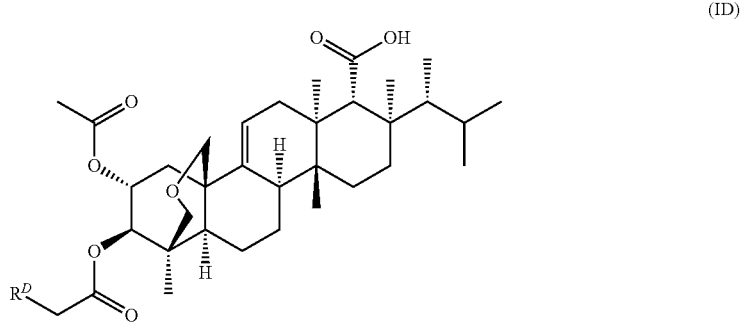

| Example # | Compound Name | $R^D$ | Mass | $^1$H NMR (400 MHz, MeOH-d4) δ |
|---|---|---|---|---|
| 108 | (1S,2R,3R,4aR,6aS,7R,8R, 10aR,10bR,12aR)-3-(acetyloxy)-2-(2-(2-methoxy-1-methyl-ethylamino)-acetoxy)-8-[(1R)-1,2-dimethylpropyl]-1,6a,8,10a-tetramethyl-1,3,4,6,6a,7,8,9,10,10a, 10b,11,12,12a-tetradecahydro-2H-1,4a-(methanooxymethano) chrysene-7-carboxylic acid | MeO⏜⏜NH (Me) | Calculated for $C_{38}H_{61}NO_8$: 659. Observed: 660 (M + H)$^+$. | 0.65 (d, J = 3.54 Hz, 3 H) 0.72 (s, 3 H) 0.75 (d, J = 7.14 Hz, 3 H) 0.83 (d, J = 6.65 Hz, 3 H) 0.88 (d, J = 6.77 Hz, 3 H) 1.00 (t, J = 6.68 Hz, 3 H) 1.13 (s, 3 H) 1.19 (s, 3 H) 1.21-1.29 (m, 3 H) 1.32-1.48 (m, 3 H) 1.50-1.71 (m, 3 H) 1.72-1.81 (m, 3 H) 1.88-1.93 (m, 1 H) 1.95 (s, 3 H) 1.99-2.06 (m, 1 H) 2.09-2.18 (m, 1 H) 2.40-2.49 (m, 1 H) 2.84 (s, 1 H) 2.86-2.92 (m, 1 H) 3.20-3.32 (m, 2 H) 3.33 (d, J = 3.23 Hz, 3 H) 3.35-3.47 (m, 3 H) 3.47-3.57 (m, 2 H) 3.68 (dd, J = 11.93, 6.56 Hz, 1 H) 4.94 (d, J = 9.22 Hz, 1 H) 5.43 (d, J = 5.62 Hz, 1 H) 5.79-5.89 (m, 1 H) |
| 109 | (1S,2R,3R,4aR,6aS,7R,8R, 10aR,10bR,12aR)-3-(acetyloxy)-2-(2-methylamino-acetoxy)-8-[(1R)-1,2-dimethylpropyl]-1,6a,8,10a-tetramethyl-1,3,4,6,6a,7,8,9,10,10a, 10b,11,12,12a-tetradecahydro-2H-1,4a-(methanooxymethano) chrysene-7-carboxylic acid | Me⏜N(H) | Calculated for $C_{35}H_{55}NO_7$: 601. Observed: 602 (M + H)$^+$. | 0.65 (s, 3 H) 0.72 (s, 3 H) 0.75 (d, J = 7.14 Hz, 3 H) 0.83 (d, J = 6.71 Hz, 3 H) 0.89 (d, J = 6.77 Hz, 3 H) 1.13 (s, 3 H) 1.19 (s, 3 H) 1.21-1.31 (m, 4 H) 1.32-1.51 (m, 3 H) 1.52-1.71 (m, 3 H) 1.73-1.83 (m, 3 H) 1.89-1.93 (m, 1 H) 1.96 (s, 3 H) 2.10-2.19 (m, 1 H) 2.41 (s, 3 H) 2.42-2.48 (m, 1 H) 2.86 (s, 1 H) 3.32-3.44 (m, J = 11.35 Hz, 4 H) 3.52 (d, J = 11.66 Hz, 1 H) 3.68 (d, J = 11.96 Hz, 1 H) 4.94 (d, J = 9.09 Hz, 1 H) 5.44 (d, J = 5.86 Hz, 1 H) 5.79-5.89 (m, 1 H) |

(ID)

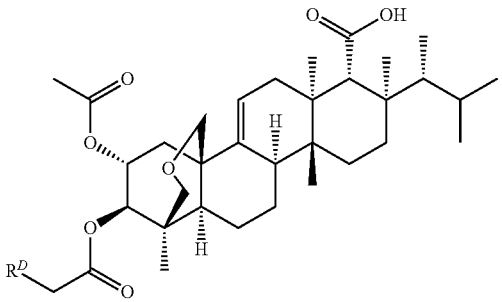

| Example # | Compound Name | $R^D$ | Mass | $^1$H NMR (400 MHz, MeOH-d4) δ |
|---|---|---|---|---|
| 110 | (1S,2R,3R,4aR,6aS,7R,8R,10aR,10bR,12aR)-3-(acetyloxy)-2-(2-(2-dimethylamino-ethylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | Me$_2$N—NH | Calculated for $C_{38}H_{62}N_2O_7$: 658. Observed: 659 (M + H)$^+$. | 0.65 (s, 3 H) 0.72 (s, 3 H) 0.75 (d, J = 7.14 Hz, 3 H) 0.83 (d, J = 6.65 Hz, 3 H) 0.89 (d, J = 6.71 Hz, 3 H) 1.13 (s, 3 H) 1.19 (s, 3 H) 1.21-1.32 (m, 3 H) 1.33-1.50 (m, 3 H) 1.50-1.71 (m, 4 H) 1.72-1.81 (m, 3 H) 1.89-1.93 (m, 1 H) 1.94 (s, 3 H) 1.98-2.03 (m, 1 H) 2.12-2.19 (m, 1 H) 2.25-2.35 (m, 6 H) 2.39-2.57 (m, 2 H) 2.66-2.74 (m, 1 H) 2.83 (s, 1 H) 3.30-3.45 (m, 4 H) 3.51 (d, J = 11.66 Hz, 1 H) 3.67 (d, J = 11.72 Hz, 1 H) 4.88-4.95 (m, 1 H) 5.44 (d, J = 5.68 Hz, 1 H) 5.79-5.88 (m, 1 H) |
| 111 | (1S,2R,3R,4aR,6aS,7R,8R,10aR,10bR,12aR)-3-(acetyloxy)-2-(2-(3-isopropoxy-propylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | Me₂CH—O—NH | Calculated for $C_{40}H_{65}NO_8$: 687. Observed: 688 (M + H)$^+$. | 0.65 (s, 3 H) 0.72 (s, 3 H) 0.75 (d, J = 7.20 Hz, 3 H) 0.83 (d, J = 6.71 Hz, 3 H) 0.89 (d, J = 6.84 Hz, 3 H) 1.13 (d, J = 5.98 Hz, 9 H) 1.19 (s, 3 H) 1.21-1.30 (m, 3 H) 1.32-1.51 (m, 3 H) 1.51-1.65 (m, 3 H) 1.66-1.81 (m, 5 H) 1.88-1.93 (m, 1 H) 1.95 (s, 3 H) 2.00-2.05 (m, 1 H) 2.10-2.18 (m, 1 H) 2.45 (dd, J = 13.43, 7.26 Hz, 1 H) 2.64-2.73 (m, 2 H) 2.86 (s, 1 H) 3.26-3.58 (m, 8 H) 3.67 (d, J = 11.96 Hz, 1 H) 4.94 (d, J = 8.79 Hz, 1 H) 5.43 (d, J = 5.80 Hz, 1 H) 5.80-5.89 (m, 1 H) |
| 112 | (1S,2R,3R,4aR,6aS,7R,8R,10aR,10bR,12aR)-3-(acetyloxy)-2-(2-(1,2,2,6,6-pentamethyl-piperidin-4-ylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | Me—N(piperidine with Me,Me,Me,Me)—NH | Calculated for $C_{44}H_{72}N_2O_7$: 740. Observed: 741 (M + H)$^+$. | 0.67 (s, 3 H) 0.74 (s, 3 H) 0.77 (d, 3 H) 0.84 (d, 3 H) 0.91 (d, 3 H) 1.14 (s, 3 H) 1.20 (s, 3 H) 1.23-1.40 (m, 6 H) 1.40-1.51 (m, 6 H) 1.51-1.66 (m, 4 H) 1.66-1.74 (m, 4 H) 1.66-1.87 (m, 4 H) 1.90-1.96 (m, 2 H) 2.00-2.11 (m, 2 H) 2.12-2.23 (m, 1 H) 2.30-2.56 (m, 3 H) 2.82-2.86 (m, 1 H) 2.86-2.95 (m, 1 H) 3.32-3.44 (m, 2 H) 3.47 (d, 1 H) 3.53 (d, 1 H) 3.69 (d, 1 H) 4.94 (d, 1 H) 5.44 (m, 1 H) |

-continued

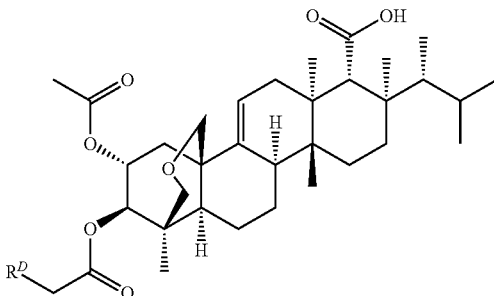

(ID)

| Example # | Compound Name | $R^D$ | Mass | $^1$H NMR (400 MHz, MeOH-d4) δ |
|---|---|---|---|---|
| 113 | (1S,2R,3R,4aR,6aS,7R,8R,10aR,10bR,12aR)-3-(acetyloxy)-2-(2-[(piperidin-4-ylmethyl)-amino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | piperidin-4-ylmethyl-amino | Calculated for $C_{40}H_{64}N_2O_7$: 684. Observed: 685 (M + H)$^+$. | 0.66 (s, 3 H) 0.74 (s, 3 H) 0.78 (d, 3 H) 0.84 (d, 3 H) 0.92 (d, 3 H) 1.15 (s, 3 H) 1.21 (s, 3 H) 1.23-1.30 (m, 5 H) 1.30-1.52 (m, 2 H) 1.52-1.85 (m, 6 H) 1.97 (s, 3 H) 2.02-2.07 (m, 2 H) 2.08 (s, 3 H) 2.11-2.25 (m, 2 H) 2.24-2.60 (m, 8 H) 2.60-2.73 (m, 1 H) 2.80-3.01 (m, 2 H) 3.21-3.30 (s, 1 H) 3.31-3.45 (m, 2 H) 3.55 (d, 1 H) 3.69 (d, 1 H) 4.95 (d, 1 H) 5.46 (s, 1 H) 5.72-6.01 (m, 1 H) |
| 114 | (1S,2R,3R,4aR,6aS,7R,8R,10aR,10bR,12aR)-3-(acetyloxy)-2-(2-[3-(2-methyl-piperidin-1-yl)-propylamino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | 2-methyl-piperidin-1-yl-propylamino | Calculated for $C_{43}H_{70}N_2O_7$: 726. Observed: 727 (M + H)$^+$. | 0.63 (s, 3 H) 0.71 (s, 3 H) 0.74 (d, J = 7.20 Hz, 3 H) 0.82 (d, J = 6.65 Hz, 3 H) 0.87 (d, J = 6.77 Hz, 3 H) 1.13 (s, 3 H) 1.19 (s, 3 H) 1.21-1.29 (m, 5 H) 1.30-1.48 (m, 5 H) 1.50-1.64 (m, 3 H) 1.64-1.87 (m, 9 H) 1.92 (s, 3 H) 1.93 (s, 3 H) 1.94-1.97 (m, 2 H) 1.99 (s, 3 H) 2.01-2.07 (m, 2 H) 2.10-2.23 (m, 1 H) 2.38-2.48 (m, 1 H) 2.53-2.68 (m, 3 H) 2.75-2.83 (m, 2 H) 2.84-2.92 (m, 1 H) 2.93-3.01 (m, 1 H) 3.02-3.12 (m, 1 H) 3.35 (d, J = 11.84 Hz, 2 H) 3.37-3.42 (m, 3 H) 3.50 (d, J = 11.66 Hz, 1 H) 3.66 (d, J = 12.09 Hz, 1 H) 4.91 (d, J = 8.91 Hz, 1 H) 5.43 (s, 1 H) 5.78-5.89 (m, 1 H) |

-continued

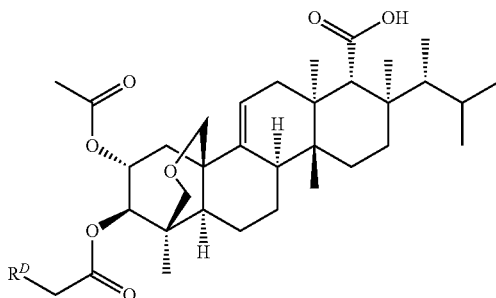

(ID)

| Example # | Compound Name | $R^D$ | Mass | $^1$H NMR (400 MHz, MeOH-d4) δ |
|---|---|---|---|---|
| 115 | (1S,2R,3R,4aR,6aS,7R,8R,10aR,10bR,12aR)-3-(acetyloxy)-2-(2-(3-methylamino-propylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | MeHN~~~NH | Calculated for $C_{38}H_{62}N_2O_7$: 658. Observed: 659 (M + H)$^+$. | 0.64 (s, 3 H) 0.72 (s, 3 H) 0.75 (d, J = 7.14 Hz, 3 H) 0.83 (d, J = 6.65 Hz, 3 H) 0.88 (d, J = 6.77 Hz, 3 H) 1.13 (s, 3 H) 1.18 (s, 3 H) 1.24 (d, J = 7.45 Hz, 3 H) 1.31-1.40 (m, 2 H) 1.39-1.49 (m, 2 H) 1.51-1.65 (m, 2 H) 1.65-1.71 (m, 1 H) 1.71-1.83 (m, 4 H) 1.83-1.90 (m, 1 H) 1.90-1.94 (m, 1 H) 1.95 (s, 1 H) 1.96 (s, 3 H) 1.99-2.03 (m, 1 H) 2.09-2.24 (m, 2 H) 2.34 (s, 1 H) 2.43 (s, 1 H) 2.54-2.59 (m, 1 H) 2.67 (s, 1 H) 2.73-2.80 (m, 1 H) 2.84 (s, 1 H) 3.25 (d, J = 9.03 Hz, 1 H) 3.33-3.47 (m, 3 H) 3.51 (d, J = 11.47 Hz, 1 H) 3.66 (d, J = 11.72 Hz, 1 H) 4.91 (d, J = 8.85 Hz, 1 H) 5.43 (s, 1 H) 5.77-5.92 (m, 1 H) |
| 116 | (1S,2R,3R,4aR,6aS,7R,8R,10aR,10bR,12aR)-3-(acetyloxy)-2-(2-(3-dimethylamino-propylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | Me$_2$N~~~NH | Calculated for $C_{39}H_{64}N_2O_7$: 672. Observed: 673 (M + H)$^+$. | 0.64 (s, 3 H) 0.71 (s, 3 H) 0.74 (d, J = 7.14 Hz, 3 H) 0.82 (d, J = 6.65 Hz, 3 H) 0.87 (d, J = 6.77 Hz, 3 H) 1.13 (s, 3 H) 1.18 (s, 3 H) 1.20-1.29 (m, 3 H) 1.31-1.38 (m, 1 H) 1.38-1.48 (m, 2 H) 1.50-1.63 (m, 2 H) 1.64-1.71 (m, 1 H) 1.71-1.84 (m, 5 H) 1.93 (s, 3 H) 1.95 (d, J = 6.71 Hz, 1 H) 2.00 (s, 3 H) 2.04-2.08 (m, 1 H) 2.10-2.22 (m, 1 H) 2.34 (s, 1 H) 2.43 (s, 6 H) 2.59-2.75 (m, 2 H) 2.80 (s, 1 H) 3.27-3.45 (m, 4 H) 3.51 (d, J = 11.66 Hz, 1 H) 3.66 (d, J = 12.09 Hz, 1 H) 4.91 (d, J = 9.28 Hz, 1 H) 5.43 (s, 1 H) 5.78-5.90 (m, 1 H) |

-continued

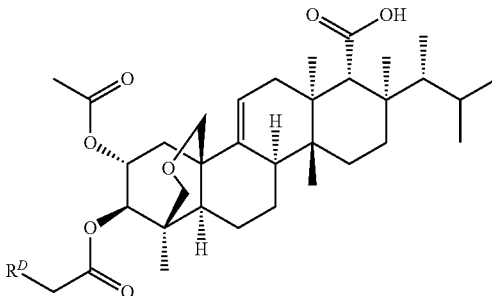

(ID)

| Example # | Compound Name | $R^D$ | Mass | $^1$H NMR (400 MHz, MeOH-d4) δ |
|---|---|---|---|---|
| 117 | (1S,2R,3R,4aR,6aS,7R,8R,10aR,10bR,12aR)-3-(acetyloxy)-2-(2-(3-pyrrolidin-1-yl-propylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | | Calculated for $C_{41}H_{66}N_2O_7$: 698. Observed: 699 (M + H)$^+$. | 0.63 (s, 3 H) 0.71 (s, 3 H) 0.74 (d, J = 7.14 Hz, 3 H) 0.82 (d, J = 6.65 Hz, 3 H) 0.87 (d, J = 6.77 Hz, 3 H) 1.12 (s, 3 H) 1.18 (s, 3 H) 1.19-1.29 (m, 3 H) 1.30-1.37 (m, 1 H) 1.38-1.48 (m, 2 H) 1.48-1.63 (m, 3 H) 1.63-1.85 (m, 6 H) 1.85-1.92 (m, 2 H) 1.92 (s, 3 H) 1.93-1.98 (m, 4 H) 1.99 (s, 3 H) 2.01-2.07 (m, 2 H) 2.11-2.22 (m, 1 H) 2.37-2.48 (m, 1 H) 2.56-2.72 (m, 2 H) 2.79 (s, 1 H) 2.97 (t, 1 H) 3.03-3.11 (m, 2 H) 3.30-3.42 (m, 4 H) 3.50 (d, J = 11.60 Hz, 1 H) 3.65 (d, J = 12.09 Hz, 1 H) 4.90 (d, J = 9.09 Hz, 1 H) 5.35-5.49 (m, 1 H) 5.78-5.87 (m, 1 H) |
| 118 | (1S,2R,3R,4aR,6aS,7R,8R,10aR,10bR,12aR)-3-(acetyloxy)-2-(2-[(3-dimethylaminopropyl)-methyl-amino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | | Calculated for $C_{40}H_{66}N_2O_7$: 686. Observed: 687 (M + H)$^+$. | 0.64 (s, 3 H) 0.71 (s, 3 H) 0.74 (d, J = 7.08 Hz, 3 H) 0.82 (d, J = 6.59 Hz, 3 H) 0.87 (d, J = 6.77 Hz, 3 H) 1.13 (s, 3 H) 1.18 (s, 3 H) 1.20-1.29 (m, 3 H) 1.30-1.37 (m, 1 H) 1.44 (t, 2 H) 1.49-1.63 (m, 2 H) 1.63-1.70 (m, 1 H) 1.71-1.84 (m, 6 H) 1.93 (s, 3 H) 1.94-1.96 (m, 1 H) 1.99 (s, 3 H) 2.01-2.04 (m, 1 H) 2.04-2.06 (m, 1 H) 2.12-2.22 (m, 1 H) 2.32 (s, 3 H) 2.39-2.45 (m, 1 H) 2.47 (s, 6 H) 2.51 (t, 2 H) 2.66-2.75 (m, 2 H) 2.79 (s, 1 H) 3.24 (s, 2 H) 3.35 (d, J = 11.96 Hz, 1 H) 3.38 (d, J = 12.02 Hz, 1 H) 3.50 (d, J = 11.60 Hz, 1 H) 3.65 (d, J = 12.09 Hz, 1 H) 4.90 (d, J = 9.09 Hz, 1 H) 5.43 (s, 1 H) 5.76-5.89 (m, 1 H) |

-continued

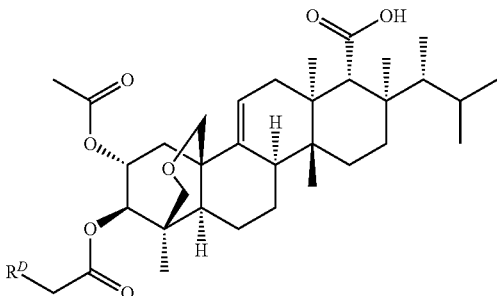

(ID)

| Example # | Compound Name | $R^D$ | Mass | $^1$H NMR (400 MHz, MeOH-d4) δ |
|---|---|---|---|---|
| 119 | (1S,2R,3R,4aR,6aS,7R,8R,10aR,10bR,12aR)-3-(acetyloxy)-2-(2-[bis-(3-dimethylaminopropyl)-amino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | 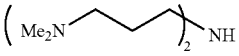 | Calculated for $C_{44}H_{75}N_3O_7$: 757. Observed: 758 $(M + H)^+$. | 0.64 (s, 3 H) 0.71 (s, 3 H) 0.75 (d, J = 7.14 Hz, 3 H) 0.82 (d, J = 6.65 Hz, 3 H) 0.87 (d, J = 6.71 Hz, 3 H) 1.12 (s, 3 H) 1.19 (s, 3 H) 1.21-1.30 (m, 3 H) 1.30-1.38 (m, 1 H) 1.38-1.47 (m, 2 H) 1.50-1.62 (m, 2 H) 1.63-1.70 (m, 1 H) 1.71-1.84 (m, 6 H) 1.89 (s, 3 H) 1.91-2.09 (m, 4 H) 2.14-2.25 (m, 1 H) 2.32-2.46 (m, 2 H) 2.49 (s, 12 H) 2.55-2.64 (m, 4 H) 2.67-2.84 (m, 4 H) 3.30-3.43 (m, 4 H) 3.51 (d, J = 11.66 Hz, 1 H) 3.64 (d, J = 11.84 Hz, 1 H) 4.87 (d, J = 9.16 Hz, 1 H) 5.45-5.53 (m, 1 H) 5.77-5.91 (m, 1 H) |
| 120 | (1S,2R,3R,4aR,6aS,7R,8R,10aR,10bR,12aR)-3-(acetyloxy)-2-(2-(4-pyrrolidin-1-yl-piperidin-1-yl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | 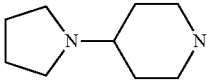 | Calculated for $C_{43}H_{68}N_2O_7$: 724. Observed: 725 $(M + H)^+$. | 0.62 (s, 3 H) 0.70 (s, 3 H) 0.73 (d, J = 7.20 Hz, 3 H) 0.81 (d, J = 6.65 Hz, 3 H) 0.86 (d, J = 6.77 Hz, 3 H) 1.12 (s, 3 H) 1.18 (s, 3 H) 1.21-1.29 (m, 3 H) 1.29-1.37 (m, 1 H) 1.37-1.47 (m, 2 H) 1.49-1.59 (m, 2 H) 1.62-1.82 (m, 7 H) 1.86-1.94 (m, 9 H) 1.95-2.05 (m, 4 H) 2.14-2.23 (m, 1 H) 2.24-2.34 (m, 2 H) 2.35-2.45 (m, 1 H) 2.71-2.81 (m, 2 H) 2.87-3.09 (m, 6 H) 3.23 (q, 2 H) 3.33 (d, J = 11.96 Hz, 1 H) 3.38 (d, J = 12.76 Hz, 1 H) 3.50 (d, J = 11.60 Hz, 1 H) 3.64 (d, J = 11.96 Hz, 1 H) 4.89 (d, J = 9.16 Hz, 1 H) 5.42 (s, 1 H) 5.77-5.88 (m, 1 H) |

-continued

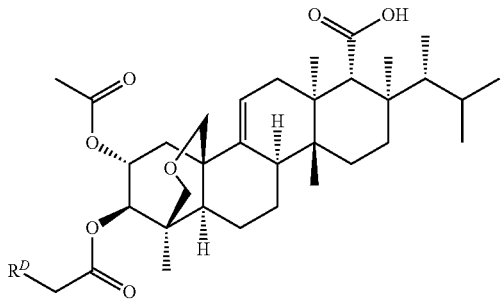

(ID)

| Example # | Compound Name | $R^D$ | Mass | $^1$H NMR (400 MHz, MeOH-d4) δ |
|---|---|---|---|---|
| 121 | (1S,2R,3R,4aR,6aS,7R,8R, 10aR,10bR,12aR)-3-(acetyloxy)-2-(2-(3-acetylamino-pyrrolidin-1-yl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | 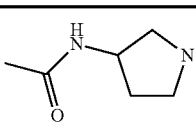 | Calculated for $C_{40}H_{62}N_2O_8$: 698. Observed: 699 (M + H)$^+$. | 0.64 (s, 3 H) 0.71 (s, 3 H) 0.74 (d, J = 7.14 Hz, 3 H) 0.82 (d, J = 6.65 Hz, 3 H) 0.87 (d, J = 6.71 Hz, 3 H) 1.12 (s, 3 H) 1.18 (s, 3 H) 1.20-1.28 (m, 3 H) 1.31-1.39 (m, 1 H) 1.39-1.49 (m, 2 H) 1.51-1.64 (m, 2 H) 1.64-1.84 (m, 5 H) 1.89-1.92 (m, 1 H) 1.94 (s, 3 H) 1.95 (s, 3 H) 1.99-2.07 (m, 2 H) 2.11-2.19 (m, 1 H) 2.21-2.31 (m, 1 H) 2.37-2.48 (m, 2 H) 2.62-2.71 (m, 1 H) 2.82 (s, 1 H) 2.82-2.97 (m, 1 H) 3.04-3.18 (m, 1 H) 3.30-3.45 (m, 4 H) 3.50 (d, J = 11.66 Hz, 1 H) 3.65 (d, J = 13.67 Hz, 1 H) 4.46-4.56 (m, 1 H) 4.91 (d, J = 8.85 Hz, 1 H) 5.38-5.47 (m, 1 H) 5.80-5.89 (m, 1 H) 6.77-6.91 (m, 1 H) |
| 122 | (1S,2R,3R,4aR,6aS,7R,8R, 10aR,10bR,12aR)-3-(acetyloxy)-2-(2-(1-methyl-pyrrolidin-3-ylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | 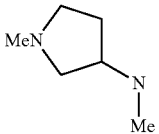 | Calculated for $C_{40}H_{64}N_2O_7$: 684. Observed: 685 (M + H)$^+$. | 0.64 (s, 3 H) 0.71 (s, 3 H) 0.74 (d, J = 7.14 Hz, 3 H) 0.82 (d, J = 6.65 Hz, 3 H) 0.88 (d, J = 6.77 Hz, 3 H) 1.13 (s, 3 H) 1.18 (s, 3 H) 1.20-1.29 (m, 3 H) 1.32-1.38 (m, 1 H) 1.39-1.48 (m, 2 H) 1.51-1.63 (m, 2 H) 1.65-1.70 (m, 1 H) 1.72-1.81 (m, 3 H) 1.90-1.93 (m, 2 H) 1.93 (d, J = 2.01 Hz, 3 H) 1.98-2.09 (m, 3 H) 2.11-2.20 (m, 1 H) 2.34 (d, J = 3.30 Hz, 3 H) 2.39-2.46 (m, 1 H) 2.51 (d, J = 4.46 Hz, 3 H) 2.58-2.71 (m, 1 H) 2.77-2.84 (m, 2 H) 2.96-3.07 (m, 1 H) 3.08-3.17 (m, 1 H) 3.26-3.45 (m, 5 H) 3.50 (d, J = 11.60 Hz, 1 H) 3.65 (d, J = 12.02 Hz, 1 H) 4.89 (dd, J = 9.34, 4.21 Hz, 1 H) 5.43 (s, 1 H) 5.78-5.87 (m, 1 H) |

-continued

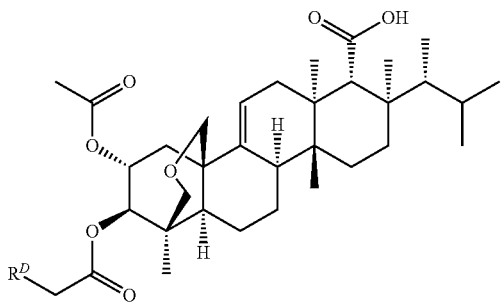
(ID)

| Example # | Compound Name | $R^D$ | Mass | $^1$H NMR (400 MHz, MeOH-d4) δ |
|---|---|---|---|---|
| 123 | (1S,2R,3R,4aR,6aS,7R,8R,10aR,10bR,12aR)-3-(acetyloxy)-2-(2-(3-dimethylamino-pyrrolidin-1-yl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | Me$_2$N–[pyrrolidine]–N | Calculated for $C_{40}H_{64}N_2O_7$: 684. Observed: 685 (M + H)$^+$. | 0.63 (s, 3 H) 0.71 (s, 3 H) 0.74 (d, J = 7.14 Hz, 3 H) 0.82 (d, J = 6.65 Hz, 3 H) 0.88 (d, J = 6.71 Hz, 3 H) 1.13 (s, 3 H) 1.18 (s, 3 H) 1.20-1.28 (m, 3 H) 1.31-1.38 (m, 1 H) 1.39-1.49 (m, 1 H) 1.51-1.64 (m, 2 H) 1.64-1.71 (m, 1 H) 1.72-1.81 (m, 3 H) 1.88-1.98 (m, 2 H) 1.93 (s, 3 H) 1.99-2.11 (m, 3 H) 2.12-2.21 (m, 1 H) 2.40 (d, J = 9.52 Hz, 6 H) 2.64-2.86 (m, 3 H) 2.80 (s, 1 H) 2.86-2.94 (m, 1 H) 3.19-3.44 (m, 4 H) 3.47 (s, 1 H) 3.51 (d, J = 11.66 Hz, 2 H) 3.65 (dd, J = 11.96, 3.54 Hz, 1 H) 4.90 (dd, J = 9.06, 3.57 Hz, 1 H) 5.44 (s, 1 H) 5.78-5.89 (m, 1 H) |
| 124 | (1S,2R,3R,4aR,6aS,7R,8R,10aR,10bR,12aR)-3-(acetyloxy)-2-(2-(4-isopropyl-piperazin-1-yl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | Me$_2$CH–[piperazine]–N | Calculated for $C_{41}H_{66}N_2O_7$: 698. Observed: 699 (M + H)$^+$. | 0.62 (s, 3 H) 0.71 (s, 3 H) 0.74 (d, J = 7.14 Hz, 3 H) 0.82 (d, J = 6.65 Hz, 3 H) 0.87 (d, J = 6.77 Hz, 3 H) 1.12 (s, 3 H) 1.14 (d, J = 5.74 Hz, 6 H) 1.18 (s, 3 H) 1.19-1.29 (m, 3 H) 1.28-1.37 (m, 1 H) 1.38-1.47 (m, 2 H) 1.49-1.69 (m, 4 H) 1.69-1.81 (m, 3 H) 1.88 (s, 3 H) 1.91-2.08 (m, 4 H) 2.12-2.23 (m, 1 H) 2.32-2.45 (m, 1 H) 2.59-2.95 (m, 8 H) 2.98-3.11 (m, 1 H) 3.22 (q, J = 17.17 Hz, 2 H) 3.33 (d, J = 11.90 Hz, 1 H) 3.37 (d, J = 11.96 Hz, 1 H) 3.52 (d, J = 11.66 Hz, 1 H) 3.64 (d, J = 11.96 Hz, 1 H) 4.88 (d, J = 9.16 Hz, 1 H) 5.45 (s, 1 H) 5.74-5.85 (m, 1 H) |

-continued (ID)

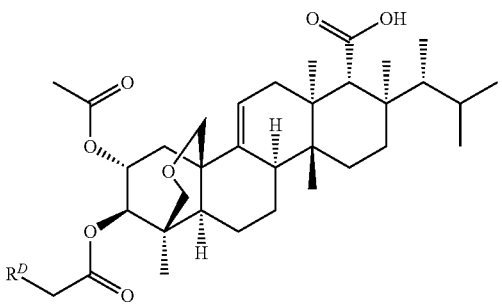

| Example # | Compound Name | R$^D$ | Mass | $^1$H NMR (400 MHz, MeOH-d4) δ |
|---|---|---|---|---|
| 125 | (1S,2R,3R,4aR,6aS,7R,8R,10aR,10bR,12aR)-3-(acetyloxy)-2-(2-(3-diethylamino-pyrrolidin-1-yl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | Et$_2$N-pyrrolidinyl | Calculated for C$_{42}$H$_{68}$N$_2$O$_7$: 712. Observed: 713 (M + H)$^+$. | 0.63 (s, 3 H) 0.70 (s, 3 H) 0.74 (d, J = 7.14 Hz, 3 H) 0.82 (d, J = 6.65 Hz, 3 H) 0.87 (d, J = 6.71 Hz, 3 H) 1.12 (s, 3 H) 1.15 (d, J = 7.08 Hz, 6 H) 1.18 (s, 3 H) 1.19-1.28 (m, 3 H) 1.30-1.38 (m, 1 H) 1.39-1.48 (m, 2 H) 1.50-1.62 (m, 2 H) 1.63-1.70 (m, 1 H) 1.71-1.81 (m, 3 H) 1.89-1.92 (m, 1 H) 1.93 (s, 3 H) 1.96-2.10 (m, 5 H) 2.12-2.22 (m, 1 H) 2.37-2.47 (m, 1 H) 2.60-2.72 (m, 1 H) 2.75-2.91 (m, 5 H) 2.91-2.98 (m, 1 H) 3.22-3.46 (m, 4 H) 3.50 (d, J = 11.54 Hz, 1 H) 3.54-3.61 (m, 1 H) 3.64 (d, J = 11.90 Hz, 1 H) 4.90 (dd, J = 9.06, 4.49 Hz, 1 H) 5.43 (s, 1 H) 5.77-5.87 (m, 1 H) |
| 126 | (1S,2R,3R,4aR,6aS,7R,8R,10aR,10bR,12aR)-3-(acetyloxy)-2-(2-[methyl-(1-methylpiperidin-4-yl)-amino]acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | MeN-piperidinyl-N(Me) | Calculated for C$_{41}$H$_{66}$N$_2$O$_7$: 698. Observed: 699 (M + H)$^+$. | 0.65 (s, 3 H) 0.71 (s, 3 H) 0.75 (d, J = 7.14 Hz, 3 H) 0.82 (d, J = 6.65 Hz, 3 H) 0.88 (d, J = 6.77 Hz, 3 H) 1.12 (s, 3 H) 1.18 (s, 3 H) 1.20-1.27 (m, 4 H) 1.32-1.39 (m, 2 H) 1.40-1.49 (m, 2 H) 1.50-1.72 (m, 5 H) 1.72-1.82 (m, 4 H) 1.88-1.92 (m, 1 H) 1.94 (s, 2 H) 1.96 (s, 3 H) 1.98-2.04 (m, 1 H) 2.05 (s, 3 H) 2.10-2.16 (m, 1 H) 2.38 (s, 2 H) 2.40-2.47 (m, 1 H) 2.74 (s, 3 H) 2.84 (s, 1 H) 3.30-3.43 (m, 4 H) 3.50 (d, J = 11.60 Hz, 1 H) 3.69 (d, J = 11.96 Hz, 1 H) 4.88 (d, J = 9.34 Hz, 1 H) 5.41 (s, 1 H) 5.77-5.90 (m, 1 H) |

(ID)

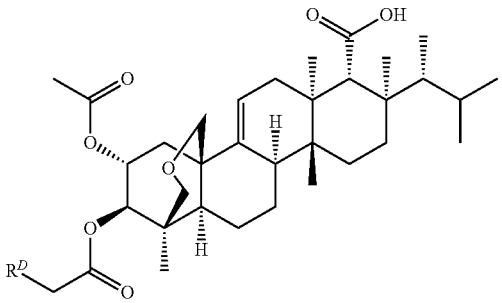

| Example # | Compound Name | $R^D$ | Mass | $^1$H NMR (400 MHz, MeOH-d4) δ |
|---|---|---|---|---|
| 127 | (1S,2R,3R,4aR,6aS,7R,8R, 10aR,10bR,12aR)-3-(acetyloxy)-2-(2-[1,4']Bipiperidinyl-1'-yl-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid | | Calculated for $C_{44}H_{70}N_2O_7$: 738. Observed: 739 (M + H)$^+$. | 0.60 (s, 3 H) 0.70 (s, 3 H) 0.73 (d, J = 7.20 Hz, 3 H) 0.83 (d, J = 6.65 Hz, 3 H) 0.86 (d, J = 6.77 Hz, 3 H) 1.13 (s, 3 H) 1.14-1.19 (m, 1 H) 1.20 (s, 3 H) 1.27-1.35 (m, 2 H) 1.35-1.60 (m, 6 H) 1.60-1.79 (m, 10 H) 1.83 (s, 3 H) 1.84-1.91 (m, 2 H) 1.99 (s, 3 H) 2.18-2.48 (m, 4 H) 2.67-3.01 (m, 9 H) 3.18 (d, J = 16.85 Hz, 1 H) 3.24-3.43 (m, 3 H) 3.49 (d, J = 11.66 Hz, 1 H) 3.64 (d, J = 11.90 Hz, 1 H) 4.84 (d, J = 8.97 Hz, 1 H) 5.42 (s, 1 H) 5.75-5.91 (m, 1 H) |

Example 128

(1S, 2R, 3R, 4aR, 6aS, 7R, 8R, 10aR, 10bR, 12aR)-3-(Acetyloxy)-2-(2-aminoacetoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid

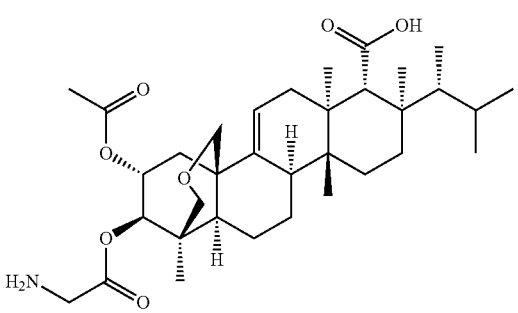

DCC (27 mg), DMAP (16 mg), and Cbz-Gly-OH (27 mg) were added to a solution of Intermediate 3 (30 mg; 0.05 mmol) in THF (3 mL). The reaction was stirred at RT for 16 hours and judged complete by TLC analysis. The reaction contents were concentrated, resuspended in MeOH, and filtered through a 0.2 μm ACRODISC. The filtrate was purified by reverse-phase HPLC (40:60 to 100:0 MeOH:H$_2$O). The purified material (20 mg) was collected from the relevant fractions and redissolved in MeOH (1.5 mL). EtOAc (10 μL) and PdOH (50 mg) were added, and H$_2$ atmosphere was secured (balloon). The reaction stirred at RT for 1 hour and was judged complete by TLC analysis. The reaction contents were filtered over CELITE and concentrated to yield the title compound (18.4 mg). Calculated for $C_{34}H_{51}NO_8$: 601. Observed: 602 (M+H)$^+$. $^1$H NMR (400 MHz, MeOH-d4) δ ppm 0.76 (s, 3 H) 0.79 (d, J=7.27 Hz, 3 H) 0.82 (s, 3 H) 0.89 (d, J=6.64 Hz, 3 H) 0.97 (d, J=6.69 Hz, 3 H) 1.11 (s, 3 H) 1.17-1.45 (m, 3 H) 1.45-1.67 (m, 2 H) 1.70-1.72 (m, 1 H) 1.73 (s, 3 H) 1.78-1.86 (m, 1 H) 1.87-1.97 (m, 4 H) 1.99 (s, 6 H) 2.19-2.30 (m, 1 H) 2.46-2.57 (m, 1 H) 2.68-2.79 (m, 1 H) 3.12 (s, 1 H) 3.49 (d, J=11.86 Hz, 1 H) 3.52-3.64 (m, 2 H) 3.73 (d, J=12.20 Hz, 1 H) 3.84 (d, 1 H) 3.97 (d, 1 H) 5.05 (d, J=9.22 Hz, 1 H) 5.80 (d, J=2.54 Hz, 1 H) 5.87-6.01 (m, 1 H).

In a similar manner as described in Example 128, using an appropriately protected amino acid, the following compounds of formula (IA) were prepared, where the $R^A$ group is connected to the remainder of the molecule via the right-most bond shown in the $R^A$ group:

| Example # | Compound Name | $R^4$ | Mass | $^1$H NMR (400 MHz, MeOH-d4) δ |
|---|---|---|---|---|
| 129 | (1S,2R,3R,4aR,6aS,7R,8R, 10aR,10bR,12aR)-3-(acetyloxy)-2-(pyrrolidine-2-carbonyloxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid | 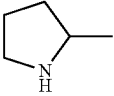 | Calculated for $C_{37}H_{55}NO_8$: 641. Observed: 642 (M + H)+. | 0.73-0.76 (m, 3 H) 0.79 (d, J = 7.27 Hz, 3 H) 0.82 (s, 3 H) 0.89 (d, J = 6.69 Hz, 3 H) 0.97 (d, J = 6.69 Hz, 3 H) 1.11 (s, 3 H) 1.16-1.53 (m, 6 H) 1.53-1.68 (m, 3 H) 1.69-1.72 (m, 1 H) 1.73 (s, 3 H) 1.75-1.86 (m, 1 H) 1.87-1.96 (m, 4 H) 1.99 (s, 3 H) 2.02-2.19 (m, 4 H) 2.20-2.31 (m, 1 H) 2.43-2.61 (m, 2 H) 2.68-2.77 (m, 1 H) 3.12 (s, 1 H) 3.33-3.46 (m, 2 H) 3.48-3.64 (m, J = 12.40 Hz, 3 H) 3.73 (d, J = 12.20 Hz, 1 H) 4.38-4.50 (m, 1 H) 5.05 (d, J = 8.79 Hz, 1 H) 5.80 (d, J = 2.59 Hz, 1 H) 5.88-6.00 (m, 1 H) |
| 130 | (1S,2R,3R,4aR,6aS,7R,8R, 10aR,10bR,12aR)-3-(acetyloxy)-2-(2,5-diaminopentanoyloxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid | 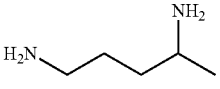 | Calculated for $C_{37}H_{58}N_2O_8$: 658. Observed: 659 (M + H)+. | 0.74-0.81 (m, J = 6.49, 6.49 Hz, 6 H) 0.82 (s, 3 H) 0.89 (d, J = 6.74 Hz, 3 H) 0.97 (d, J = 6.74 Hz, 3 H) 1.11 (s, 3 H) 1.15-1.45 (m, 4 H) 1.45-1.51 (m, 1 H) 1.51-1.68 (m, 3 H) 1.70-1.72 (m, 1 H) 1.73 (s, 3 H) 1.76-1.85 (m, 2 H) 1.86-1.98 (m, 6 H) 2.00 (s, 3 H) 2.02 (s, 3 H) 2.13-2.28 (m, 2 H) 2.41-2.56 (m, 1 H) 2.69-2.78 (m, 1 H) 2.97-3.08 (m, 2 H) 3.12 (s, 1 H) 3.48-3.64 (m, 3 H) 3.72-3.82 (m, 1 H) 4.07-4.23 (m, 1 H) 5.07 (t, J = 9.59 Hz, 1 H) 5.80 (d, J = 2.15 Hz, 1 H) 5.90-6.07 (m, 1 H) |
| 131 | (1S,2R,3R,4aR,6aS,7R,8R, 10aR,10bR,12aR)-3-(acetyloxy)-2-(2-(2-aminoacetylamino)-acetoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid | 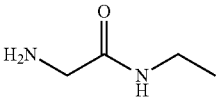 | Calculated for $C_{36}H_{54}N_2O_9$: 658. Observed: 659 (M + H). | 0.72-0.84 (m, 9 H) 0.89 (d, J = 6.64 Hz, 3 H) 0.97 (d, J = 6.69 Hz, 3 H) 1.11 (s, 3 H) 1.14-1.25 (m, 1 H) 1.29-1.45 (m, 1 H) 1.44-1.65 (m, 4 H) 1.73 (s, 3 H) 1.75-1.84 (m, 1 H) 1.87-1.97 (m, 4 H) 1.99 (s, 6 H) 2.18-2.30 (m, 1 H) 2.45-2.56 (m, 1 H) 2.69-2.78 (m, 1 H) 3.12 (s, 1 H) 3.49 (d, J = 12.10 Hz, 1 H) 3.59 (d, 4 H) 3.73 (d, J = 12.30 Hz, 1 H) 3.80-3.89 (m, 1 H) 3.97 (d, 1 H) 5.05 (d, J = 9.27 Hz, 1 H) 5.80 (d, J = 2.54 Hz, 1 H) 5.87-6.00 (m, 1 H) |

-continued

| Example # | Compound Name | R^A | Mass | $^1$H NMR (400 MHz, MeOH-d4) δ |
|---|---|---|---|---|
| 132 | (1S,2R,3R,4aR,6aS,7R,8R, 10aR,10bR,12aR)-3-(acetyloxy)-2-(2-(2-methylamino-acetylamino)-acetoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid | 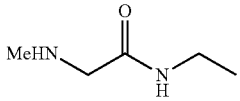 | Calculated for $C_{37}H_{56}N_2O_9$: 672. Observed: 673 (M + H)$^+$. | 0.65 (s, 3 H) 0.71 (d, J = 7.08 Hz, 3 H) 0.74 (s, 3 H) 0.81 (d, J = 6.54 Hz, 3 H) 0.89 (d, J = 6.74 Hz, 3 H) 1.03 (s, 3 H) 1.06-1.29 (m, 5 H) 1.30-1.43 (m, 2 H) 1.43-1.59 (m, 2 H) 1.65 (s, 3 H) 1.67-1.77 (m, 1 H) 1.77-1.89 (m, 3 H) 1.92 (s, 3 H) 1.94-1.99 (m, 1 H) 2.10-2.25 (m, 2 H) 2.32-2.41 (m, 1 H) 2.66 (s, 3 H) 3.04 (s, 1 H) 3.40 (d, J = 11.13 Hz, 1 H) 3.44-3.54 (m, 2 H) 3.64 (d, J = 12.40 Hz, 1 H) 3.77 (s, 2 H) 3.96 (d, J = 8.30 Hz, 2 H) 4.35-4.42 (m, 1 H) 4.87 (d, J = 9.08 Hz, 1 H) 5.71 (s, 1 H) 5.80-5.94 (m, 1 H) |
| 133 | (1S,2R,3R,4aR,6aS,7R,8R, 10aR,10bR,12aR)-3-(acetyloxy)-2-(2,6-diamino-hexanoyloxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid | 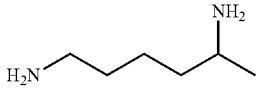 | Calculated for $C_{38}H_{60}N_2O_8$: 672. Observed: 673 (M + H)$^+$. | 0.76-0.80 (m, J = 7.22 Hz, 3 H) 0.82 (s, 3 H) 0.89 (d, J = 6.64 Hz, 3 H) 0.97 (d, J = 6.64 Hz, 3 H) 1.11 (s, 3 H) 1.34 (s, 3 H) 1.37-1.58 (m, 8 H) 1.58-1.70 (m, 7 H) 1.74 (s, 3 H) 1.98 (s, 3 H) 2.17-2.31 (m, 1 H) 2.44-2.57 (m, 1 H) 2.62-2.80 (m, 1 H) 3.11 (s, 1 H) 3.29-3.33 (m, 2 H) 3.59 (s, 5 H) 3.68-3.81 (m, 1 H) 4.94-5.06 (m, 2 H) 5.81 (s, 1 H) 5.86-6.03 (m, 1 H) |
| 134 | (1S,2R,3R,4aR,6aS,7R,8R, 10aR,10bR,12aR)-3-(acetyloxy)-2-( (4-aminopyrrolidine)-2-carbonyloxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid | 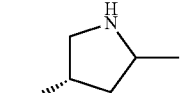 | Calculated for $C_{37}H_{56}N_2O_8$: 656. Observed: 657 (M + H)$^+$. | 0.77-0.81 (m, J = 7.13 Hz, 4 H) 0.82 (s, 3 H) 0.89 (d, J = 5.71 Hz, 3 H) 0.97 (d, J = 6.54 Hz, 3 H) 1.11 (s, 3 H) 1.17-1.38 (m, 3 H) 1.38-1.65 (m, 7 H) 1.73 (s, 3 H) 1.95 (s, 3 H) 1.97 (s, 7 H) 2.15-2.30 (m, 2 H) 3.11 (s, 1 H) 3.46-3.67 (m, 4 H) 3.66-3.91 (m, 3 H) 4.94-5.05 (m, 1 H) 5.72-5.87 (m, 1 H) 5.88-6.04 (m, 1 H) |
| 135 | (1S,2R,3R,4aR,6aS,7R,8R, 10aR,10bR,12aR)-3-(acetyloxy)-2-(2-amino-5-guanidino-pentanoyloxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid | 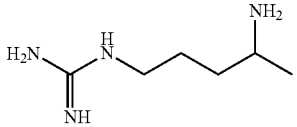 | Calculated for $C_{38}H_{60}N_4O_8$: 700. Observed: 701 (M + H)$^+$. | 0.74-0.80 (m, 3 H) 0.82 (s, 3 H) 0.89 (d, J = 6.64 Hz, 3 H) 0.97 (d, J = 6.69 Hz, 3 H) 1.11 (s, 3 H) 1.18-1.63 (m, 8 H) 1.73 (s, 3 H) 1.75-1.94 (m, 6 H) 1.99 (s, 4 H) 2.10-2.34 (m, 2 H) 2.42-2.56 (m, 1 H) 2.67-2.78 (m, 1 H) 3.11 (s, 1 H) 3.17-3.40 (m, 4 H) 3.46-3.63 (m, 2 H) 3.68-3.81 (m, 1 H) 4.00-4.25 (m, 2 H) 5.03-5.14 (m, 1 H) 5.79 (s, 1 H) 5.88-6.08 (m, 1 H) |

Example 136

(1S, 2R, 3R, 4aR, 6aS, 7R, 8R, 10aR, 10bR, 12aR)-2-(2,6-diaminohexanoyloxy)-3-(methoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid

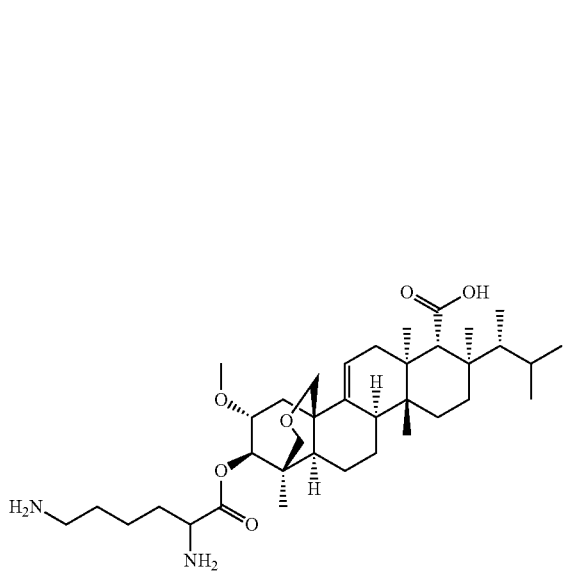

DCC (41 mg), DMAP (24 mg), and Cbz-Lys-OH (83 mg) were added to a solution of Intermediate 2 (30 mg) in THF (4 mL). The reaction was stirred at RT for 3 hours and judged complete by TLC analysis. The reaction contents were concentrated and resuspended in MeOH. The contents were filtered through a 0.2 μm ACRODISC filter, and the filtrate was purified using reverse-phase HPLC (70:30 to 100:0 MeOH:H$_2$O). Product was collected by concentrating relevant fractions and dissolved in MeOH (2 mL) with 2 drops of DCM added to aid dissolution. PdOH (50 mg) and 1 drop HOAc were added, and H$_2$ atmosphere was secured (balloon). The reaction mixture was stirred at RT for 1 hour and judged complete by TLC. The reaction contents were filtered over a pad of CELITE and concentrated to yield the title compound (24 mg). Calculated for C$_{37}$H$_{62}$N$_2$O$_6$: 630. Observed: 631 (M+H)$^+$. $^1$H NMR (400 MHz, MeOH-d4) δ ppm 0.67 (s, 3 H) 0.74-0.82 (m, 6 H) 0.87 (d, J=6.69 Hz, 3 H) 0.92 (d, J=6.78 Hz, 3 H) 0.93 (s, 3 H) 1.23 (s, 3 H) 1.26-1.36 (m, 3 H) 1.39-1.46 (m, 1 H) 1.46-1.67 (m, 5 H) 1.67-1.76 (m, 4 H) 1.77-1.90 (m, 4 H) 1.93-2.05 (m, 2 H) 2.08-2.18 (m, 1 H) 2.17-2.28 (m, 1 H) 2.52-2.64 (m, 1 H) 2.86 (s, 1 H) 2.94 (t, J=7.64 Hz, 2 H) 3.33 (s, 3 H) 3.40-3.55 (m, 3 H) 3.63 (d, J=12.01 Hz, 1 H) 3.86 (t, 1 H) 4.25-4.39 (m, 1 H) 4.81 (d, J=9.03 Hz, 1 H) 5.56 (m, 1 H).

Example 137

(1S, 2R, 3R, 4aR, 6aS, 7R, 8R, 10aR, 10bR, 12aR)-2-(2,6-diaminohexanoyloxy)-3-(ethoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid

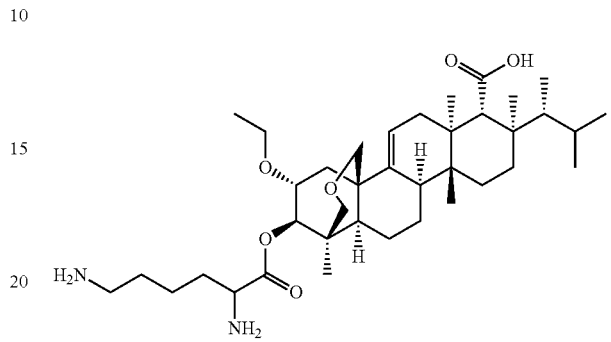

The title compound was obtained as described in Example 136, from Intermediate 2 and EtOH. Calculated for C$_{38}$H$_{64}$N$_2$O$_6$: 644. Observed: 645 (M+H)$^+$. $^1$H NMR (400 MHz, MeOH-d4) δ ppm 0.68 (s, 3 H) 0.79 (d, 6 H) 0.87 (d, J=6.69 Hz, 3 H) 0.92 (d, J=6.78 Hz, 2 H) 1.13 (t, J=6.98 Hz, 3 H) 1.19 (s, 3 H) 1.23 (s, 3 H) 1.25-1.46 (m, 5 H), 1.46-1.66 (m, 5 H) 1.68-1.88 (m, 6 H) 1.88-2.02 (m, 3 H) 2.02-2.09 (m, 1 H) 2.10-2.17 (m, 1 H) 2.17-2.26 (m, 1 H) 2.49-2.61 (m, 1 H) 2.87 (s, 1 H) 2.96 (t, J=7.71 Hz, 2 H) 3.39-3.52 (m, 5 H) 3.58-3.69 (m, 2 H) 3.99-4.08 (m, 1 H) 4.37-4.48 (m, 1 H) 5.56 (d, J=5.66 Hz, 1 H).

Example 138

(1S, 2R, 3R, 4aR, 6aS, 7R, 8R, 10aR, 10bR, 12aR)-2-(2,6-diamino-hexanoyloxy)-3-((2-methyl)ethoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid

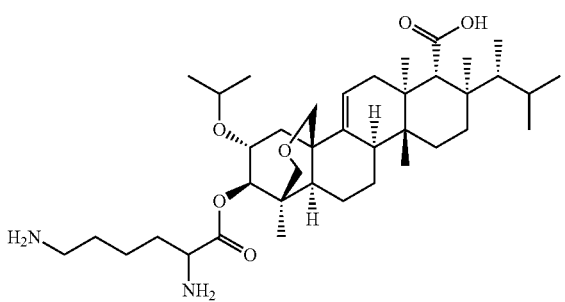

The title compound was obtained as described in Example 136, from Intermediate 2 and 2-propanol. Calculated for C$_{39}$H$_{66}$N$_2$O$_6$: 658. Observed: 659 (M+H)$^+$. $^1$H NMR (400 MHz, MeOH-d4) δ ppm 0.65-0.70 (m, 3 H) 0.76-0.82 (m, 6 H) 0.87 (d, J=6.64 Hz, 3 H) 0.92 (d, J=6.78 Hz, 3 H) 1.11 (dd, J=10.88, 6.05 Hz, 6 H) 1.19 (s, 3 H) 1.23 (s, 3 H) 1.24-1.33

(m, 4 H) 1.34-1.46 (m, 2 H) 1.47-1.90 (m, 12 H) 1.94-1.98 (m, 1 H) 1.99 (s, 3 H) 2.08-2.18 (m, 2 H) 2.18-2.25 (m, 1 H) 2.44-2.56 (m, 1 H) 2.86 (s, 1 H) 2.94-3.01 (m, 2 H) 3.41-3.53 (m, 3 H) 3.57-3.68 (m, 1 H) 3.69-3.79 (m, 1 H) 4.06-4.22 (m, 1 H) 4.43-4.57 (m, 1 H) 5.56 (s, 1 H).

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A compound of Formula (I)

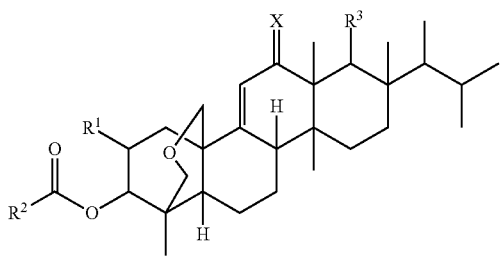

(I)

or a pharmaceutically acceptable salt or prodrug thereof, wherein:

X is selected from the group consisting of O and H,H;

$R^1$ is selected from the group consisting of:
 a) OH,
 b) O—$(C_1-C_{12})$alkyl,
 c) O—$(C_3-C_8)$cycloalkyl,
 d) O-heterocyclyl,
 e) OC(O)H,
 f) OC(O)—$(C_1-C_{12})$alkyl,
 g) OC(O)—$(C_3-C_8)$cycloalkyl, and
 h) OC(O)-(heterocyclyl),
  where said heterocyclyl groups are chosen from 5- to 8-membered rings containing from 1 to 4 heteroatoms independently selected from N, O and S;

$R^2$ is selected from the group consisting of:
 a) $(C_1-C_{12})$alkyl, and
 b) heterocyclyl, where said heterocyclyl groups are chosen from 5- to 8-membered rings containing from 1 to 4 heteroatoms independently selected from N, O and S, and
 said $R^2$ is substituted by 0 to 4 $R^4$ groups;

$R^3$ is selected from the group consisting of:
 a) $CH_2OH$,
 b) $CH_2OC(O)(C_1-C_{12}$ alkyl),
 c) COOH,
 d) $COO(C_1-C_{12})$alkyl, and
 e) $COO(CH_2)_{0-6}$phenyl;

each $R^4$ is independently selected from the group consisting of:
 a) $(C_1-C_{12})$alkyl,
 b) $(C_3-C_8)$cycloalkyl,
 c) OH,
 d) $NR^5_2$,
 e) $ONR^5_2$,
 f) $O(C_1-C_{12})$alkyl,
 g) $C(O)R^6$,
 h) $S(O)_2R^6$, and
 i)

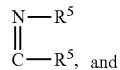

said $R^4$ is substituted by 0 to 4 $R^7$ groups;

each $R^5$ is independently selected from the group consisting of:
 a) H,
 b) $(CH_2)_{0-12}R^6$,
 c) $C(O)R^6$,
 d) $S(O)_2R^6$, and
 e)

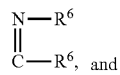

said $R^5$ is substituted by 0 to 13 $R^7$ groups;

each $R^6$ is independently selected from the group consisting of:
 a) H,
 b) OH,
 c) $(C_1-C_{12})$alkyl,
 d) O—$(C_1-C_{12})$alkyl,
 e) $(C_3-C_{12})$cycloalkyl,
 f) $(CH_2)_{0-6}$-phenyl,
 g) heterocyclyl, where said heterocyclyl groups are chosen from 5- to 8-membered rings containing from 1 to 4 heteroatoms independently selected from N, O and S,
 h) $C(O)R^8$,
 i) $NR^8_2$,
 j) halogen, and
 said $R^6$ is substituted by 0 to 13 $R^7$ groups;

each $R^7$ is independently selected from the group consisting of:
 a) OH,
 b) $(C_1-C_{12})$alkyl,
 c) O—$(C_1-C_{12})$alkyl,
 d) S—$(C_1-C_{12})$alkyl,
 e) $(CH_2)_{0-6}$-phenyl,
 f) heterocyclyl, where said heterocyclyl groups are chosen from 5- to 8-membered rings containing from 1 to 4 heteroatoms independently selected from N, O and S,
 g) $C(O)R^8$,
 h) $OC(O)R^8$,
 i) $NR^8_2$,
 j) halogen, and
 said $R^7$ is substituted by 0 to 13 $R^9$ groups;

each $R^8$ is independently selected from the group consisting of:
 a) H,
 b) $(C_1-C_{12})$alkyl,
 c) O—$(C_1-C_{12})$alkyl,
 d) $(C_3-C_{12})$cycloalkyl,
 e) $(CH_2)_{0-6}$-phenyl, f) heterocyclyl, where said heterocyclyl groups are chosen from 5- to 8-membered rings containing from 1 to 4 heteroatoms independently selected from N, O and S,
g) $C(O)R^{11}$, and
said $R^8$ is substituted by 0 to 13 $R^9$ groups;
each $R^9$ is independently selected from the group consisting of:
  a) OH,
  b) $(C_1-C_{12})$alkyl,
  c) $O-(C_1-C_{12})$alkyl,
  d) $(C_3-C_{12})$cycloalkyl,
  e) heterocyclyl, where said heterocyclyl groups are chosen from 5- to 8-membered rings containing from 1 to 4 heteroatoms independently selected from N, O and S,
  f) $C(O)R^{11}$,
  g) $NR^{11}{}_2$,
  h) halogen, and
  said $R^9$ is substituted by 0 to 13 $R^{10}$ groups;
each $R^{10}$ is independently selected from the group consisting of:
  a) halogen,
  b) =O, and
  c) $C(O)R^{11}$; and
$R^{11}$ is selected from the group consisting of:
  a) H, and
  b) $(C_1-C_{12})$alkyl.

2. The compound according to claim 1, wherein the compound has structural Formula (Ia):

(Ia)

3. The compound according to claim 1, wherein X is O.

4. The compound according to claim 1, wherein $R^1$ is selected from the group consisting of OC(O)H and OC(O)—$(C_1-C_{12})$alkyl.

5. The compound according to claim 1, wherein
$R^2$ is selected from the group consisting of $(C_1-C_{12})$alkyl that are substituted by 1 to 4 $R^4$ groups; and
said $R^4$ groups are independently selected from the group consisting of OH, $NR^5{}_2$, $O(C_1-C_{12})$alkyl, $C(O)R^6$ and $S(O)_2R^6$.

6. The compound according to claim 5, wherein
said $R^4$ groups are independently selected from the group consisting of $NR^5{}_2$, $C(O)R^6$ and $S(O)_2R^6$;
each $R^5$ is independently selected from the group consisting of H and $(CH_2)_{0-12}R^6$;
$R^6$ is selected from the group consisting of H, OH and $(C_1-C_{12})$alkyl; and
said $R^6$ is substituted by 0 to 2 $NH_2$ groups.

7. The compound according to claim 5, wherein
said $R^2$ is substituted by $NH_2$ and $NHR^5$;
$R^5$ is selected from the group consisting of H and $(CH_2)_{0-12}R^6$; and $R^6$ is selected from the group consisting of $(C_1-C_{12})$alkyl, $(C_3-C_{12})$cycloalkyl, $(CH_2)_{0-6}$phenyl, and heterocyclyl.

8. The compound according to claim 7, wherein
said $R^6$ is substituted by 0 to 4 $R^7$; and
each $R^7$ is independently selected from halogen and $O(C_1-C_{12})$alkyl groups.

9. The compound according to claim 1, wherein $R^2$ is selected from the group consisting of heterocyclyl, where said heterocyclyl group is a 5- to 6-membered ring containing from 1 to 4 heteroatoms independently selected from N, O and S.

10. The compound according to claim 9, wherein
said $R^2$ is substituted by 1 to 4 $R^4$ groups; and
said $R^4$ groups are independently selected from the group consisting of OH, $NR^5{}_2$, $O(C_1-C_{12})$alkyl, $C(O)R^6$ and $S(O)_2R^6$.

11. The compound according to claim 10, wherein
said $R^4$ groups are independently selected from the group consisting of $NR^5{}_2$, $C(O)R^6$ and $S(O)_2R^6$;
each $R^5$ is independently selected from the group consisting of H and $(CH_2)_{0-12}R^6$;
$R^6$ is selected from the group consisting of H, OH and $(C_1-C_{12})$alkyl; and
said $R^6$ is substituted by 0 to 2 $NH_2$ groups.

12. The compound according to claim 1, wherein the compound is selected from the group consisting of
(1S, 2R, 3R, 4aR, 6aS, 7R, 8R, 10aR, 10bR, 12aR)-3-(acetyloxy)-2-(2-amino-3-methyl-butyryloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-4-carbamoyl-butyryloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-pentanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2,6-diamino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-4-hydroxy-butyryloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2,5-diamino-pentanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-butyryloxy)-8-[(1R)-1,2-dimethylpropyl]-1,6a,8,10a-tetramethyl-1,3,4,6,6a,7,8,9, 10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-3-carboxypropionyoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-piperidinylcarboxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-pyrrolidinylcarboxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(3-amino -propionyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(3-amino-butyryloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(3-amino-propionyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-5-formylamino-pentanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(4-amino-pyrrolidine-2-carboxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-guanidino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-acetylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-(2-methylamino-acetylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(4-hydroxy-pyrrolidine-2-carboxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-3-(2-amino-ethoxy)-propionyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-3-(2-amino-ethanesulfonyl)-propionyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-3-(2-amino-ethylamino)-propionyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-(2-amino-ethylamino)-acetoxy)-8-[(1R)-1,2-dimethylpropyl]-1,6a,8,10a-tetramethyl -1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(4-amino-5-hydroxy-pentanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-(N-hydroxycarbamimidoyl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-(N-(2,6-diaminohexanoyloxy)carbamimidoyl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a -(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-(3,5-bis-trifluoromethyl-benzoylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a -(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-(3-bromo-benzoylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-(2,2,3,3,4,4,4-heptafluoro-butyrylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a -(methanooxymethano)chrysene-7-carboxylic acid;

(1S, 2R, 3R, 4aR, 6aS, 7R, 8R, 10aR, 10bR, 12aR)-3-(acetyloxy)-2-(2-6-(2-bromo-propionylamino)-hexanoyloxy)-8-[(1R)-1,2-dimethylpropyl]-1,6a,8,10a-tetramethyl-1,3,4,6,6a,7,8,9,10,10a,10b,11,12,12a- tetradecahydro-2H-1,4a-(methanooxymethano)
chrysene-7-carboxylic acid;

(1S, 2R, 3R, 4aR, 6aS, 7R, 8R, 10aR, 10bR, 12aR)-3-(acetyloxy)-2-(2-amino-6-(2-methoxy-acetylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-[(tetrahydro-furan-2-carbonyl)-amino]-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-(3-methoxy-benzoylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a -(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-(3-fluoro-benzoylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-phenylacetylamino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-(cyclobutanecarbonyl-amino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-(3,5-dimethoxy-benzoylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-(2-oxo-propionylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-(3-chloro-benzoylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-propionylamino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-(4-chloro-benzoylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(6-(2-acetoxy-2-methyl-propionylamino)-2-amino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(6-acetylamino-2-amino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-(2,2,2-trifluoro-acetylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-[3-(4-fluoro-phenyl)-ureido]-hexanoyloxy hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-[3-(4-trifluoromethylphenyl)-ureido]-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-(3-isopropyl-ureido)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-[3-(4-methoxyphenyl)-ureido]-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-(3-cyclopentyl-ureido)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-[3-(1-methoxycarbonyl-ethyl)-ureido]-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-[3-(2-bromo-ethyl)-ureido]-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-[3-(2-chloro-ethyl)-ureido]-hexanoyloxy)-8-[(1R)-1,2-dimethylpropyl]-1,6a,8,10a-tetramethyl-1,3,4,6,6a,7,8,9,10,10a,10b,11,12, 12a-tetradecahydro-2H-1,4a-(methanooxymethano) chrysene-7-carboxylic acid;

(1S, 2R, 3R, 4aR, 6aS, 7R, 8R, 10aR, 10bR, 12aR)-3-(acetyloxy)-2-(2-amino-6-(3-hexylureido)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid;

(1S, 2R, 3R, 4aR, 6aS, 7R, 8R, 10aR, 10bR, 12aR)-3-(acetyloxy)-2-(2-amino-6-(3-phenyl-ureido)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4 a-(methanooxymethano) chrysene-7-carboxylic acid;

(1S, 2R, 3R, 4aR, 6aS, 7R, 8R, 10aR, 10bR, 12aR)-3-(acetyloxy)-2-(2-amino-6-[3-(4-methoxycarbonylphenyl)-ureido]-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a -(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-(3-ethoxycarbonylmethyureido)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid;

(1S, 2R, 3R, 4aR, 6aS, 7R, 8R, 10aR, 10bR, 12aR)-3-(acetyloxy)-2-(2-amino-6-(4-tert-butylbenzenesulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a -(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-(4-trifluoromethylbenzenesulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a -(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-(4-fluorobenzenesulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid;

(1S, 2R, 3R, 4aR, 6aS, 7R, 8R, 10aR, 10bR, 12aR)-3-(acetyloxy)-2-(2-amino-6-(4-bromobenzenesulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid;

(1S, 2R, 3R, 4aR, 6aS, 7R, 8R, 10aR, 10bR, 12aR)-3-(acetyloxy)-2-(2-amino-6-(4-methoxybenzenesulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid;

(1S, 2R, 3R, 4aR, 6aS, 7R, 8R, 10aR, 10bR, 12aR)-3-(acetyloxy)-2-(2-amino-6-(3,5-dimethylisoxazole-4-sulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a -(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-methanesulfonylamino-hexanoyloxy)-8-[(1 R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid;

(1S, 2R, 3R, 4aR, 6aS, 7R, 8R, 10aR, 10bR, 12aR)-3-(acetyloxy)-2-(2-amino-6-ethanesulfonylamino-hexanoyloxy)-8-[(1 R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid;

(1S, 2R, 3R, 4aR, 6aS, 7R, 8R, 10aR, 10bR, 12aR)-3-(acetyloxy)-2-(2-amino-6-propanesulfonylamino-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid;

(1S, 2R, 3R, 4aR, 6aS, 7R, 8R, 10aR, 10bR, 12aR)-3-(acetyloxy)-2-(2-amino-6-(3-chloropropane-1-sulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a -(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-(3,5-bis-trifluoromethylbenzenesulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a -(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-(3-trifluoromethylbenzenesulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a -(methanooxymethano)chrysene-7-carboxylic acid;

(1S, 2R, 3R, 4aR, 6aS, 7R, 8R, 10aR, 10bR, 12aR)-3-(acetyloxy)-2-(6-(4-acetylamino-benzenesulfonylamino)-2-amino-hexanoyloxy)-8-[(1R)-1,2-dimethylpropyl]-1,6a,8,10a -tetramethyl-1,3,4,6,6a,7,8,9,10,10a,10b,11,12,12a-tetradecahydro-2H-1,4a-(methanooxymethano)chrysene-7-carboxylic acid;

(1S, 2R, 3R, 4aR, 6aS, 7R, 8R, 10aR, 10bR, 12aR)-3-(acetyloxy)-2-(2-amino-6-(3-chloro-4-fluorobenzenesulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a -(methanooxymethano)chrysene-7-carboxylic acid;

(1S,2R,3R,4aR,6aS,7R,8R,10aR,10bR,12aR)-3-(acetyloxy)-2-(2-amino-6-(toluene-2-sulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid;

(1S,2R,3R,4aR,6aS,7R,8R,10aR,10bR,12aR)-3-(acetyloxy)-2-(2-amino-6-(3,4-dimethoxy-benzenesulfonylamino)-hexanoyloxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a -(methanooxymethano)chrysene-7-carboxylic acid;

(1S,2R,3R,4aR,6aS,7R,8R,10aR,10bR,12aR)-3-(acetyloxy)-2-(2-(2,2-dimethyl-propylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-[(tetrahydro-furan-2-ylmethyl)-amino]-acetoxy)-8-[(1R)-1,2-dimethylpropyl]-1,6a,8,10a-tetramethyl-1,3,4,6,6a,7,8,9,10,10a,10b,11,12,12a- tetradecahydro-2H-1,4a-(methanooxymethano) chrysene-7-carboxylic acid;

(1S,2R,3R,4aR,6aS,7R,8R,10aR,10bR,12aR)-3-(acetyloxy)-2-(2-[2-(4-fluoro-phenyl)-1-methyl-ethylamino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid;

(1S,2R,3R,4aR,6aS,7R,8R,10aR,10bR,12aR)-3-(acetyloxy)-2-(2-(tetrahydro-pyran-4-ylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-isopropylaminoacetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(2-methyl-tetrahydro-furan-3-ylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid;

(1S,2R,3R,4aR,6aS,7R,8R,10aR,10bR,12aR)-3-(acetyloxy)-2-(2-(1-methyl-3-methylsulfanyl-propylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid;

(1S,2R,3R,4aR,6aS,7R,8R,10aR,10bR,12aR)-3-(acetyloxy)-2-(2-(4-diethylamino-1-methyl-butylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid;

(1S,2R,3R,4aR,6aS,7R,8R,10aR,10bR,12aR)-3-(acetyloxy)-2-(2-[(1-Methyl-pyrrolidin-2-ylmethyl)-amino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid;

(1S,2R,3R,4aR,6aS,7R,8R,10aR,10bR,12aR)-3-(acetyloxy)-2-(2-(1-methyl-piperidin-4-ylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(2-methoxy-1-methyl-ethylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid;

(1S,2R,3R,4aR,6aS,7R,8R,10aR,10bR,12aR)-3-(acetyloxy)-2-(2-(2-methyl-cyclopentylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-guanidino-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(cyclopropylmethyl-propyl-amino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid;

(1S,2R,3R,4aR,6aS,7R,8R,10aR,10bR,12aR)-3-(acetyloxy)-2-(2-[bis-(2-hydroxy-ethyl)-amino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-[4-(4-fluoro-2-methoxyphenyl)-piperidin-1-yl]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid;

(1S,2R,3R,4aR,6aS,7R,8R,10aR,10bR,12aR)-3-(acetyloxy)-2-(2-(2-piperidin-1-ylethylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(3-imidazol-1-ylpropylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(cyclohexyl-methylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-pyrrolidin-1-yl-acetoxy)-8-[(1R)-1,2-dimethylpropyl]-1,6a,8,10a tetramethyl1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(3-hydroxy-pyrrolidin-1-yl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-[4-(4-fluoro-phenyl)-piperazin-1-yl]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano) chrysene-7-carboxylic acid;

(1S,2R,3R,4aR,6aS,7R,8R,10aR,10bR,12aR)-3-(acetyloxy)-2-(2-(4-methyl-piperazin-1-yl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-morpholin-4-yl-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-dimethylamino-acetoxy)-8-[(1R)-1,2-dimethylpropyl]-1,6a,8,10a-tetramethyl-1,3,4,6,6a,7,8,9, 10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-[(2,2-dimethoxyethyl)-methyl-amino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(ethyl-methyl-amino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-[(2-diethylamino-ethyl)-methylamino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(4-ethyl-piperazin-1-yl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(2-pyrrolidin-1-yl-ethylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-[3-(2-oxo-pyrrolidin-1-yl)-propylamino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(2-morpholin-4-yl-ethylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(1-ethoxycarbonylpiperidin-4-yl)-amino-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(2-methoxy-1-methyl-ethylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-methylamino-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(2-dimethylamino-ethylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(3-isopropoxy-propylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(1,2,2,6,6-pentamethyl-piperidin-4-ylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-[(piperidin-4-ylmethyl)-amino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-[3-(2-methyl-piperidin-1-yl)-propylamino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(3-methylamino-propylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(3-dimethylamino-propylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(3-pyrrolidin-1-yl-propylamino)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-[(3-dimethylaminopropyl)-methyl-amino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid (1S,2R,3R,4aR,6aS,7R,8R,10aR,10bR,12aR)-3-(acetyloxy)-2-(2-[bis-(3-dimethylaminopropyl)-amino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(4-pyrrolidin-1-yl-piperidin-1-yl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(3-acetylamino-pyrrolidin-1-yl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(1-methyl-pyrrolidin-3-ylamino)-acetoxy)-8-[(1R)-1,2-dimethylpropyl]-1,6a,8,10a-tetramethyl-1, 3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(3-dimethylamino-pyrrolidin-1-yl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(4-isopropyl-piperazin-1-yl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(3-diethylamino-pyrrolidin-1-yl)-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-[methyl-(1-methylpiperidin-4-yl)-amino]-acetoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-[1,4']Bipiperidinyl-1'-yl-acetoxy)-8-[(1R)-1,2-dimethylpropyl]-1,6a,8,10a-tetramethyl-1,3,4,6,6a,7,8,9,10,10a,10b,11,12,12a -tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-aminoacetoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(pyrrolidene-2-carbonyloxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2,5-diamino-pentanoyloxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(2-amino-acetylamino)-acetoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-(2-methylamino-acetylamino)-acetoxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2,6-diamino-hexanoyloxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-((4-aminopyrrolidine)-2-carbonyloxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-3-(acetyloxy)-2-(2-amino-5-guanidino-pentanoyloxy)-8-[(1R)-1,2-dimethylpropyl]-1,6a,8,10a-tetramethyl-6-oxo-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-2-(2,6-diamino-hexanoyloxy)-3-(methoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid;

(1S,2R,3R,4aR,6aS,7R,8R,10aR,10bR,12aR)-2-(2,6-diamino-hexanoyloxy)-3-(ethoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid; and (1S,2R,3R,4aR,6aS,7R,8R,10aR,10bR,12aR)-2-(2,6-diamino-hexanoyloxy)-3-((2-methyl)ethoxy)-8-[(1R)-1,2-dimethylpropyl]-1,6a,8,10a-tetramethyl-1,3,4,6,6a,7,8,9,10,10a,10b,11,12,12a-tetradecahydro-2H-1,4a-(methanooxymethano)chrysene-7-carboxylic acid.

13. The compound according to claim 1, wherein
$R^1$ is selected from the group consisting of:
  a) O—$(C_1-C_{12})$alkyl,
  b) OC(O)H, and
  c) OC(O)—$(C_1-C_{12})$alkyl;
$R^2$ is selected from the group consisting of:
  a) $(C_1-C_{12})$alkyl, and
  b) heterocyclyl, where said heterocyclyl groups are chosen from 5- to 8-membered rings containing from 1 to 4 heteroatoms independently selected from N, O and S, and
said $R^2$ is substituted by 0 to 4 $R^4$ groups;
$R^3$ is COOH;
each $R^4$ is independently selected from the group consisting of:
  a) OH,
  b) $NR^5_2$,
  c) $O(C_1-C_{12})$alkyl,
  d) $C(O)R^6$, and
  e) $S(O)_2R^6$, and
said $R^4$ is substituted by 0 to 4 $R^7$ groups;
each $R^5$ is independently selected from the group consisting of:
  a) H, and
  b) $(CH_2)_{0-12}R^6$, and
said $R^5$ is substituted by 0 to 13 $R^7$ groups;
each $R^6$ is independently selected from the group consisting of:
  a) H,
  b) $(C_1-C_{12})$alkyl,
  c) $(C_3-C_{12})$cycloalkyl,
  d) $(CH_2)_{0-6}$-phenyl,
  e) heterocyclyl,
  f) halogen, and
said $R^6$ is substituted by 0 to 13 $R^7$ groups; and
each $R^7$ is independently selected from the group consisting of:
  a) O—$(C_1-C_{12})$alkyl, and
  b) halogen, and
said $R^7$ is unsubstituted.

14. A composition comprising a compound and a carrier, adjuvant or vehicle, wherein said compound comprises a compound of Formula (I)

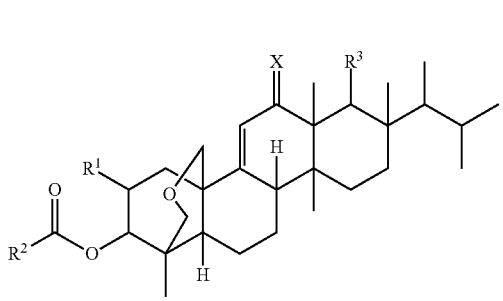

or a pharmaceutically acceptable salt or prodrug thereof, wherein:

X is selected from the group consisting of O and H,H;
$R^1$ is selected from the group consisting of:
 a) OH,
 b) O—$(C_1$-$C_{12})$alkyl,
 c) O—$(C_3$-$C_8)$cycloalkyl,
 d) O-heterocyclyl,
 e) OC(O)H,
 f) OC(O)—$(C_1$-$C_{12})$alkyl,
 g) OC(O)—$((C_3$-$C_8)$cycloalkyl, and
 h) OC(O)-(heterocyclyl),
  where said heterocyclyl groups are chosen from 5- to 8-membered rings containing from 1 to 4 heteroatoms independently selected from N, O and S;
$R^2$ is selected from the group consisting of:
 a) $(C_1$-$C_{12})$alkyl, and
 b) heterocyclyl, where said heterocyclyl groups are chosen from 5- to 8-membered rings containing from 1 to 4 heteroatoms independently selected from N, O and S, and
 said $R^2$ is substituted by 0 to 4 $R^4$ groups;
$R^3$ is selected from the group consisting of:
 a) $CH_2OH$,
 b) $CH_2OC(O)(C_1$-$C_{12}$ alkyl),
 c) COOH,
 d) COO$(C_1$-$C_{12})$alkyl, and
 e) COO$(CH_2)_{0-6}$phenyl;
each $R^4$ is independently selected from the group consisting of:
 a) $(C_1$-$C_{12})$alkyl,
 b) $(C_3$-$C_8)$cycloalkyl,
 c) OH,
 d) $NR^5{}_2$,
 e) $ONR^5{}_2$,
 f) $O(C_1$-$C_2)$alkyl,
 g) $C(O)R^6$,
 h) $S(O)_2R^6$, and
 i)

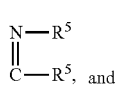

said $R^4$ is substituted by 0 to 4 $R^7$ groups;
each $R^5$ is independently selected from the group consisting of:
 a) H,
 b) $(CH_2)_{0-12}R^6$,
 c) $C(O)R^6$,
 d) $S(O)_2R^6$, and
 e)

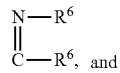

said $R^5$ is substituted by 0 to 13 $R^7$ groups;
each $R^6$ is independently selected from the group consisting of:
 a) H,
 b) OH,
 c) $(C_1$-$C_{12})$alkyl,
 d) O—$(C_1$-$C_{12})$alkyl,
 e) $(C_3$-$C_{12})$cycloalkyl,
 f) $(CH_2)_{0-6}$-phenyl,
 g) heterocyclyl, where said heterocyclyl groups are chosen from 5- to 8-membered rings containing from 1 to 4 heteroatoms independently selected from N, O and S,
 h) $C(O)R^8$,
 i) $NR^8{}_2$,
 j) halogen, and
 said $R^6$ is substituted by 0 to 13 $R^7$ groups;
each $R^7$ is independently selected from the group consisting of:
 a) OH,
 b) $(C_1$-$C_{12})$alkyl,
 c) O—$(C_1$-$C_{12})$alkyl,
 d) S—$(C_1$-$C_{12})$alkyl,
 e) $(CH_2)_{0-6}$-phenyl,
 f) heterocyclyl, where said heterocyclyl groups are chosen from 5- to 8-membered rings containing from 1 to 4 heteroatoms independently selected from N, O and S,
 g) $C(O)R^8$,
 h) $OC(O)R^8$,
 i) $NR^8{}_2$,
 j) halogen, and
 said $R^7$ is substituted by 0 to 13 $R^9$ groups;
each $R^8$ is independently selected from the group consisting of:
 a) H,
 b) $(C_1$-$C_{12})$alkyl,
 c) O—$(C_1$-$C_{12})$alkyl,
 d) $(C_3$-$C_{12})$cycloalkyl,
 e) $(CH_2)_{0-6}$-phenyl,
 f) heterocyclyl, where said heterocyclyl groups are chosen from 5- to 8-membered rings containing from 1 to 4 heteroatoms independently selected from N, O and S,
 g) $C(O)R^{11}$, and
 said $R^8$ is substituted by 0 to 13 $R^9$ groups;
each $R^9$ is independently selected from the group consisting of:
 a) OH,
 b) $(C_1$-$C_{12})$alkyl,
 c) O—$(C_1$-$C_{12})$alkyl,
 d) $(C_3$-$C_{12})$cycloalkyl,
 e) heterocyclyl, where said heterocyclyl group groups are chosen from 5- to 8-membered rings containing from 1 to 4 heteroatoms independently selected from N, O and S, f) C(O)R$^{11}$,
g) NR$^{11}_2$,
h) halogen, and
said R$^9$ is substituted by 0 to 13 R$^{10}$ groups;
each R$^{10}$ is independently selected from the group consisting of:
a) halogen,
b) =O, and
c) C(O)R$^{11}$; and
R$^{11}$ is selected from the group consisting of:
a) H, and
b) (C$_1$-C$_{12}$)alkyl.

15. The composition according to claim 14, further comprising a second therapeutic agent.

16. A method of treating a fungal infection in a patient in need thereof, comprising administering to said patient an effective amount of a compound of Formula (I)

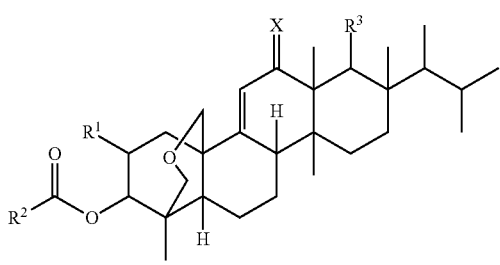

(I)

or a pharmaceutically acceptable salt or prodrug thereof, wherein:
X is selected from the group consisting of O and H,H;
R$^1$ is selected from the group consisting of:
  a) OH,
  b) O—(C$_1$-C$_{12}$)alkyl,
  c) O—(C$_3$-C$_8$)cycloalkyl,
  d) O-heterocyclyl,
  e) OC(O)H,
  f) OC(O)—(C$_1$-C$_{12}$)alkyl,
  g) OC(O)—((C$_3$-C$_8$)cycloalkyl, and
  h) OC(O)-(heterocyclyl),
  where said heterocyclyl groups are chosen from 5- to 8-membered rings containing from 1 to 4 heteroatoms independently selected from N, O and S;
R$^2$ is selected from the group consisting of:
  a) (C$_1$-C$_{12}$)alkyl, and
  b) heterocyclyl, where said heterocyclyl groups are chosen from 5- to 8-membered rings containing from 1 to 4 heteroatoms independently selected from N, O and S, and
  said R$^2$ is substituted by 0 to 4 R$^4$ groups;
R$^3$ is selected from the group consisting of:
  a) CH$_2$OH,
  b) CH$_2$OC(O)(C$_1$-C$_{12}$ alkyl),
  c) COOH,
  d) COO(C$_1$-C$_{12}$)alkyl, and
  e) COO(CH$_2$)$_{0-6}$phenyl;
each R$^4$ is independently selected from the group consisting of:
  a) (C$_1$-C$_{12}$)alkyl,
  b) (C$_3$-C$_8$)cycloalkyl,
  c) OH,
  d) NR$^5_2$,
  e) ONR$^5_2$,
  f) O(C$_1$-C$_{12}$)alkyl,
  g) C(O)R$^6$,
  h) S(O)$_2$R$^6$, and
  i)

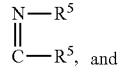

said R$^4$ is substituted by 0 to 4 R$^7$ groups;
each R$^5$ is independently selected from the group consisting of:
  a) H,
  b) (CH$_2$)$_{0-12}$R$^6$,
  c) C(O)R$^6$,
  d) S(O)$_2$R$^6$, and
  e)

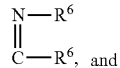

said R$^5$ is substituted by 0 to 13 R$^7$ groups;
each R$^6$ is independently selected from the group consisting of:
  a) H,
  b) OH,
  c) (C$_1$-C$_{12}$)alkyl,
  d) O—(C$_1$-C$_{12}$)alkyl,
  e) (C$_3$-C$_{12}$)cycloalkyl,
  f) (CH$_2$)$_{0-6}$-phenyl,
  g) heterocyclyl, where said heterocyclyl groups are chosen from 5- to 8-membered rings containing from 1 to 4 heteroatoms independently selected from N, O and S,
  h) C(O)R$^8$,
  i) NR$^8_2$,
  j) halogen, and
  said R$^6$ is substituted by 0 to 13 R$^7$ groups;
each R$^7$ is independently selected from the group consisting of:
  a) OH,
  b) (C$_1$-C$_{12}$)alkyl,
  c) O—(C$_1$-C$_{12}$)alkyl,
  d) S—(C$_1$-C$_{12}$)alkyl,
  e) (CH$_2$)$_{0-6}$-phenyl,
  f) heterocyclyl, where said heterocyclyl groups are chosen from 5- to 8-membered rings containing from 1 to 4 heteroatoms independently selected from N, O and S,
  g) C(O)R$^8$,
  h) OC(O)R$^8$,
  i) NR$^8_2$,
  j) halogen, and
  said R$^7$ is substituted by 0 to 13 R$^9$ groups;
each R$^8$ is independently selected from the group consisting of:
  a) H,
  b) (C$_1$-C$_{12}$)alkyl,
  c) O—(C$_1$-C$_{12}$)alkyl,
  d) (C$_3$-C$_{12}$)cycloalkyl,
  e) (CH$_2$)$_{0-6}$-phenyl, f) heterocyclyl, where said heterocyclyl groups are chosen from 5- to 8-membered rings containing from 1 to 4 heteroatoms independently selected from N, O and S,
g) $C(O)R^{11}$, and
said $R^8$ is substituted by 0 to 13 $R^9$ groups;
each $R^9$ is independently selected from the group consisting of:
a) OH,
b) $(C_1-C_{12})$alkyl,
c) O—$(C_1-C_{12})$alkyl,
d) $(C_3-C_{12})$cycloalkyl,
e) heterocyclyl, where said heterocyclyl groups are chosen from 5- to 8-membered rings containing from 1 to 4 heteroatoms independently selected from N, O and S,
f) $C(O)R^{11}$,
g) $NR^{11}_2$,
h) halogen, and
said $R^9$ is substituted by 0 to 13 $R^{10}$ groups;
each $R^{10}$ is independently selected from the group consisting of:
a) halogen,
b) =O, and
c) $C(O)R^{11}$; and
$R^{11}$ is selected from the group consisting of:
a) H, and
b) $(C_1-C_{12})$alkyl.

17. The method according to claim 16, wherein said fungal infection is caused by *Cryptococcus* spp., *Candida* spp. or *Aspergillus* spp. fungi.

\* \* \* \* \*